(12) United States Patent
Cereseto et al.

(10) Patent No.: US 11,525,127 B2
(45) Date of Patent: Dec. 13, 2022

(54) HIGH-FIDELITY CAS9 VARIANTS AND APPLICATIONS THEREOF

(71) Applicant: UNIVERSITA' DEGLI STUDI DI TRENTO, Trento (IT)

(72) Inventors: Anna Cereseto, Trento (IT); Antonio Casini, Pagnacco (IT); Gianluca Petris, Sauris (IT); Alberto Inga, Trento (IT); Michele Olivieri, Toronto (CA)

(73) Assignee: UNIVERSITA' DEGLI STUDI DI TRENTO, Trento (IT)

( * ) Notice: Subject to any disclaimer, the term of this patent is extended or adjusted under 35 U.S.C. 154(b) by 416 days.

(21) Appl. No.: 16/485,253

(22) PCT Filed: Feb. 14, 2018

(86) PCT No.: PCT/EP2018/053717
§ 371 (c)(1),
(2) Date: Aug. 12, 2019

(87) PCT Pub. No.: WO2018/149888
PCT Pub. Date: Aug. 23, 2018

(65) Prior Publication Data
US 2020/0149020 A1    May 14, 2020

(30) Foreign Application Priority Data

Feb. 14, 2017  (IT) .................. 102017000016321

(51) Int. Cl.
*C12N 9/22*  (2006.01)
*A61K 38/00*  (2006.01)

(52) U.S. Cl.
CPC ............... *C12N 9/22* (2013.01); *A61K 38/00* (2013.01); *C12N 2800/80* (2013.01)

(58) Field of Classification Search
None
See application file for complete search history.

(56) References Cited

U.S. PATENT DOCUMENTS 9,512,446 B1 * 12/2016 Joung .................. C12Y 301/00
2016/0102324 A1 * 4/2016 Duchateau ........... C12N 15/907
                                                    800/21

FOREIGN PATENT DOCUMENTS

| WO | WO-2016123243 A1 * | 8/2016 | ........... C12Q 1/6818 |
| WO | 2016/164797 A1 | 10/2016 | |
| WO | 2016/205613 A1 | 12/2016 | |
| WO | 2018/149888 A1 | 8/2018 | |

OTHER PUBLICATIONS

BLAST search of SEQ ID No. 1. *Streptococcus pyogenes* Cas9 protein. Retrieved on Jan. 18, 2022. Downloaded from website: <blast.ncbi.nlm.nih.gov/Blast.cgi> pp. 1-29.*

Singh, R.K. et al. 2018. Protein engineering approaches in the post-genomic era. Current Protein and Peptide Science 19: 5-15; specif. p. 11.*

Zhang, M. et al. 2018. Propagated perturbations from a peripheral mutation shows interactions supporting WW domain thermostability. Structure 26: 1474-1485; specif. p. 1475.*

Makarova, K.S. et al. Annotation and classification of CRISPR-Cas systems. In: CRISPR, Methods and Protocols. Chapt. 4. Humana Press. Copyright 2015. Springer Science + Business Media, N.Y. pp. 47-75; specif. p. 49, 57.*

Ford, T. 2015. Enhancing CRISPR targeting specificity with eSpCas9, SpCas9-HF1, & HypaCas9. Datasheet [online], addgene blog. Retrieved on Jan. 21, 2022. Downloaded from the internet: <https://blog.addgene.org/enhancing-crispr-targeting-specificity-with-espcas9-and-spcas9-hf1> pp. 1-17; specif. p. 2.*

Slaymaker, I.M. 2015. Rationally engineered Cas9 nucleases with improved specificity. Science 351(6268): 84-88.*

Italian Search Report completed Sep. 9, 2019 in IT 201800010681.
International Search Report and Written Opinion for International Application No. PCT/EP2018/053717 dated Jul. 19, 2018.

Casini et al., 2018, "A highly specific SpCas9 variant is identified by in vivo screening in yeast," Nature Biotechnology, 36(3):265-271.

Casini et al., 2016, "Identification of high-fidelity Cas9 variants using a yeast-based screening," Human Gene Therapy, 27(11):A41 and Conference on Changing the Face of Modern Medicine—Stem Cells and Gene Therapy; Florence, Italy (Abstract).

Casini "Identification of high-fidelity Cas9 variants using a yeast-based screening" slides presented at ESGCT/ISSCR/ABCD Collaborative Congress Florence, Italy; dated Oct. 21, 2016.

Jinek et al., 2014, "Structures of Cas9 Endonucleases Reveal RNA-Mediated Conformational Activation," Science, 343(6176):1247997.

(Continued)

*Primary Examiner* — Olivia M. Wise
*Assistant Examiner* — Sharon M. Papciak
(74) *Attorney, Agent, or Firm* — Biospark Intellectual Property Law

(57) ABSTRACT

To address the limitations deriving from the unspecific genomic cleavages of the *Streptococcus pyogenes* Cas9 (SpCas9) and to identify variants with higher cleavage fidelity, the present invention describes a yeast-based assay which allows to simultaneously evaluate the on- and off-target activity towards two engineered genomic targets. The screening of SpCas9 variants obtained by random mutagenesis of the Red-II domain allowed the identification of hits with increased on/off ratios. The best performing nuclease, evoCas9, was isolated through the combination of the identified mutations within a single variant. Side by side analyses with previously reported rationally designed variants demonstrated a significant improvement in fidelity of evoCas9 of the present invention.

21 Claims, 9 Drawing Sheets
Specification includes a Sequence Listing.

(56) References Cited

OTHER PUBLICATIONS

Kleinstiver et al., 2016, "High-Fidelity CRISPR-Cas9 nucleases with No. detectable genome-wide off-target effects," Nature, 529(7587):490-495.
Slaymaker et al., 2016, "Rationally engineered Cas9 nucleases with improved specificity," Science, 351 (6268):84-88.

* cited by examiner

HIGH-FIDELITY CAS9 VARIANTS AND APPLICATIONS THEREOF

SEQUENCE LISTING

The instant application contains a Sequence Listing which has been submitted electronically in ASCII format and is hereby incorporated by reference in its entirety. Said ASCII copy, created on Nov. 4, 2019, is named ALA-001US_SL.txt and is 51,884 bytes in size.

FIELD OF THE INVENTION

The present invention pertains to the fields of enzymes and nucleic acid binding proteins, in particular Cas9 variants.

STATE OF THE ART

The number of biotechnological applications involving the CRISPR-Cas9 system has seen a huge increase in the past years, driven by the flexibility and efficacy of this new genome editing tool. Target sites are usually recognized by Cas9 through a so-called "guide RNA" (gRNA) sequence complementary to a target nucleic acid including a protospacer sequence. Target recognition requires also the presence of a short neighbouring PAM (protospacer adjacent motives) sequence. The target nucleic acid is usually DNA, but in some circumstances can be also RNA. Guide RNAs can be formed by one or more small RNAs. Genome editing by the CRISPR-Cas9 approach has been applied with success on a variety of cell types and species, clearly demonstrating the effectiveness and robustness that have to characterize a game-changer technology. Importantly, both basic research and therapeutic-oriented applications, aside from efficacy, require high targeting specificity for editing. However, several studies have shown that Cas9 cleavages into the genome are not always directed to the intended sites and unwanted lesions can be introduced in DNA regions sharing different levels of similarity with the selected target. In addition, the prediction of such unwanted activity is difficult and often unreliable, due to the absence of simple rules governing the phenomenon. Moreover, the assessment of the off-target effects is not always simple, and the results obtained applying different methods are often not in accordance. Hence, enhancement of the specificity of the CRISPR-Cas9 toolkit is a highly desirable improvement of this key technology, allowing its safe use in all the application fields, especially in human therapeutic applications.

Different strategies have been proposed to reduce the introduction of unwanted off-target mutations by CRISPR-Cas9, such as the tight control of *Streptococcus pyogenes* Cas9 (SpCas9) intracellular levels, the introduction of engineered gRNAs characterized by shorter protospacers with less complementarity to the target sequence (truncated g-RNAs), the fusion of SpCas9 to specific DNA-binding domains to direct its binding or the exploitation of paired SpCas9 nickases and paired catalytically inactive SpCas9 fused to the FokI endonuclease domain. However, none of these approaches are off-target free and due to their intrinsic molecular complexity are often defective in on-target activity.

Recently, two groups have reported the structure-guided rational engineering of SpCas9 variants characterized by a lower propensity to cleave off-target sites. Slaymaker I M et al. (Science. 2016, 351(6268):84-8) generated three SpCas9 mutants with both high efficiency (near wild type levels of on-target insertions-deletions, indel, formation) and specificity (no detectable indel formation at the EMX(1) and VEGFA(1) off-target sites, standard loci for specificity essay): SpCas9 (K855A), SpCas9 (K810A/K1003A/R1060A) [also referred to as eSpCas9(1.0)], and SpCas9 (K848A/K1003A/R1060A) [also referred to as eSpCas9 (1.1)].

Kleinstiver B P et al. (Nature. 2016, 529(7587):490-5) generated 15 different SpCas9 variants bearing all possible single, double, triple and quadruple combinations of N497A, R661A, Q695A, and Q926A substitutions. The triple mutated variant (R661A/Q695A/Q926A) and the quadruple substituted variant (N497A/R661A/Q695A/Q926A, hereafter referred to as SpCas9-HF1) both showed minimal EGFP disruption at near-background levels with four mismatched sgRNAs. Also from these recent efforts it is evident that a major need in the field is the generation of genome editing systems with no off-target activity.

Aim of the present invention is to provide novel, at least alternative, high-fidelity Cas9 variants.

SUMMARY OF THE INVENTION

Subject-matter of the present invention is an isolated modified Cas9 molecule comprising at least one mutation located at an amino acid residue positions selected in the group consisting of: K377, E387, D397, R400, D406, A421, L423, R424, Q426, Y430, K442, P449, V452, A456, R457, W464, M465, K468, E470, T474, P475, W476, F478, K484, S487, A488, T496, F498, L502, N504, K506, P509, F518, N522, E523, K526, L540, S541, I548, D550, F553, V561, K562, E573, A589, L598, D605, L607, N609, N612, E617, D618, D628, R629, R635, K637, L651, K652, R654, T657, G658, L666, K673, S675C, I679V, L680, L683, N690, R691, N692, F693, S701, F704, Q712, G715, Q716, H723, I724, L727, I733, L738 and Q739; wherein the position of the modified amino acids sequence is identified by reference to the amino acid numbering in the corresponding position of an unmodified mature *Streptococcus pyogenes* Cas9 (SpCas9), as identified by SEQ ID NO: 1.

In a preferred embodiment the modified Cas9 comprises at least one mutation at position K526.

SpCas9 variants according to the invention were initially obtained by random mutagenesis of its REC1-II domain and were screened for the identification of hits with increased on/off ratios by way of a yeast-based assay which allows to simultaneously evaluate the on- and off-target activity towards two engineered genomic targets. After further validation in mammalian cells, Cas9 variants according to the invention were generated. Surprisingly, a modified SpCas9 according to the invention showed a significantly reduced off-target activity when compared to wild-type SpCas9 and side by side analyses with previously reported rationally designed variants demonstrated a significant improvement in fidelity of a SpCas9 variant of the invention. Additionally, a modified SpCas9 according to the invention and having the additional D10A and H840A mutations fused with a transcriptional activation domain (VP64) showed a significantly reduced off-target activity when compared with wild-type Cas9 variant containing the D10A and H840A mutations.

DETAILED DESCRIPTION OF THE INVENTION

The present invention describes isolated Cas9 molecules with increased specificity obtained through random mutagenesis of the REC1-II domain of Cas9 and screening using a yeast based assay to evaluate simultaneously the on- and off-target activity of each generated variant. Selected hits were further refined by screening in a mammalian system.

In a first aspect of the invention, the Cas9 variants comprise at least one mutation located at an amino acid residue positions selected in the group consisting of K526, K377, E387, D397, R400, D406, A421, L423, R424, Q426, Y430, K442, P449, V452, A456, R457, W464, M465, K468, E470, T474, P475, W476, F478, K484, S487, A488, T496, F498, L502, N504, K506, P509, F518, N522, E523, L540, S541, I548, D550, F553, V561, K562, E573, A589, L598, D605, L607, N609, N612, E617, D618, D628, R629, R635, K637, L651, K652, R654, T657, G658, L666, K673, S675, I679, L680, L683, N690, R691, N692, F693, S701, F704, Q712, G715, Q716, H723, I724, L727, I733, L738 and Q739;

wherein the position of the modified amino acids sequence is identified by reference to the amino acid numbering in the corresponding position of an unmodified mature Streptococcus pyogenes Cas9 (SpCas9), as identified by SEQ ID NO: 1.

Preferably according to the invention the mutation at position K526 is selected in the group consisting of K526N and K526E; more preferably K526E.

According to a preferred embodiment of the invention the modified Cas9 having K526 mutated comprises one or more further mutations located at amino acid residue positions selected in the group consisting of:

K377, E387, D397, R400, Q402, R403, F405, D406, N407, A421, L423, R424, Q426, Y430, K442, P449, Y450, V452, A456, R457, W464, M465, K468, E470, T472, I473, T474, P475, W476, F478, K484, S487, A488, M495, T496, N497, F498, L502, N504, K506, P509, Y515, F518, N522, E523, L540, S541, I548, D550, F553, V561, K562, E573, A589, L598, D605, L607, N609, N612, E617, D618, D628, R629, R635, K637, L651, K652, R654, T657, G658, W659, R661, L666, K673, S675, I679, L680, L683, N690, R691, N692, F693, Q695, H698, S701, F704, Q712, G715, Q716, H721, H723, I724, L727, A728, I733, L738, Q739.

The one or more further mutations are a number comprised between 1 and 8.

Preferably the one or more further mutation is selected in the group consisting of: K377E, E387V, D397E, R400H, Q402R, R403H, F405L, D406Y, D406V, N407P, N407H, A421V, L423P, R424G, Q426R, Y430C, K442N, P449S, Y450A, Y450S, Y450H, Y450N, V452I, A456T, R457P, R457Q, W464L, M465R, K468N, E470D, T472A, I473F, I473V, T474A, P475H, W476R, F478Y, F478V, K484M, S487Y, A488V, M495V, M495T, T496A, N497A, F498I, F498Y, L502P, N504S, K506N, P509L, Y515N, F518L, F518I, N522K, N522I, E523K, E523D, L540Q, S541P, I548V, D550N, F553L, V561M, V561A, K562E, E573D, A589T, L598P, D605V, L607P, N609D, N609S, N612Y, N612K, E617K, D618N, D628G, R629G, R635G, K637N, L651P, L651H, K652E, R654H, T657A, G658E, W659R, R661A, R661W, R661L, R661Q, R661S, L666P, K673M, S675C, I679V, L680P, L683P, N690I, R691Q, R691L, N692I, F693Y, Q695A, Q695H, Q695L, H698Q, H698P, S701F, F704S, Q712R, G715S, Q716H, H721R, H723L, I724V, L727H, A728G, A728T, I733V, L738P, Q739E, Q739P and Q739K.

In preferred embodiments the total number of the above said mutations is comprised between 1 and 9; preferably between 1 and 5; most preferably between 1 and 4. SEQ ID N: 1 is the sequence having accession number NP_269215 (NCBI) referred to SpCas9.

According to the invention, the modified polypeptide, excluded the mutations, preferably has an identity of at least 50%, 60%, 70%, 80%, 90%, 95%, 99% or 100% with SEQ ID N: 1.

Percent identity between two polypeptides or nucleic acid sequences can be determined by those skilled in the art by use of alignment softwares (i.e. the BLAST program).

Preferably the modified Cas9 is a S. pyogenes Cas9. In some embodiments Cas9 is a SpCas9 orthologous (i.e. S. thermophilus, S. aureus, N meningitides). In some embodiments the Cas9 orthologue has at least 10% or 25% amino acid identity to the Rec1-II domain of SpCas9 and complete amino acid identity of any percentage between 10% or 25% and 100% to SpCas9. Those skilled in the art can determine the appropriate homologous residues to be modified by sequence and/or structural alignments. Identified amino acids can be modified conservatively with substitutions within the following groups: glycine, alanine; valine, isoleucine, leucine; aspartic acid, glutamic acid, asparagine, glutamine; serine, threonine; lysine, arginine; phenylalanine, tyrosine.

The modified polypeptide retains the ability to interact with gRNAs and/or with a target DNA or RNA.

According to the invention a mutation X1nnnX2 means that at position nnn the amino acid X2 is present in place of the amino acid X1 which is present in the wild-type polypeptide; so, for example, K526E means that the amino acid at position 526 corresponds to a glutamic acid (Glu or E), in place of the amino acid lysine (Lys or K) which is present in the wild-type polypeptide.

According to a preferred embodiment of the invention, the modified Cas9 polypeptide comprises a mutation at position K526 and one or more further mutations at a position selected in the group consisting of Y450, M495, Y515, R661, N690, R691, Q695, H698; preferably M495, Y515, R661, H698.

According to a preferred embodiment of the invention, the at least one further mutation is selected in the group consisting of Y450S, M495V, Y515N, R661X, N690I, R691Q, Q695H, H698Q; preferably selected in the group consisting of M495V, Y515N, K526E, R661X, H698Q; wherein X is an amino acid selected in the group consisting of L, Q and S; preferably X is Q or S.

According to a preferred embodiment of the invention the modified Cas9 polypeptide comprises a double mutation selected in the group consisting of K526E+Y450S, K526E+M495V, K526E+Y515N, K526E+R661X, K526E+N690I, K526E+R691Q, K526E+Q695H and K526E+H698Q; wherein X is an amino acid selected in the group consisting of L, Q and S; preferably X is Q or S.

According to a preferred embodiment of the invention the modified Cas9 polypeptide as above described comprises a triple mutation selected in the group consisting of M495V+K526E+R661X, Y515N+K526E+R661X, K526E+R661X+H698Q and M495V+Y515N+K526E; wherein X is an amino acid selected in the group consisting of L, Q and S; preferably X is Q or S.

According to a preferred embodiment of the invention, the modified Cas9 polypeptide as above described comprises a quadruple mutation selected in the group consisting of M495V+Y515N+K526E+R661X and M495V+K526E+R661X+H698Q; wherein X is an amino acid selected in the group consisting of L, Q and S; preferably X is Q or S.

Most preferred is a modified Cas9 polypeptide as above described comprising a quadruple mutation M495V+Y515N+K526E+R661Q (herein after also named evoCas9) or M495V+Y515N+K526E+R661S (herein after also named evoCas9-II). For an aspect the subject-matter of the present invention is an isolated modified Cas9 polypeptide comprising at least one mutation selected in the group consisting of K377E, E387V, D397E, R400H, Q402R, R403H, F405L, D406Y, D406V, N407P, N407H, A421V, L423P, R424G, Q426R, Y430C, K442N, P449S, Y450S, Y450H, Y450N, V452I, A456T, R457P, R457Q, W464L, M465R, K468N, E470D, T472A, I473F, I473V, T474A, P475H, W476R, F478Y, F478V, K484M, S487Y, A488V, M495V, M495T, T496A, F498I, F498Y, L502P, N504S, K506N, P509L, Y515N, F518L, F518I, N522K, N522I, E523K, E523D, K526E, K526N, L540Q, S541P, I548V, D550N, F553L, V561M, V561A, K562E, E573D, A589T, L598P, D605V, L607P, N609D, N609S, N612Y, N612K, E617K, D618N, D628G, R629G, R635G, K637N, L651P, L651H, K652E, R654H, T657A, G658E, W659R, R661W, R661L, R661Q, R661S, L666P, K673M, S675C, I679V, L680P, L683P, N690I, R691Q, R691L, N692I, F693Y, Q695H, Q695L, H698Q, H698P, S701F, F704S, Q712R, G715S, Q716H, H721R, H723L, I724V, L727H, A728G, A728T, I733V, L738P, Q739E, Q739P and Q739K.

According to a preferred embodiment the invention relates to a modified Cas9 polypeptide comprising:
  a single mutation selected in the group consisting of D406Y, W464L, T474A, K526E, N612K, L683P; or
  a double mutation selected in the group consisting of R400H+Y450S, D406V+E523K, A421V+R661W, R424G+Q739P, W476R+L738P, P449S+F704S, N522K+G658E, E523D+E617K, L540Q+L607P, W659R+R661W, S675C+Q695L and I679V+H723L; or
  a triple mutation selected in the group consisting of K377E+L598P+L651H, D397E+Y430C+L666P, Q402R+V561M+Q695L, N407P+F498I+P509L, N407H+K637N+N690I, Y450H+F553L+Q716H, Y450N+H698P+Q739K, T472A+P475H+A488V, I473F+D550N+Q739E, F478Y+N522I+L727H, K484M+Q695H+Q712R, S487Y+N504S+E573D, T496A+N609D+A728G, R654H+R691Q+H698Q and R691L+H721R+I733V;
  a quadruple mutation selected in the group consisting of F405L+F518L+L651P+I724V, L423P+M465R+Y515N+K673M, R457P+K468N+R661W+G715S, E470D+I548V+A589T+Q695H, A488V+D605V+R629G+T657A and M495V+K526N+S541P+K562E; or
  five mutations selected in the group consisting of R403H+N612Y+L651P+K652E+G715S;
  six mutations selected in the group consisting of E387V+V561A+D618N+D628G+L680P+S701F, R403H+K526E+N612Y+L651P+K652E+G715S, R403H+M495T+N612Y+L651P+K652E+G715S, R403H+L502P+N612Y+L651P+K652E+G715S, R403H+K506N+N612Y+L651P+K652E+G715S, R403H+N612Y+L651P+K652E+N692I+G715S; or
  seven mutations selected in the group consisting of R403H+A456T+N612Y+L651P+K652E+G715S+G728T, R403H+F498Y+N612Y+L651P+K652E+R661L+G715S, R403H+Q426R+F478V+N612Y+L651P+K652E+G715S; or
  eight mutations selected in the group consisting of R403H+R442N+V452I+N609S+N612Y+R635G+L651P+K652E+F693Y+G715S; or
  nine mutations selected in the group consisting of R403H+R457Q+F518I+N612Y+R635G+L651P+K652E+F693Y+G715S.

Preferably, according to the invention, the modified Cas9 polypeptide comprises at least one mutation selected in the group consisting of Y450S, M495V, Y515N, K526E, R661X, N690I, R691Q, Q695H, H698Q; wherein X is selected in the group consisting of L, Q and S; preferably X is Q or S.

In some embodiments, the said mutations identified for Cas9 are suitable to improve the specificity of other Cas9 nuclease variants so far reported (SpCas9-HF1-4, eSpCas9 (1.0)-(1.1.)). Therefore, optionally the above described Cas9 variant may further comprise one or more additional mutations at residues L169A, K810A, K848A, Q926A, R1003A, R1060A, D1135E.

In some embodiments, the said mutations identified for Cas9 are suitable to improve the specificity of other Cas9 nickase, dCas9-FokI or dCas9. Therefore, optionally the above described Cas9 variant may further comprise at least one additional mutation at a residue selected in the group consisting of D10, E762, D839, H840, N863, H983 and D986 to decrease nuclease activity. Preferably such additional mutations are D10A, or D10N and H840A, H840N or H840Y. Preferably said mutations result in a Cas9 nickase or in a catalytically inactive Cas9 (Ran F et al. Cell. 2013, 154(6):1380-1389; Maeder M et al. Nature Methods. 2013, 10(10):977-979).

In some embodiments, the said mutations identified for Cas9 are suitable to improve the specificity of Cas9 nuclease variants recognizing alternative PAM sequences. Therefore, optionally the above described Cas9 variant may further comprise one or more additional mutations at residues D1135V/R1335Q/T1337R (QVR variant), D1135E/R1335Q/T1337R (EVR variant), D1135V/G1218R/R1335Q/T1337R (VRQR variant), D1135V/G1218R/R1335E/T1337R (VRER variant) according to US Patent US20160319260.

Further subject-matter of the present invention is also a variant SpCas9 protein as above described fused to other polypeptide sequences.

Preferably the Cas9 variant is fused to amino acid sequences that encode protein tags (i.e. V5-tag, FLAG-tag, myc-tag, HA-tag, GST-tag, polyHis-tag, MBP-tag), proteins, protein domains, transcription modulators, enzymes acting on small molecule substrates, DNA, RNA and protein modification enzymes (i.e. adenosine deaminase, cytidine deaminase, guanosyl transferase, DNA methyltransferase, RNA methyltransferases, DNA demethylases, RNA demethylases, dioxygenases, polyadenylate polymerases, pseudouridine synthases, acetyltransferases, deacetylase, ubiquitin-ligases, deubiquitinases, kinases, phosphatases, NEDD8-ligases, de-NEDDylases, SUMO-ligases, deSUMOylases, histone deacetylases, histone acetyltransferases histone methyltransferases, histone demethylases), protein DNA binding domains, RNA binding proteins, polypeptide sequences with specific biological functions (i.e. nuclear localization signals, mitochondrial localization signals, plastid localization signals, subcellular localization signals, destabilizing signals, Geminin destruction box motifs), biological tethering domains (i.e. MS2, Csy4 and lambda N protein).

Further subject-matter of the present invention is a method for producing a Cas9 variant as above described, said method comprising reconstituting the Cas9 variant from one or more fragment thereof; preferably whereby an intein or a protein intron or a dimerizing domain is included within the Cas9 polypeptide.

In some embodiment the reconstituting step can be performed in vitro in some other embodiment it can be performed in vivo (see below).

Preferably such fragments can be induced to reconstitute Cas9 protein by dimerization of a split-Cas9 (Wright A V et al. PNAS 2015 12(10):2984-9; Liu K I et al. Nat Chem Biol. 2016, 12(11):980-987).

Preferably such fragments can be induced to reconstitute a catalytically active Cas9 protein by intein dimerization of a split-Cas9 (Truong D J et al. Nucleic Acids Res 43(13): 6450-8).

According to the invention a vector is a system suitable for the delivery or expression of a nucleotide or protein sequence.

Further subject-matter of the present invention is also protein or ribonucleoprotein complexes or mixed protein, ribonucleoprotein and lipid complexes containing the modified Cas9 polypeptide (Cas9-sgRNA complexes, and their conjugation with additional protein, nucleic acid or lipid components such as but not limited to cell penetrating peptides, nucleic acid aptamers and lipidic vesicles).

Further subject-matter of the present invention is a protein or protein ribonucleotide vector containing the modified Cas9 polypeptide. In some embodiments such vector is a natural or an artificial complex or vesicle (see above). In some embodiments such vector is derived from a packaging or releasing cell. In some embodiments such vector is extracellular vesicle-based structures (i.e. but not limited to exosomes and exosomes like structures), or viral particles or viral-like particles containing the Cas9 modified polypeptide according to the invention.

Further subject-matter of the present invention is a sequence of nucleotides encoding for a modified Cas9 polypeptide as above described and fragments thereof.

Preferably, according to the invention, the sequence of nucleotides encoding a modified Cas9 as above described, or fragments thereof, is based on SEQ ID N: 2, which is the sequence having accession number NC_002737, or SEQ ID N. 3, which has been obtained through codon-optimization for the expression in human cells, and presents base substitutions corresponding to the above described mutations. The sequence of nucleotides of the invention, encoding a modified Cas9 polypeptide, preferably has, excluded the mutations, an identity of at least 50%, 60%, 70%, 80%, 90%, 95%, 99% A or 100% with SEQ ID N: 2 or SEQ ID N. 3.

Further subject-matter of the present invention is a nucleic acid comprising the sequence of nucleotides as above described.

A method for producing a modified Cas9 polypeptide as above described, whereby the modified Cas9 polypeptide is expressed by means of a nucleic acid as above described.

Further subject-matter of the present invention is a vector comprising the nucleic acid as above described; wherein said vector is suitable for gene expression in prokaryotic cells or eukaryotic cells (e.g. yeast, mammalian cells, insect cells, plant cells). Preferably the vector can be, but not limited to, a plasmid, a phagemid, a bacterial or yeast artificial chromosome, a DNA or an RNA fragment, or an *Agrobacterium*-based vector, or a viral vector.

The nucleic acid of the invention preferably is delivered through lentiSLiCES allowing further specificity through a self-limiting circuit as described in the Italian patent application IT 102016000102542. The nucleic acid of the invention preferably is delivered through a retroviral vector, an EIAV vector, a SIV vector, an adenoviral vector, an AAV vector, a herpes vector, a Baculovirus vector, a Vaccinia virus vector, a Sendai virus vector or a bacteriophage. Preferably the bacteriophage vector is based on the λ phage, the M13 phage, of the P1 phage.

Further subject-matter of the present invention is a nucleic acid comprising fragments of the sequence of nucleotides as above described.

Preferably when the translated polypeptides encoded by the two or more different nucleic acids comprising fragments of the sequence of nucleotides as above described can be used in vitro or in vivo to reconstitute a catalytically active Cas9 variant as above described.

Preferably if such fragments of Cas9 can be used to reconstitute Cas9 protein expression at the DNA level by exploiting recombination between different viral vectors (i.e. Wu Z et al. Mol Ther. 2010, 18(1)80-86).

Preferably if such fragments of Cas9 can be used to reconstitute a Cas9 protein at the transcription level by exploiting trans-splicing (Fine E J et al. Sci Rep. 2015, 5:10777).

Further subject-matter of the present invention is also a cell engineered to encode a nucleic acid or a vector as above described or a cell permanently modified by way of Cas9 variant of the invention.

Preferably the engineered cell is a prokaryotic cell, more preferably a bacterium. Preferably the engineered cell is a eukaryotic cell. Preferably is an animal cell. Preferably the engineered cell is a mammalian cell. More preferably is a human cell. Preferably the engineered cell is a somatic cell, more preferably is a tumor cell, most preferably is a stem cell or an induced pluripotent stem cell.

Further subject-matter of the present invention is also an animal engineered to encode a nucleic acid or a vector as above described or an animal permanently modified by way of Cas9 variant of the invention. Preferably the animal is a model organism (i.e. *Drosophila melanogaster*, mouse, mosquito, rat), or the animal is a farm animal or a farmed fish or a pet. Preferably the animal is a vector for at least a disease. More preferably the organism is a vector for human diseases (i.e. mosquitos, tick, birds).

Further subject-matter of the present invention is a plant engineered using a nucleic acid or a vector as above described or a plant permanently modified by way of Cas9 variant of the invention. Preferably, the plant is a crop (i.e. rice, soybean, wheat, tobacco, cotton, alfalfa, canola, corn, sugar beet).

Further subject-matter of the present invention is also a method for permanently modifying a cell, an animal or a plant, said method comprising using a Cas9 molecule of the invention for editing the DNA of the cell, animal or plant.

Further subject-matter of the present invention is also a sequence of nucleotides or a nucleic acid or a vector, as above described, for use as a medicament for gene therapy. Further subject-matter of the present invention is also a pharmaceutical composition comprising a sequence nucleotides or a nucleic acid or a vector, as above described, and at least one pharmaceutically acceptable excipient.

Further subject-matter of the present invention is also a pharmaceutical composition comprising a recombinant Cas9 polypeptide, containing the above described mutations, and at least one pharmaceutically acceptable excipient.

Further subject-matter of the present invention is also the in vitro use of a sequence nucleotides or a nucleic acid or a vector, as above described, for genome engineering, cell engineering, protein expression or other biotechnology applications.

Further subject matter of the invention is the use in vitro of a recombinant Cas9 polypeptide, containing the above described mutations, together with a gRNA for genome engineering, cell engineering, protein expression or other biotechnology applications.

Further subject matter of the invention is a kit of parts, for simultaneous, separate or sequential use, comprising a sequence of nucleotides or a nucleic acid or a vector or a recombinant Cas9 polypeptide as above described.

An in vitro or in vivo method for altering the genome of a cell, the method comprising the expression in the cell of the modified Cas9 as above described together with a guide RNA targeting a specific genomic sequence.

An in vitro or in vivo method for altering the transcriptome of a cell, the method comprising the expression in the cell of the modified dCas9-based transcriptional regulator as above described together with a guide RNA targeting a specific genomic sequence.

An in vitro or in vivo method for altering the epigenome of a cell, the method comprising the expression in the cell of the modified dCas9-based epigenome editor as above described together with a guide RNA targeting a specific genomic sequence.

The present invention will be better understood in light of the experiments below.

EXPERIMENTAL SECTION

Design of a Reporter Yeast Strain for the Detection of Cas9 Activity

Figure 1:
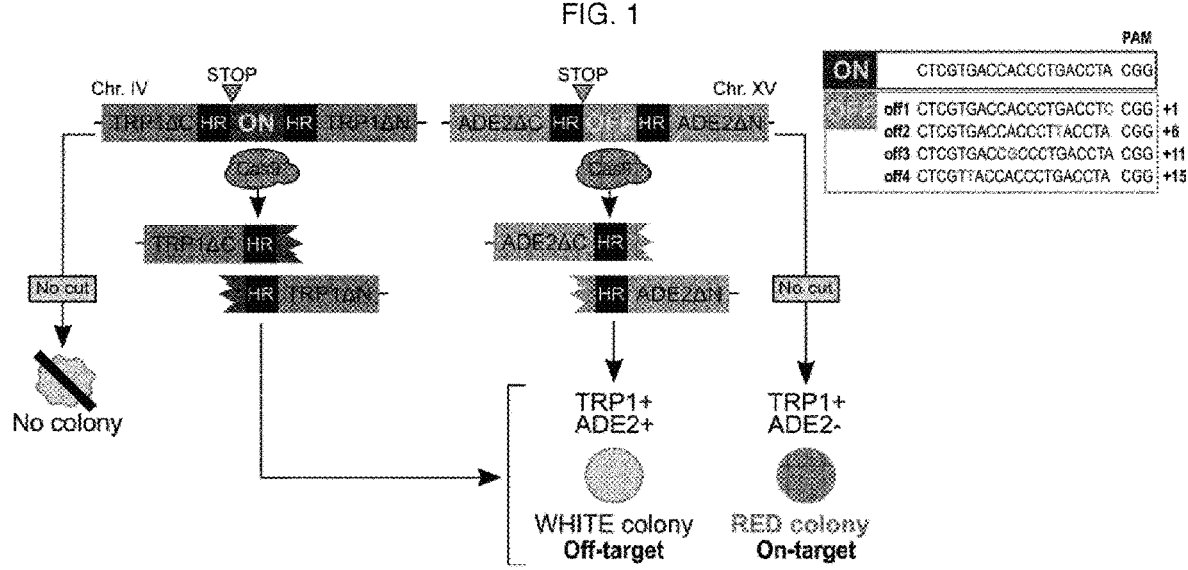
FIG. 1. Design of an in vivo yeast assay to quantify SpCas9 on- and off-target activity. Generation of yeast reporter strains. The TRP1 and ADE2 loci were modified by the insertion of a reporter cassette containing an on-target site (TRP1) or different off-target sequences (ADE2, sequences are reported in the upper-right box). The presence of homology regions (HR) on both sides of the target allows efficient repair by single strand annealing upon cleavage by Cas9. Using appropriate selective plates, it is possible to follow the editing status of the two loci. The survival of a colony will indicate TRP1 on-target cleavage, while the colour of the colony allows to assess the cleavage of the ADE2 off-target.

Saccaromyces cerevisiae was used as an experimental model to develop a directed evolution screen to isolate high-specificity SpCas9 variants. The advantage of using a yeast-based assay platform resides on one side in the similarities that yeast shares with bacteria, such as a fast doubling rate, the possibility to isolate single clones with ease and the availability of fast and reliable transformation protocols; on the other hand, yeast DNA organization and metabolism is similar to the one of higher eukaryotic cells. Therefore, the yeast model offers a flexible platform for high throughput screening combined with similarities with a mammalian system that increases the robustness of the screening outcome. Initially a strategy to generate an auxotrophic reporter yeast strains for the simultaneous measurement of Cas9 on- versus off-target activity was designed. This approach consisted in testing the modification of two yeast genomic loci: the TRP1 (chromosome IV) and ADE2 (chromosome XV). By using the delitto perfetto approach, the wild-type coding sequences of the two loci were split in two halves separated by the specific target sequence matching the on-target sgRNA in the case of TRP1 locus or by different off-target sequences in the case of the ADE2 locus (schematized in FIG. 1). Each off-target (ADE2off1-off4, Appendix Table 4) contained a single mismatch positioned at increasing distances from the PAM sequence. A 100 bp duplication was added on both sides of the target sequence (TRP1 or ADE2) and a stop codon was positioned immediately upstream, in between the two homology regions, to ensure premature interruption of translation (FIG. 1). The knockout of the TRP1 and ADE2 genes by reporter cassette insertion produces defects in the tryptophan and adenine metabolic pathways, suppressing growth in the absence of tryptophan and leading to the accumulation in the cell vacuole of an intermediate product of adenine biosynthesis when cells are grown at low concentrations of adenine, thus conferring a characteristic red pigmentation to the colonies on agar plates. Following the formation of double strand breaks induced by Cas9, each locus can be efficiently repaired by yeast cells using the single strand annealing repair pathway thanks to the presence of the two flanking homology regions, obtaining a reversion to prototrophy for the two nutrients. The successful editing event at each of the two loci can in turn be visualized using appropriate reporter plates, which are depleted of tryptophan and contain only low concentrations of adenine (SDluta$_5$, FIG. 1). The assay's complete readout consists in a two-step process. The first step consists in the evaluation of the on-target cleavage efficiency by comparing the number of colonies obtained on SDluta$_5$ reporter plates with those obtained when selecting only for the total number of transformants (SDlu plates). The second step consists in counting the number of red colonies (TRP1$^+$/ADE2$^-$), corresponding to on-target cleavages, and white colonies (TRP1$^+$/ADE2$^+$) in which also the off-target locus has been edited, on the reporter plates for the evaluation of the on- versus off-target activity. Four yeast strains were generated containing four potential off-target sites (ADE2off1-off4) and were named yACMO-off1/off4. Next, the rate of spontaneous reversion for the ADE2 and TRP1 loci of the different yACMO strains was evaluated to avoid the introduction of any confounding variable in the readout of the assay. Reversion of the TRP1 locus can in fact lead to the isolation of false positive clones, while spontaneous recombination of the ADE2 gene can generate false negative colonies. To approximate the experimental conditions used during our assay, each of the four strains separately was transformed with a plasmid encoding for SpCas9; after 24 hours incubation in selective medium, cells were spread on selective plates to measure the total number of transformants and a 1000-fold more cells were plated on selective plates depleted of tryptophan or adenine, to count the number of revertants for each locus. By comparing the number of colonies obtained in the different selective conditions it was possible to estimate a mean reversion frequency of approximately $1-1.5 \times 10^{-5}$ for both the TRP1 and ADE2 loci thus indicating negligible spontaneous reversion.

Validation of the yACMO Reporter Strain

Figure 2:
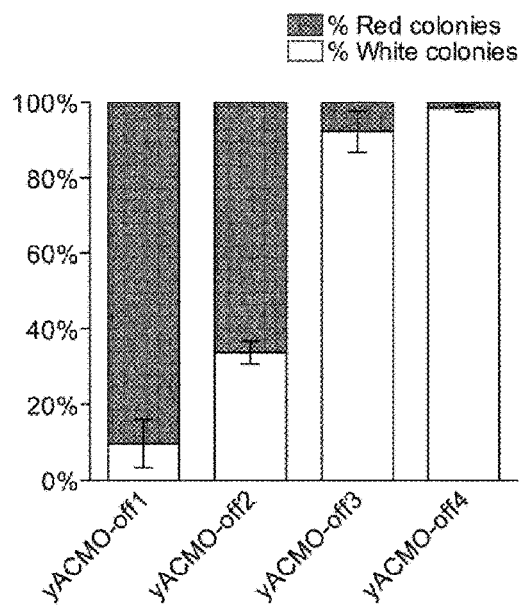
FIG. 2. Validation of the yACMO strain using wild-type SpCas9. Quantification of the mean percentage of red (on-target) and white (off-target) colonies after transformation of wt SpCas9 into the yACMO-off1/off4 reporter strains stably expressing an sgRNA matching the on-target sequence in the TRP1 locus. Cas9 expression was induced for 24h prior to plating. Error bars represent s.e.m. for n=3.

The functionality of the reporter assay was validated by testing the four reporter strains (yACMO-off1/off4) in combination with wild-type SpCas9. To maximize the overall efficiency, prior to the challenge with SpCas9, each of the strains was stably transformed with a plasmid expressing the sgRNA-on, perfectly matching the on-target sequence in the TRP1 locus. The four strains were then transformed with a plasmid for the expression of wild-type SpCas9 controlled by a galactose-inducible promoter and, after a 4 hour recovery incubation, induced overnight in galactose-containing media prior to plating on SDlu and reporter SDluta$_5$ plates. In these experimental conditions we consistently reached 100% on-target cleavage, while the off-target activity, measured as the percentage of white colonies (TRP1$^+$/ADE2$^+$) on reporter plates, increased in accordance with the distance of the mismatched base from the PAM sequence, as expected (FIG. 2). For the two most PAM-distal off-targets (off3 and off4), SpCas9 was completely unable to discriminate between the matching and the two mismatched sequences (FIG. 2).

Considering these results, SpCas9 variants were screened using the yACMO-off4 strain, containing the strongest off-target sequence, in order to select mutants with a marked increase in fidelity.

Yeast-Based Screening for High-Specificity SpCas9 Variants

Figure 3:
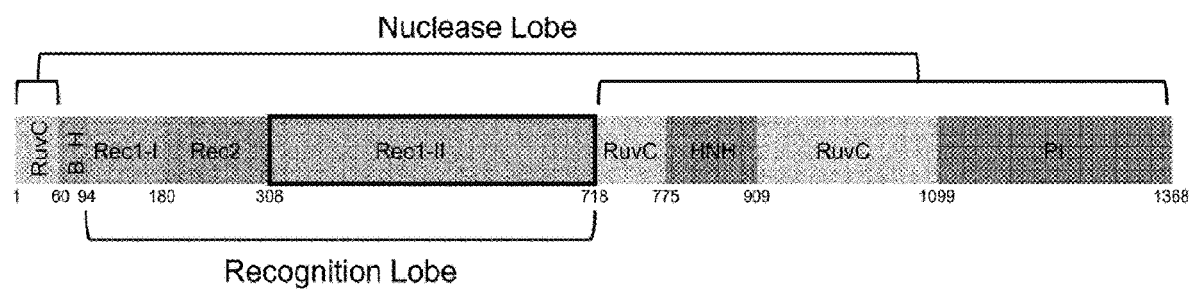
FIG. 3. Selection of a target domain for random library generation. Schematics of SpCas9 domains. The Rec1-II domain (highlighted) is part of the alpha helical recognition lobe. BH: bridge helix.

Differently from published studies (Slaymaker I M et al., Science. 2016, 351(6268):84-8; Kleinstiver B P et al., Nature. 2016, 529(7587):490-5), the inventors believed that an unbiased approach could lead to the isolation of non-trivial amino acid substitution increasing the likelihood to obtain a SpCas9 variant with higher fidelity. To find a suitable target for random mutagenesis, the available structural data were analysed to identify which SpCas9 domain could be more involved in the formation of such kind of interactions. The nuclease lobe of Cas9 was excluded from this analysis, since it contains the two catalytic sites that must be preserved to maintain cleavage activity. The recognition lobe, containing the Rec1, Rec2 and the bridge helix domains, has been reported to make several contacts with the gRNA:DNA duplex. In addition, the recognition lobe as a whole is one of the least conserved regions across all the three Cas9 families belonging to type II CRISPR systems, indicating a high degree of sequence plasticity. The bridge helix, on the contrary, is one of the most conserved regions among different Cas9 orthologues, suggesting that its sequence is particularly important for nuclease function. The Rec1-Rec2 region spans more than 600 amino acids, a dimension not suitable for random mutagenesis, but the majority of interacting residues are located in the last portion of the Rec1-II domain, approximately between residue 400 and 700 (FIG. 3). A library of REC1-II variants, generated by error-prone PCR to contain approximately 4-5 mutations per molecule, was directly assembled in the yACMO-off4 reporter yeast strain exploiting homologous recombination between the mutagenized REC1-II fragments, containing appropriate homology arms, and a plasmid expressing a galactose-inducible SpCas9 in which the same region had been previously removed. The overall screening workflow is schematized in FIG. 4a. After co-transformation and an overnight recovery incubation in SDlu medium to allow the repair of the Cas9-encoding plasmid by homologous recombination and the selection for transformed cells, cultures were induced for 5 hours with galactose to express SpCas9 and then plated on several SDluta$_5$ reporter plates. The induction time was shortened, with respect to previous experiments, to obtain variants that maintained high on-target activity since we observed that wild-type SpCas9 can fully cleave the on-target sequence in this restricted time span (data not shown). Two days later multiple colonies were obtained and the red ones were streaked on new reporter plates containing galactose instead of dextrose to reactivate SpCas9 expression and to keep it constantly switched on to exacerbate any off-target effect. After 48 hours, plasmids were recovered from the red-most streaks and after amplification in bacteria were Sanger-sequenced to identify the mutations introduced in the REC1-II domain. Several amino acidic substitutions were identified, some of which were present more than once in the mutants' pool in combination with groups of different mutations. Of note, it is likely that mutants containing the same set of variations represent clones deriving from the same original cell that replicated during the recovery incubation. However, given the diversity of substitutions obtained, this phenomenon did not affect the results of the screening. A re-challenging experiment was then performed in the yACMO-off4 strain with each isolated variant in order to measure more precisely its cleavage activity, discard those that did not efficiently cut their target compared to wild-type SpCas9 and rank the remaining ones according to the latter parameter and their ability to discriminate off-target sites (FIG. 4b). To further validate the results of the screening, the specificity of one of the obtained variants (C13 variant) was evaluated more in detail by challenging all four yACMO reporter strains. After 24 hours of Cas9 expression, the quantification of white and red colonies on reporter plates showed significantly reduced off-target activity when compared to wild-type SpCas9 (compare FIG. 4c and FIG. 2).

Optimization of High-Fidelity SpCas9 Variants in Mammalian Cells

A pool of substitutions belonging to best performing variants isolated from the yeast screening according both to on-target cleavage efficiency and reduction of unspecific activity was selected. To obtain a significant increase in fidelity with respect to the identified mutants a hierarchical combination of these mutations was attempted, since it was expected that some of the substitutions in each randomly generated variant may have been neutral or detrimental. The relative position of each substitution and the sgRNA:DNA duplex, according to available structural data, was employed as a first filtering criterion, identifying a first subset of mutations. In addition, the attention was drawn to a conformational cluster of substitutions located at the end of the REC1-II domain which is in contact with the more PAM-distal part of the target DNA sequence (nt. 17-20). Hence, mutations belonging to this cluster were selected even though no interaction with the sgRNA:DNA duplex has been previously reported. In particular, it was decided to add the mutations sequentially starting from the K526E mutant, that performed particularly well in the yeast assay (FIG. 4c). Notably, the K526E mutation is included in the aforementioned Rec1-II domain (FIG. 3).

Figure 5:
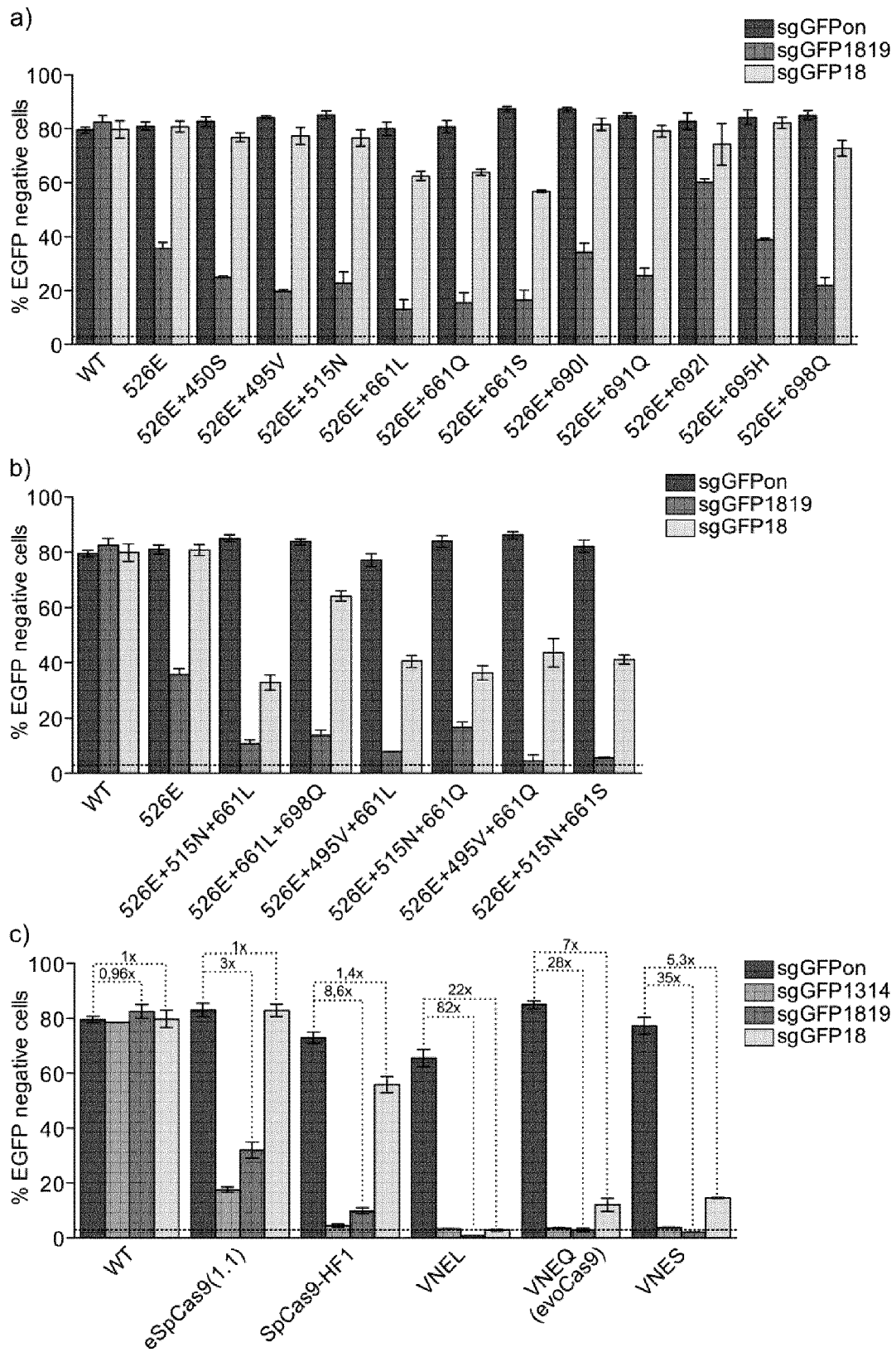
FIG. 5. Selection of optimized SpCas9 variants in mammalian cells. 293 cells stably expressing EGFP were transfected with single and double (a) as well as triple (b) mutants generated by the hierarchical combination of mutations obtained from the best performing yeast-isolated variants together with an on-target sgRNA (sgGFPon) or each of the mismatched guides. Loss of EGFP fluorescence was measured by FACS analysis at 7 days post transfection. (c) Side-by-side comparison of the best generated variants with previously published mutants. The 293 cell line EGFP knockout assay was used to assess the specificity of the top isolated variants (VNEL, VNEQ and VNES variants) and to compare their performance with previously published high-fidelity mutants. Loss of EGFP fluorescence was measured by FACS analysis at 7 days post transfection. sgGFP1314 contains mismatches in position 13&14 from the PAM of the spacer sequence; sgGFP1819 contains mismatches in positions 18&19; sgGFP18 contains a single mismatch in position 18. Dotted lines indicate on/off target ratios calculated for the indicated on/off couples. Dashed lines indicate the background loss of EGFP fluorescence. Error bars represent s.e.m. for n≥2.

Using a reporter cell line stably expressing EGFP (293multiGFP), the on-target activity (sgGFPon) of double mutants was tested by measuring the loss of fluorescence induced by frameshift mutations into the EGFP coding sequence. In parallel, their ability to avoid the cleavage of the same site after the introduction into the sgRNAs of one or two mismatched bases in positions distal from the PAM trinucleotide (position 18 for sgGFP18 and positions 18-19 for sgGFP1819) was evaluated. Wild-type SpCas9 was not able to discriminate these surrogate off-target sequences, as confirmed by the observation that it cleaved the target sequence with equal efficiency when guided by both matched and mismatched sgRNAs, producing the same reduction in the percentage of EGFP$^+$ cells (FIG. 5a). After a first round of selection, the top performing substitutions were combined into triple mutants that were used to repeat the challenging of the EGFP reporter cell line (FIG. 5b). A last round of selection was then performed after generating a quadruple mutant by combining the best substitutions of the previous round (VNEL variant). In addition, another sgRNA containing two mismatches in a more PAM-proximal region (positions 13 and 14, sgGFP1314) was tested to verify that the observed increase in fidelity of the VNEL variant was conserved for mutations spanning the whole spacer sequence. The VNEL variant induced little or no loss of EGFP fluorescence for all mismatched guide RNAs, a result that was particularly striking for the sgRNA containing a single substitution in position 18 from the PAM (sgGFP18). On the other hand, this strong increase in specificity produced a small albeit measurable decrease in on-target activity (~20% loss, FIG. 5c). In order to address this issue, two alternative derivatives of the VNEL variant (the VNEQ and VNES variants) were generated by rational design and tested using the same EGFP knockout assay. As expected, a complete restoration of on-target cleavage efficiency was observed, paralleled with a small increase in off-target activity. Overall the VNEQ variant mutant showed the best on/off target ratio (FIG. 5c).

Figure 6:
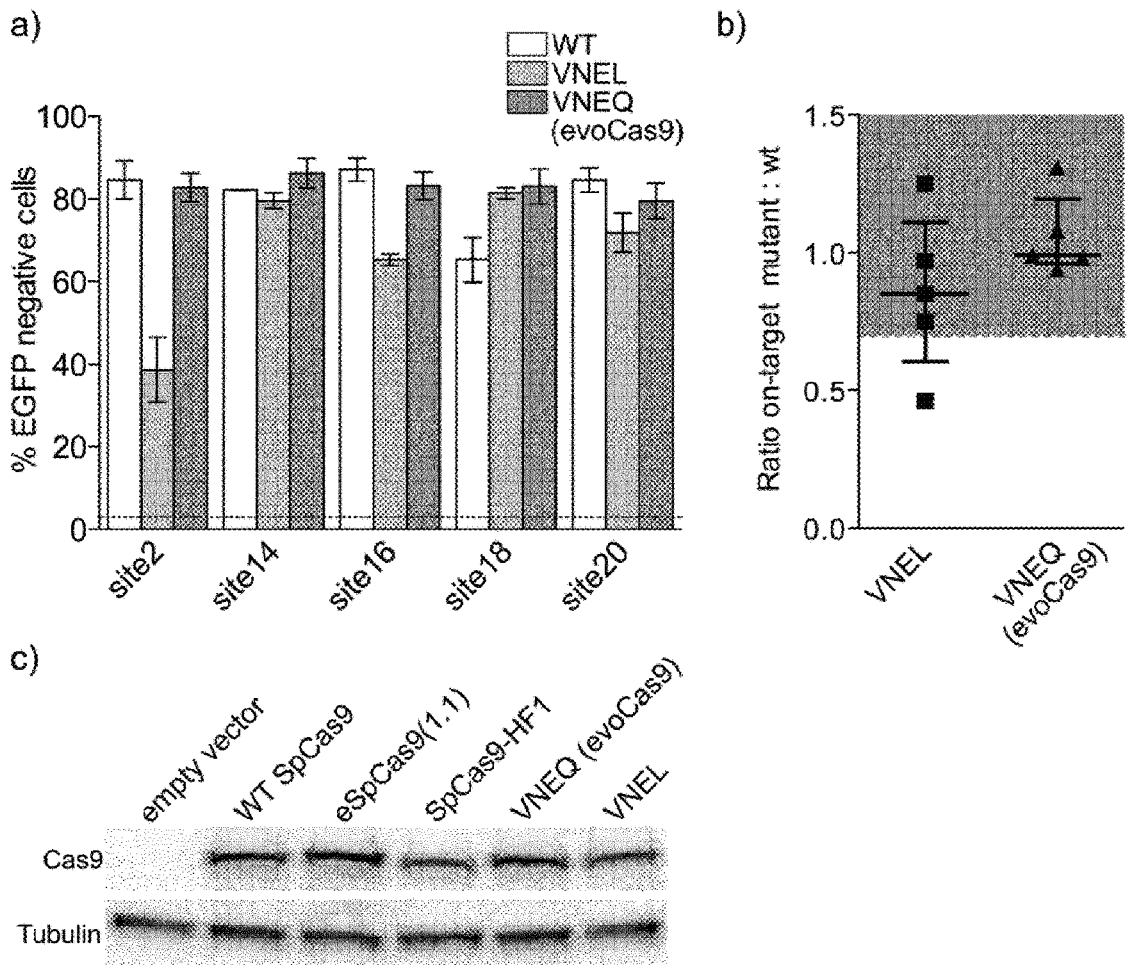
FIG. 6. evoCas9 on-target activity against EGFP. (a) evoCas9 activity against EGFP loci. 293 cells stably expressing EGFP were transfected with wt SpCas9, evoCas9 (VNEQ) or the VNEL variant together with sgRNAs targeting different regions of the EGFP coding sequence. Loss of EGFP fluorescence was measured by FACS analysis at 7 days post transfection. Dashed lines indicate the background loss of EGFP fluorescence. Error bars represent s.e.m. for n≥2. (b) Ratio of on-target activity of evoCas9 and the VNEL variant to wild-type SpCas9 calculated on EGFP loci. The median and interquartile range are shown. A level of on-target activity above 70% of the wt protein is indicated by the shaded area. (c) evoCas9 intracellular expression. Representative western blot of lysates from 293T cells transfected with wt SpCas9, evoCas9 or the other high-fidelity variants. Tubulin was used as a loading control. SpCas9 is detected using an anti-FLAG antibody.

Side-by-side comparison of the quadruple mutants (VNEL, VNEQ, VNES variants) with previously published high-fidelity variants SpCas9-HF1 and eSpCas9(1.1) using the above described EGFP reporter cell line, revealed a marked increase in fidelity which was particularly evident using the sgRNA containing a single mismatch in position 18. For this particular surrogate off-target, approximately a 17 to 4-fold absolute reduction in unspecific cleavage was measured when comparing the VNEL, VNEQ and VNES variants with SpCas9-HF1, which according to the present experiments was already discriminating mismatched sites much better than eSpCas9(1.1) (FIG. 5c). This observation was further confirmed by analyzing the on-/off-target ratios of the different SpCas9 variants calculated for the two strongest surrogate off-targets (sgGFP1819 and sgGFP18) (compare dotted lines in FIG. 5c). Next, the on-target activity of the VNEL and VNEQ variants was assessed more in detail by targeting different regions of the EGFP coding sequence, using the 293multiGFP reporter cell line and measuring the loss of EGFP fluorescence. The VNES variant excluded from the analysis since it behaved similarly to the VNEQ mutant. In accordance with previous results (FIG. 5c), we observed wild-type levels of activity for VNEQ, while VNEL was slightly underperforming at some of the sites, with a significant drop in activity for one of the tested loci (FIGS. 6a and 6b). To rule out the possibility that the different cleavage behaviour measured towards on- and off-target sites was due to an alteration of the intracellular levels of the SpCas9 variants, the protein levels of wild-type SpCas9, VNEL and VNEQ, as well as of the two previously published high-fidelity variants eSpCas9(1.1) and SpCas9-HF1 were analyzed in 293T cells transfected with equal amounts of expression plasmids. As clearly shown by the results (FIG. 6c), no major differences in protein levels were observed. Given these results, the VNEQ variant was further characterized, since among the mutants here analyzed it retained near wild-type levels of activity and reduced drastically the cleavage of non-matching sequences in the EGFP-disruption cellular model. The VNEQ mutant was named evoCas9 (evolved Cas9).

evoCas9 Activity Towards Endogenous Loci

Figure 7:
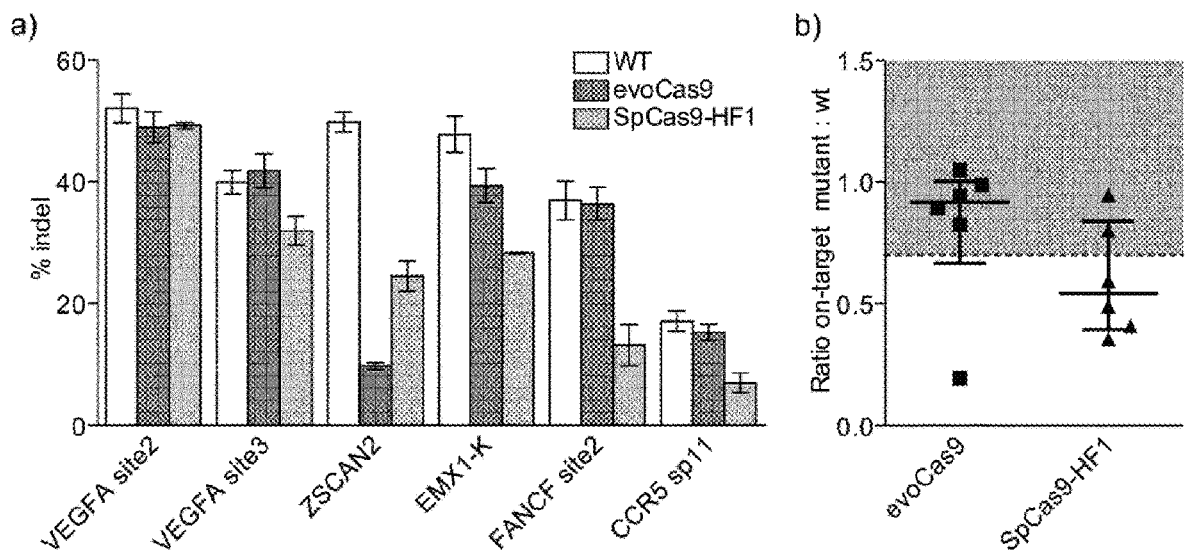
FIG. 7. evoCas9 activity on endogenous loci. (a) wt SpCas9, evoCas9 and SpCas9-HF1 activity towards endogenous loci were compared by transfecting 293T cells and by measuring indel formation at 7 days post-transfection using the TIDE tool. (b) Ratio of on-target activity of evoCas9 and SpCas9-HF1 to wild-type SpCas9 calculated on endogenous loci. The median and interquartile range are shown. A level of on-target activity above 70% of the wt protein is indicated in by the shaded area. Error bars represent s.e.m. for n=2.

The above findings were then further validated by targeting endogenous loci. A group of previously tested genomic target sites was thus selected in order to compare the cleavage activity of evoCas9 with the one of wild-type SpCas9 at each locus. In addition, SpCas9-HF1 was also introduced in the comparison, as a further benchmark. After transfection in 293T cells of each SpCas9 variant together with sgRNAs targeting the different loci, indel formation was analysed by using the Tracking of Indels by Decomposition (TIDE) software package on Sanger-sequenced amplicons relative to each target site (Brinkman E K et al., Nucleic Acids Res. 2014, 42(22):e168). For the majority of the loci, we did not observe any major difference in targeting efficiency between wild-type SpCas9 and evoCas9, with the latter being in general slightly less active with an overall mean activity which is 80% that of the wild-type protein (FIG. 7a and FIG. 7b). For one target site, the ZSCAN2 locus, we observed very poor cleavage efficiency, with no obvious explanations for such behaviour (FIG. 7a). The SpCas9-HF1 variant showed an overall lower cleavage efficiency, with a global mean activity which is 60% compared to the wild-type (FIG. 7a and FIG. 7b). This is not in accordance with previously published observations (Kleinstiver B P et al., Nature. 2016, 529(7587):490-5) and it is possible to speculate that this discrepancy could be due to the different experimental procedures. These data demonstrate that evoCas9 retains near-wild type levels of on-target activity against a panel of endogenous loci, outcompeting the previously reported SpCas9-HF1 variant, in the experimental conditions tested.

Evaluation of evoCas9 Off-Target Activity

Figure 8:
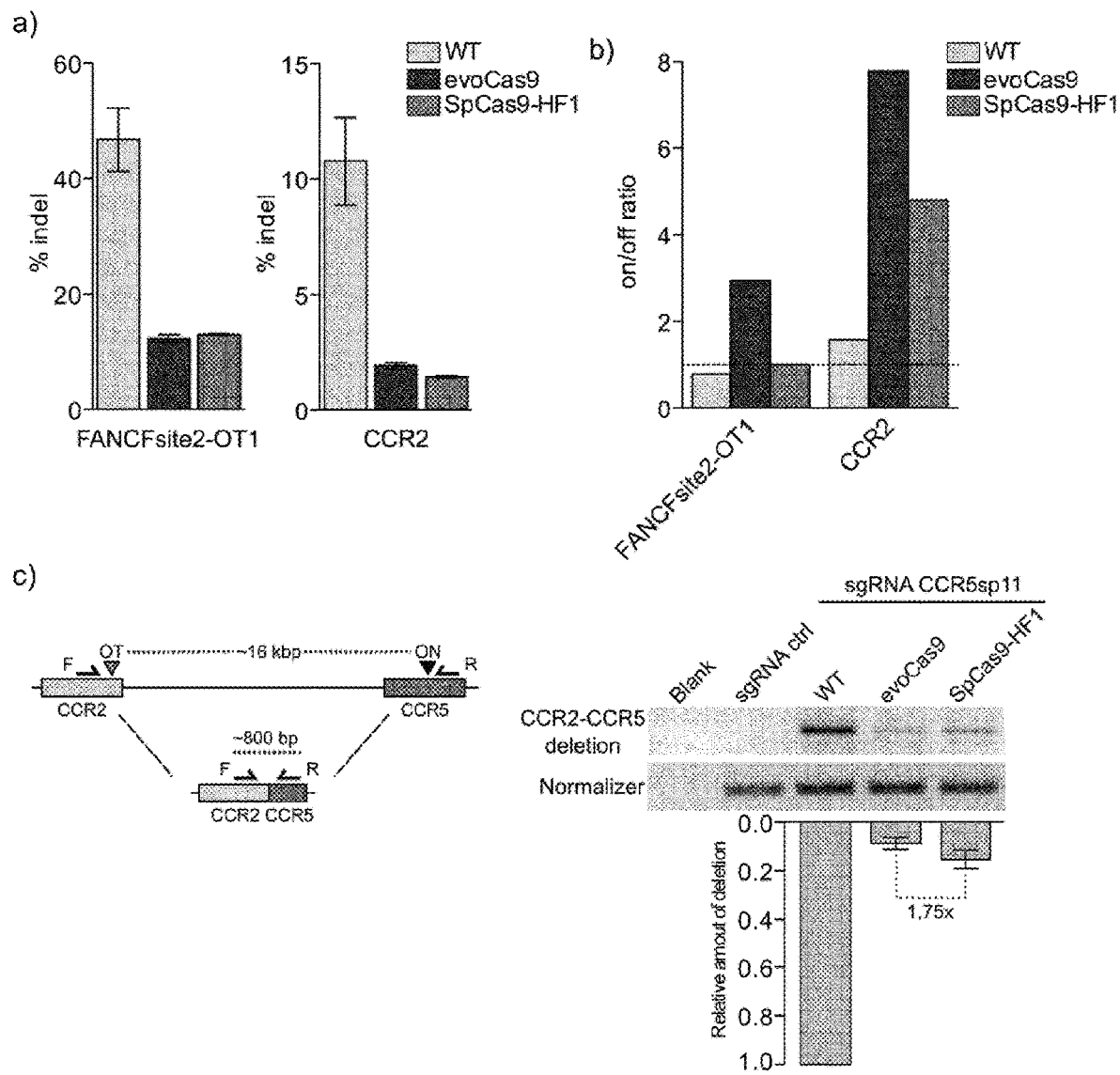
FIG. 8. Side-by-side comparison of evoCas9 and SpCas9-HF1 specificity. (a) Off-target activity of evoCas9 on selected loci. 293T cells were transfected with wt SpCas9, evoCas9 or SpCas9-HF1 together with sgRNAs targeting the FANCF site 2 or the CCR5 sp11 loci. Indel formation at two previously validated off-target sites was evaluated at 7 days post transfection using the TIDE tool. Error bars represent s.e.m. for n=2. (b) On/off ratios calculated from the mean indel percentages obtained in (a). Dashed lines indicates and on/off ration equal to 1. (c) Schematic representation of the CCR5 locus and its off-target site in the highly homologous CCR2 gene. Simultaneous cleavage of the two sites generates a chromosomal deletion of approximately 16 kb. Semi-quantitative PCR was performed on genomic DNA of 293T cells transfected with wt SpCas9, evoCas9 or SpCas9-HF1 and the CCR5 guide RNA to assess the amount of chromosomal deletion generated in each condition. The FANCF locus was used as an internal normalizer. The amount of deletion was quantified using densitometry with ImageJ. Error bars represent s.e.m. for n=2.

Together with the activity towards on-target sites, evoCas9 specificity was measured by verifying the editing rate at two previously validated off-target sites associated with the editing at two loci: FANCF site 2 and CCR5 sp11. Cas9 editing of these loci generates interests since the FANCF site 2-associated off-target was one of the few non-repetitive sites that SpCas9-HF1 was unable to discriminate from the specific on-target site, while the CCR5sp11 locus, which has a value for its therapeutic application in AIDS treatment, correlates with off-target cleavage of the highly homologous CCR2 gene. After transient transfection in 293T cells, indel formation at these two off-target loci was measured using TIDE revealing a significant decrease of cleavage in cells expressing evoCas9 when compared to wild-type SpCas9-transfected cells (FIG. 8a). In addition, the calculation of the on/off-target ratios for wild-type SpCas9, evoCas9 and SpCas9-HF1 confirmed that the variant of the invention was able to outperform its competitors at these two loci (FIG. 8b). The concerted cleavage of the CCR5sp11 locus and its off-target in the CCR2 gene generates a chromosomal deletion of approximately 16 kilobases (schematized in FIG. 8c). The frequency of this chromosomal rearrangement was measured by semi-quantitative PCR in cells transfected with wild-type SpCas9, evoCas9 or SpCas9-HF1 together with the sgRNA targeting the CCR5 locus. While the translocation event was particularly evident in cells edited by wild-type SpCas9, a strong reduction in the amount of deletion to barely detectable levels was observed both in presence of SpCas9-HF1 and evoCas9, with the latter further reducing the measured deletion by almost two-fold with respect to the former (FIG. 8c).

Figure 9:
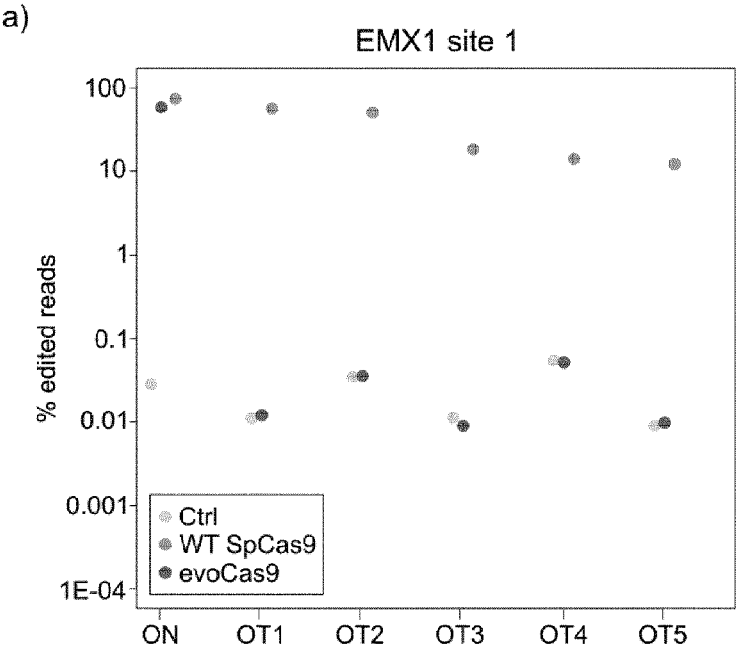
FIG. 9. Validation of evoCas9 specificity by targeted deep-sequencing. Targeted deep-seq of previously validated off-target sites relative to the EMX1 site 1 locus (a) and the VEGFA site 3 locus (b) was performed on genomic DNA of 293T cells expressing either wt Spcas9 or evoCas9 together with each specific sgRNA. Cells not expressing Cas9 were sequenced to determine background indel levels. Genomic DNA from three biological replicates was mixed before library preparation.
Figure 9:
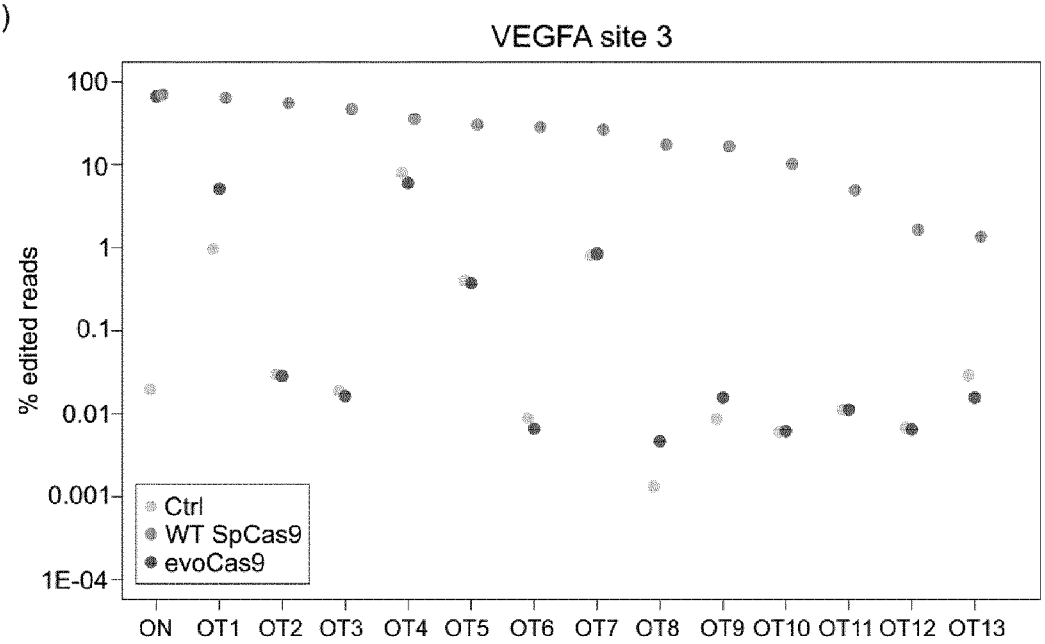

Next the ability of evoCas9 to avoid unwanted genomic cleavages was investigated by performing targeted deep sequencing on a selected set of off-target sites associated with editing at the VEGFA site 3 and EMX1-K genomic sites. All the chosen sites were previously shown to be edited together with the on-target locus (Kleinstiver B P, et al., Nature. 2015, 523(7561):481-5). The advantage of the amplicon-seq approach lies in the possibility to simultaneously measure several targets with high coverage in order to detect even low abundant editing events. Analysis of sequencing data demonstrated that, while retaining high on-target activity on both genomic loci, evoCas9 was characterized by background levels of editing at the majority of the tested off-target sites (FIGS. 9a and 9b). The first VEGFA site 3 off-target site (VEGFA3-OT1) was the only locus where the evoCas9 editing activity appeared above the background (FIG. 9b). However, it must be considered that the same locus is edited almost as the on-target site by wild-type SpCas9 and that the previously reported SpCas9-HF1 variant was unable to completely suppress the unspecific cleavage of this sequence (Kleinstiver B P et al. Nature, 2016, 529(7587):490-5). It has been speculated that this results can be explained by the highly repetitive nature of this particular locus. For four VEGFA site 3 off-target sites (VEGFA3-OT1, -OT4, -OT5, -OT7) significantly higher background editing rates were revealed (FIG. 9b) probably due to peculiar characteristics of the local chromatin that is more fragile and thus prone to accumulate mutations.

Altogether, this data indicates that evoCas9 significantly decreases unwanted genomic cleavages to undetectable levels for the majority of the tested off-target sites. In addition, side-by-side comparisons with the previously published SpCas9-HF1 variant for selected off-target sites demonstrated an increased ability to discriminate mismatched sites.

Genome-Wide Specificity of evoCas9

Figure 10:
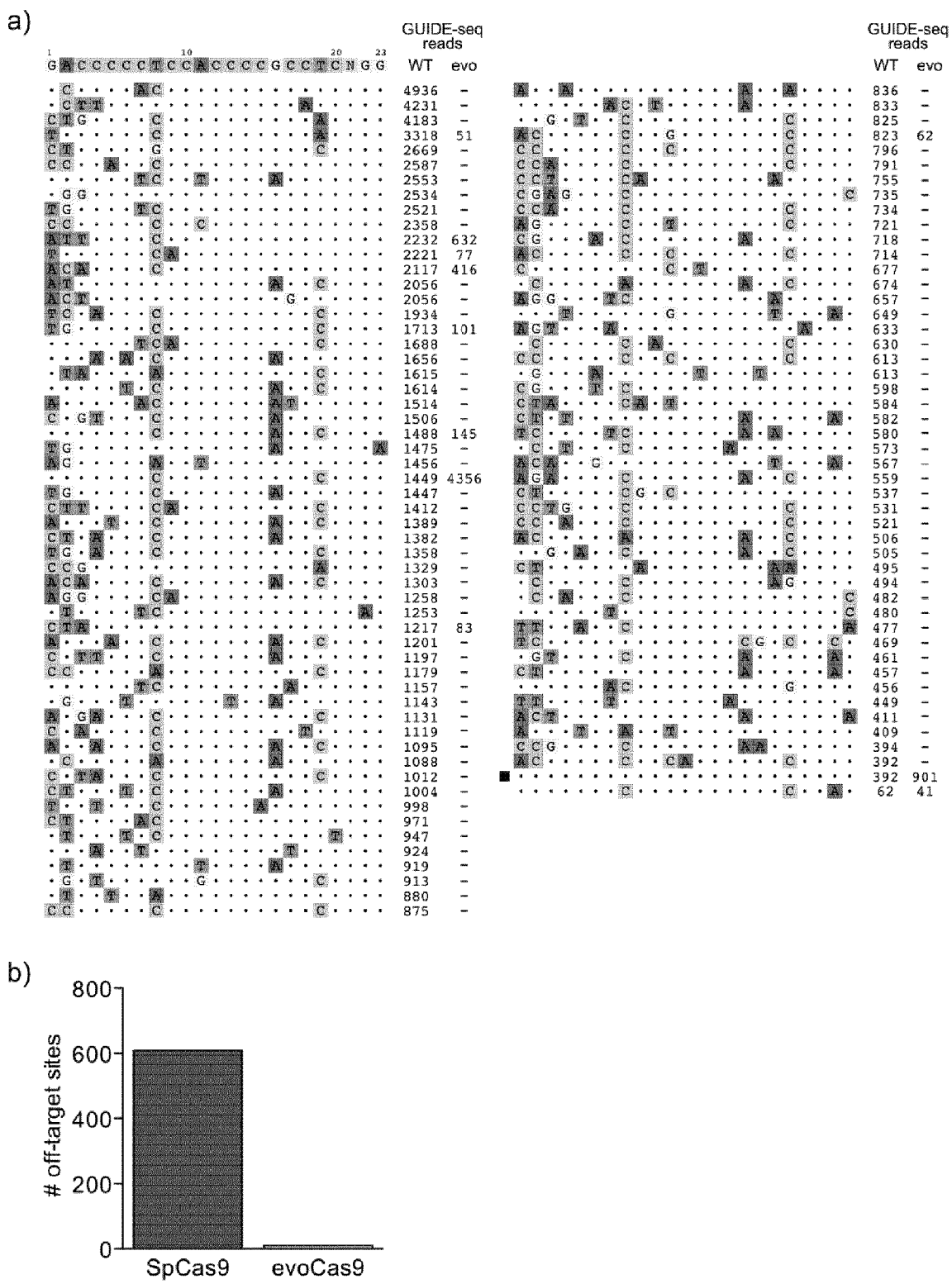
FIG. 10. Genome-wide specificity of evoCas9. (a) GUIDE-seq analysis of the off-target sites relative to the VEGFA site 2 locus performed for both wt SpCas9 and evoCas9 in 293T cells. The black square indicates the on-target site. (b) Total number of detected off-target sites for wt SpCas9 and evoCas9. Genomic DNA from three biological replicates was mixed before library preparation.

The analysis of evoCas9 off-target activity at a genome-wide level was extended by using the previously established GUIDE-seq technique (Tsai S Q et al., Nat Biotechnol. 2015, 33(2):187-97). This approach is based on the integration of a 34 bp oligonucleotide tag into sites which have been cut by Cas9 in order to allow their capture for library preparation and next-generation sequencing. In this way, it is possible to identify in an unbiased fashion a collection of novel genomic sites associated with a particular guide RNA that are unspecifically targeted by Cas9. GUIDE-seq analysis was performed to analyze the off-target sites associated with the editing of VEGFA site 2 locus, which is highly repetitive, and has been shown to generate numerous unwanted cleavages into the cellular genome. Additionally, past reports (Kleinstiver B P et al., Nature. 2016, 529(7587):490-5) indicated that some of the detected off-targets were still cleaved by the high-fidelity SpCas9-HF1 variant. GUIDE-seq libraries were thus generated from genomic DNA of 293T cells transfected either with wild-type SpCas9 or evoCas9, together with the VEGFA site 2 sgRNA and the bait double stranded oligonucleotide. Sequencing data was analysed using an open source software pipeline (Tsai S Q et al., Nat Biotechnol. 2016, 34(5):483) revealing 600 different off-target sites for wild-type SpCas9 characterized by 7 or less mismatches with the on-target sequence (FIGS. 10a and 10b). Of note, approximately 100 of these off-target sequences were edited more efficiently that the on-target site, according to the number of reads obtained after GUIDE-seq analysis that have been reported to be a good proxy of the actual cleavage activity at each specific site (Tsai S Q et al., Nat Biotechnol. 2015, 33(2):187-97) (FIG. 10a). When the same analysis was performed on evoCas9 samples, a total of only 10 sites were detected, the majority of which shared high similarity with the on-target and were characterized by less than five mismatches with the VEGFA site 2 locus (FIG. 10a). Only one off-target emerged from the analysis showing high frequency cleavage (more than the on-target) by evoCas9 and this was probably due to the particular nature of this sequence that differed by only two nucleotides from the intended target and contained two uninterrupted stretches of cytosines at the level of each mismatch (FIG. 10a), possibly allowing the formation of bulge sites to accommodate the non-matching nucleotides.

Overall, the above GUIDE-seq analysis demonstrated that evoCas9 retains very high-specificity at the genome-wide level even when tested using a repetitive target sequence characterized by multiple off-targets into the cellular genome.

Specificity of an Evo-dCas9-Based Transcriptional Activator

Figure 11:
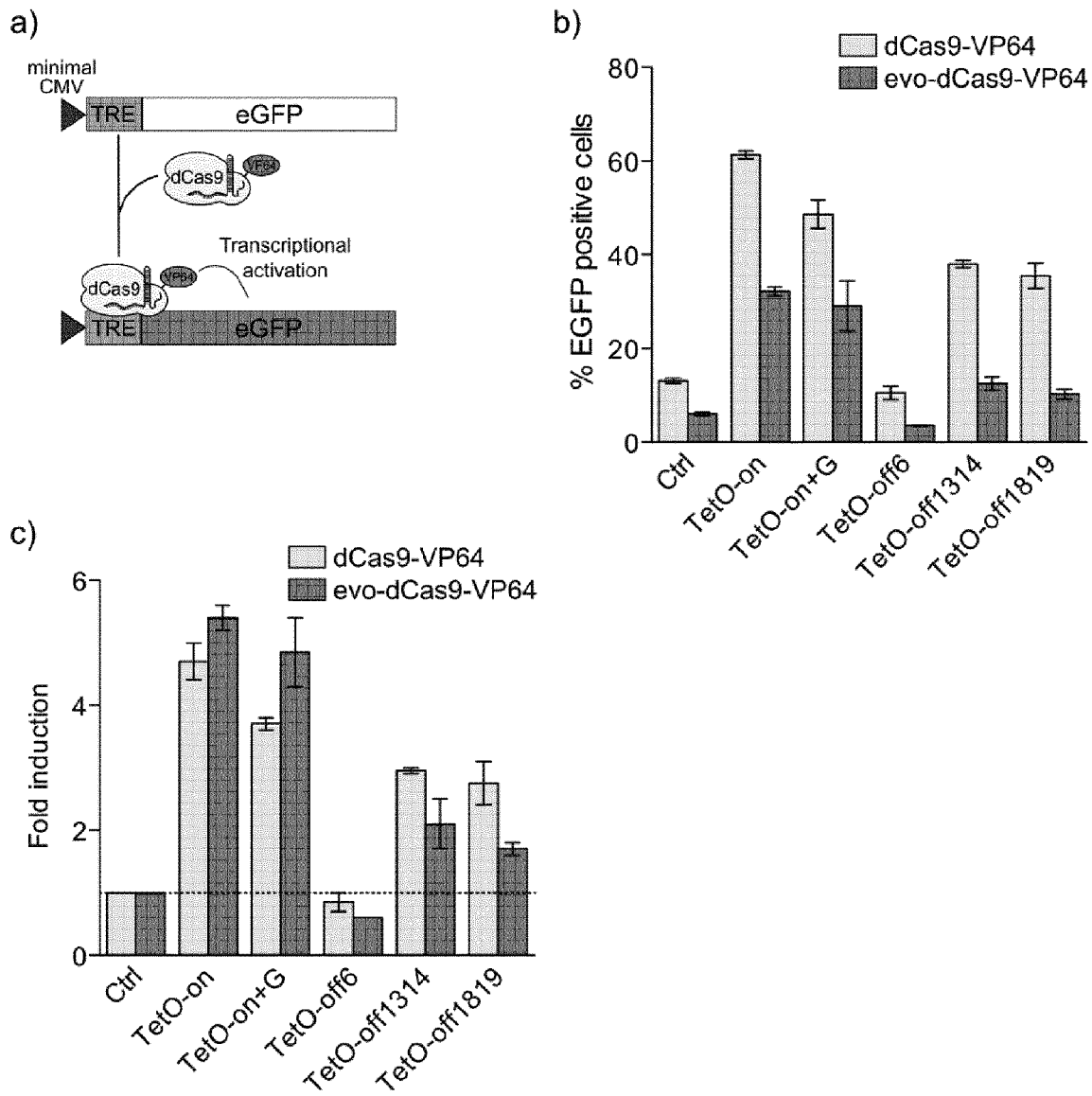
FIG. 11. evo-dCas9 transcriptional activation. (a) Schematic representation of the Tet Responsive Element (TRE)-EGFP based transcriptional activator reporter. Upon binding of dCas9-VP64 to TetO repeats EGFP expression is activated. (b) EGFP activation was measured in 293T cells transfected with dCas9 or evo-dCas9 based transcriptional activators together with matching sgRNAs (both with or without a 5' mismatched G) or mismatched guides. TetO-off6 contains a mismatch in position 6 from the PAM, TetO-off1314 contains two mismatches in position 13-14 and TetO-off1819 contains two mismatches in position 18-19. (c) Fold activation of EGFP expression with respect to the non-targeting control calculated from the data in (b). Error bars represent s.e.m. for n=2. EGFP expression was measured by FACS analysis 2 days post-transfection.

An alternative application for Cas9, independent from its nuclease activity, is the generation of RNA-guided transcriptional activators by fusing a catalytically inactive version of Cas9 (dCas9) to various protein domains able to stimulate transcription. A VP64-based transcriptional activator was engineered using a catalytically inactive mutant of evoCas9 (evo-dCas9) and tested side-by-side with a wild-type dCas9-VP64 activator. The transcriptional activation was tested by using a reporter system based on an inducible EGFP-expression vector regulated by a TetR-based trans-activator through Tet operators elements integrated within a minimal CMV promoter. The Tet trans-activator was substituted with the Cas9-based transcriptional activator guided by a sgRNA targeting the repeated Tet operator sequences (FIG. 11a). Two different on-target sgRNAs differing only for the presence or the absence of an extra 5'-G nucleotide were designed towards the Tet operator locus of the reporter plasmid, plus three additional mismatched guides based on the same on-target sequence, bearing either one or two mutations in different positions along the spacer sequence. Lower absolute levels of EGFP expression were observed with evo-dCas9-VP64 compared to dCas9-VP64 for both matching and mismatched guide RNAs, suggesting stronger binding to the target DNA by wild-type dCas9 (FIG. 11b). However, the on-target fold activation relative to the control sgRNA was similar for both wild-type dCas9 and evo-dCas9, due to the lower background activation observed with evo-dCas9. This result is probably due to lower propensity of evo-Cas9 to bind DNA unspecifically (FIG. 11c). Interestingly, the increased specificity showed by evo-dCas9-VP64 was modest when compared with dCas9-VP64, suggesting that evoCas9 binds to mismatched targets, even though less efficiently, but is then unable to complete the cleavage reaction (FIG. 11c). Overall, these results indicate that evoCas9 can be exploited to build a transcriptional regulator characterized by lower background activation, albeit less absolute activation potency, and slightly increased activation fidelity.

Long-Term Specificity of evoCas9

Figure 12:
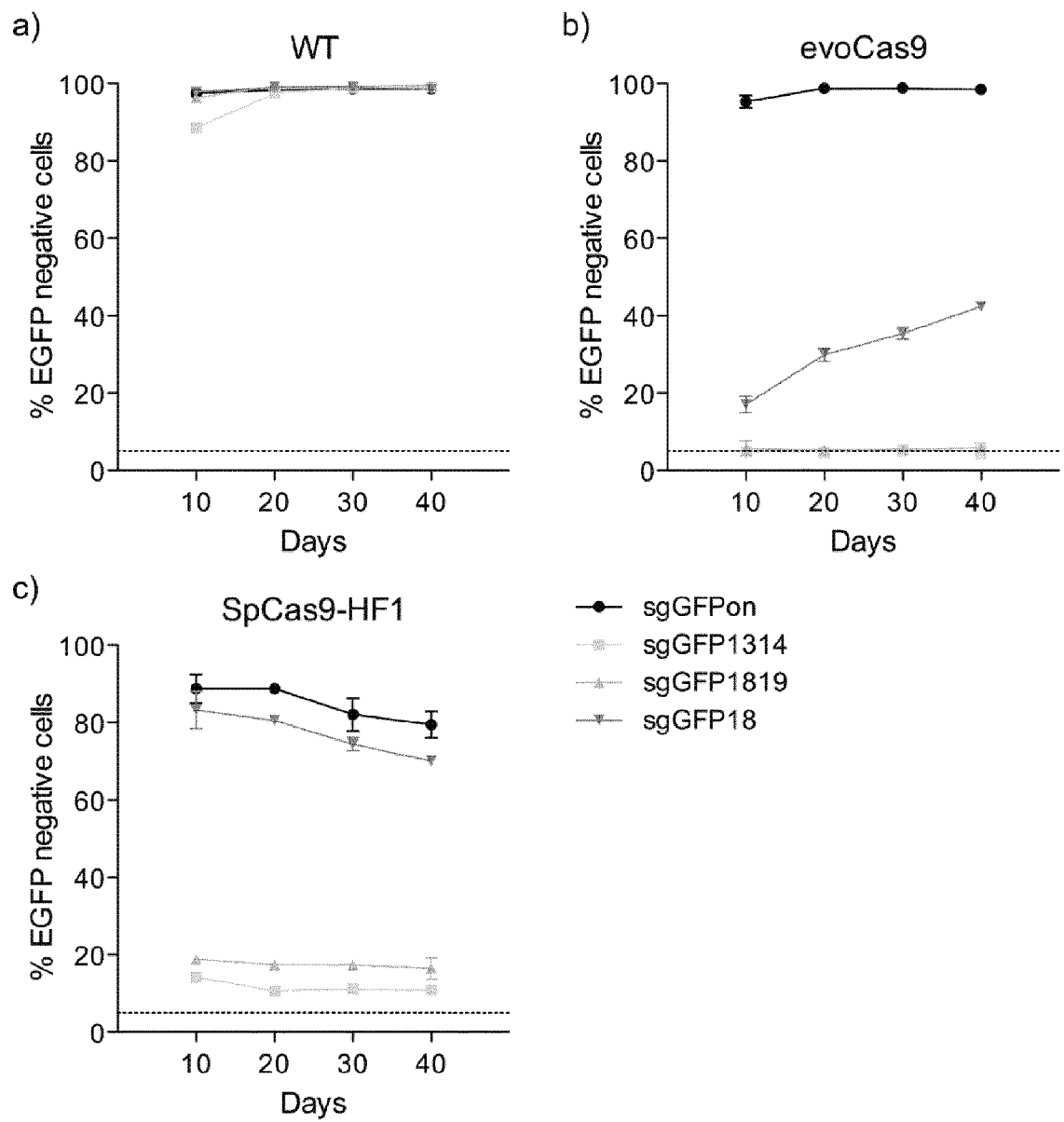
FIG. 12. Long-term specificity of evoCas9. SpCas9 (a), evoCas9 (b) and SpCas9-HF1 (c) were stably expressed through lentiviral delivery in 293T cells stably expressing EGFP. Each lentiviral vector carried an on-target sgRNA towards the EGFP coding sequence or different mismatched guides presented in FIG. 5. EGFP knockout was evaluated by FACS analysis at the time points indicated in the graphs. Transduced cells were cultured in puromycin selection medium. Error bars represent s.e.m. for n=2.

Since the permanent expression of Cas9 into cells has been associated with increased off-targeting activity, an important issue that had to be investigated was the long-term behaviour of evoCas9 into cells. To address this point, lentiviral particles were generated in order to obtain stable expression of wild-type SpCas9, evoCas9 or SpCas9-HF1 together with an sgRNA of interest. To exploit a cellular EGFP-knockout model similar to the one previously employed to screen for high-specificity variants the experiments were conducted using the same set of sgRNAs directed towards the EGFP coding sequence, either perfectly matching the target locus or containing one or more mismatches in different positions of the spacer sequence, thus acting as surrogate off-targets. The reporter cell line was transduced with equal amounts of the different lentiviral vectors and the cultures were selected throughout the entire period of the experiments to isolate the transduced population and avoid the possible dilution of editing events in time produced by the loss of edited cells or the reduced fitness of transduced cells. Similarly to what observed in transient transfection experiments the decrease of EGFP fluorescence at different time points revealed that wild-type SpCas9 cuts the target sequence with similar efficacy either with the perfectly matching sgRNA or the mismatched ones (see FIG. 12a and FIG. 5c). On the contrary, both evoCas9 and SpCas9-HF1 did not cleave EGFP efficiently using the sgGFP1314 and sgGFP1819 sgRNAs, both containing double mismatches (FIG. 12b-c). Of note, while loss of fluorescence was at background levels for evoCas9 samples at all time points, a measurable number of EGFP-negative cells that remained constant over time was present in the cultures transduced with SpCas9-HF1-expressing vectors (FIG. 12c). In addition, when considering the strongest surrogate off-target, sgGFP18, containing a single mismatch in a PAM-distal position, the behaviour of the two variants significantly differed: while SpCas9-HF1 was not able to correctly discriminate between matching and mismatched sgRNA and cleaved the target locus with similar efficiency, evoCas9 showed an increasing trend of loss of fluorescent cells that reached less than half the level of the on-target knockout at 40 days post-transduction (FIGS. 12b-c). These data suggest that, with a careful selection of guide RNAs, the high-specificity Cas9 variant of the invention, evoCas9, allows long-term expression of the nuclease with limited or no unwanted cleavages in the cellular genome.

Materials and Methods

Plasmids and Constructs.

The plasmid p415-GalL-Cas9-CYC1t was used to express Cas9 in yeast (obtained from Addgene, #43804) (Di Carlo J E, et al., Nucleic Acids Res. 2013, 41(7):4336-43). To allow the precise removal of the Rec1-II domain by restriction digest, synonymous mutations were generated through PCR in order to introduce two restriction sites, NcoI and NheI, upstream and downstream of the Rec1-II domain, respectively (for primers, see Appendix Table 2). The expression cassette for the sgRNA was obtained from the p426-SNR52p-gRNA.CAN1.Y-SUP4t plasmid (obtained from Addgene, #43803) (Di Carlo J E, et al., Nucleic Acids Res. 2013, 41(7):4336-43). In order to swap the original spacer sequence with the desired target, an assembly-PCR based strategy was adopted. The 5' portion of the sgRNA expression cassette was PCR-amplified using the T3 forward primer (annealing before the SNR52 promoter) and a reverse primer annealing immediately upstream of the spacer sequence and containing a 5' overhang corresponding to the desired on-target sequence (see Appendix Table 2). The same was done for the 3' fragment of the sgRNA, using the primer T7 reverse primer and a forward primer annealing immediately after the spacer sequence and containing a 5' overhang antiparallel to one previously mentioned. The assembly reaction to obtain the gRNA cassette was prepared by mixing both PCR amplicons and performing a single step of denaturation, annealing and extension, followed by an exponential amplification using only the T3 and T7 external primers. The resulting fragment was then gel purified and blunt-end cloned into pRS316 (ATCC), a low copy number centromeric plasmid carrying a URA3 yeast selectable marker, pre-digested with SacII/XhoI and blunted, generating the pRS316-SNR52p-gRNA.ON-SUP4t plasmid.

For the expression of SpCas9 in mammalian cells we employed a pX330-U6-Chimeric_BB-CBh-hSpCas9 (obtained from Addgene, #42230) (Cong L et al., Science. 2013, 339(6121):819-23) derived plasmid, were the sgRNA coding cassette has been removed, pX-Cas9. The SpCas9 coding sequence has been human codon optimized and is regulated by a CBh promoter. In addition, two nuclear localization signals (NLS) have been added to the N- and C-terminus of SpCas9 to allow nuclear import and a triple FLAG is positioned at the N-terminal end of the protein to facilitate detection. The plasmid coding for improved Cas9 variants were obtained by sequential site directed mutagenesis starting from the pX-Cas9 plasmid. For the expression of previously published enhanced SpCas9 mutants the VP12 (obtained from Addgene, #72247) (Kleinstiver B P et al., Nature. 2016, 529(7587):490-5) and the eSpCas9(1.1) (obtained from Addgene, #71814) (Slaymaker I M et al., Science. 2016, 351(6268):84-8) plasmids were used. Desired spacer sequences were cloned as annealed oligonucleotides with appropriate overhangs into a double BbsI site upstream the guide RNA constant portion of a pUC19 plasmid containing a U6 promoter-driven expression cassette. For the experiments involving lentiviral vectors, the lentiCRISPRv1 transfer vector (obtained from Addgene, #49535) (Cong L et al., Science. 2013, 339(6121):819-23) was employed together with the pCMV-delta8.91 packaging vector (a kind gift from Didier Trono, EPFL, Switzerland) and pMD2.G (obtained from Addgene, #12259), coding for the vesicular stomatitis virus glycoprotein (VSVG), to produce viral particles. The lentiCRISPRv1 transfer vector contains an expression cassette for a codon-humanized version of a N-terminally FLAG-tagged SpCas9 fused through a 2A-peptide to the puromycin coding sequence to allow selection of transduced cells. A U6-driven expression cassette transcribes the sgRNA. Annealed oligos corresponding to the desired spacers were cloned into the guide RNA using a double BsmBI site. The lentiCRISPRv1-based vectors coding for enhanced SpCas9 variants were generated by swapping part of the SpCas9 coding sequence with a PCR fragment corresponding to the region of the CDS containing the mutations (for primers, see Appendix Table 2). The pTRE-GFP plasmid was obtained by subcloning the EGFP coding sequence from the pEGFP-N1 (Clontech) plasmid into the pTRE-Tight cloning vector (Clontech). A complete list of the guide RNA target sites is available in the Appendix. All oligonucleotides were purchased from Eurofins Genomics.

Yeast Culture.

The yLFM-ICORE yeast strain (generated by one of the Inventors' laboratory from the parental yIG397 strain, a kind gift from Richard Iggo) (Jegga A G et al., Proc Natl Acad Sci USA. 2008, 105(3):944-9; Tomso D J et al., Proc Natl Acad Sci USA. 2005, 102(18):6431-6) was used to generate the reporter yeast strains used in this study. Synthetic minimal media (SD) were employed in all yeast experiments (yeast nitrogen base without amino acids 6.7 g/L, L-isoleucine 600 mg/L, L-valine 150 mg/L, L-adenine 200 mg/L, L-arginine 20 mg/L, L-histidine 10 mg/L, L-leucine 100 mg/L, L-lysine 90 mg/L, L-methionine 20 mg/L, L-phenylalanine 50 mg/L, L-threonine 200 g/L, L-tryptophan 20 mg/L, L-uracil 20 mg/L, L-glutamic acid 100 mg/L, L-aspartic acid 200 g/L, L-serine 400 mg/L, D-(+)-glucose 20 g/L). Single amino acids were omitted according to the experimental setup when selective medium was required. For the induction of p415-GalL-Cas9-CYC1t, 20 g/L D-(+)-galactose and 10 g/L D-(+)-raffinose were used instead of dextrose. Specific medium for ADE2 mutants colour screening was prepared using low adenine concentrations (5 mg/L). When non-selective medium was required, YPDA rich medium was employed (yeast extract 10 g/L, peptone 20 g/L, D-(+)-Glucose 20 g/L, L-adenine 200 mg/L). All solutions were prepared using ddH$_2$O, filter-sterilized and stored at 4° C. Solid media were prepared by autoclave sterilization, adding 20 g/L of agar to the solution. All chemicals to prepare yeast media were obtained from Sigma-Aldrich.

Yeast Transformation.

The day prior to transformation, approximately 1 mm$^3$ of the desired yeast strain was inoculated in 5 mL of rich medium or selective synthetic medium and grew overnight at 30° C. while shaking at 200 rpm. The next day 3-5 mL of the culture were inoculated in a total of 30 mL of the same medium and grew at 30° C. at 200 rpm for further 2-4 hours. Cells were then harvested by centrifugation at 2000×g for 2', washed in 30 mL of ddH2O, centrifuged again at 2000×g for 2' and resuspended in 10 mL of LiAc/TE 1× (lithium acetate 0.1 M and Tris 10 mM EDTA 1 mM, pH 7.5). The solution was centrifuged again at 2000×g for 2' and resuspended in a proper volume of LiAc/TE 1× (100 mg of yeast pellet in 500 μL). The transformation mix contained 500 ng of plasmid DNA, 5 μl of carrier salmon sperm DNA (approx. 1 μg, Sigma-Aldrich) previously sheared by sonication and boiled at 100° C. for 10', 50 μL of resuspended yeast culture and 300 μL of polyethylene glycol (PEG) 500 g/L with a molecular weight of ~36,500 (Sigma-Aldrich) diluted in LiAc/TE 1X. After vortexing, the transformation mix was placed for 30' at 30° C. and then heat-shocked using a dry bath for 30' at 42° C. Cells were then centrifuged at 3000×g for 3', resuspended in 5 mL of the appropriate SD selective medium or directly plated on selective SD agarose plates and incubated at 30° C. For spontaneous reversion frequency evaluation, after transformation with p415-GalL-Cas9-CYC1t cells were grown in selective medium for 24 hours. The concentration of cells was then evaluated by measuring the $OD_{600}$ and 1000 cells were plated on selective plates depleted of leucine (SDl) or $10^6$ cells were spread on plates further depleted of adenine (SDla) of tryptophan (SDlt), to evaluate the number of revertants.

Yeast Colony PCR.

Colony PCRs were performed by resuspending approximately 1 $mm^3$ of yeast colony in 49 μL of $ddH_2O$. 1 μL of lyticase (10000 U/mL, Sigma-Aldrich) was added to digest the cell wall and the suspension was then incubated at 30° C. for 30'. The cells were pelleted, the supernatant was removed and the dry pellet was boiled for 10' at 100° C. The pellet was then resuspended in 50 μL of $ddH_2O$ and 5 μL were used as a template in the PCR reaction, using the Phusion High-Fidelity DNA Polymerase (Thermo Scientific).

Recovery of Plasmid DNA from Yeast.

In order to isolate the mutant Cas9 plasmids from yeast, single colonies were grown overnight at 30° C. shaking at 200 rpm in 5 mL of SD medium without leucine (SDl), to select for the presence of the p415-GalL-Cas9-CYC1t plasmid, while relaxing the selection on the guide RNA plasmid to induce its dilution and loss. The next day cells were harvested by centrifugation for 5' at 5000×g and resuspended in 250 μl of buffer A1 (Nucleospin Plasmid, Macherey-Nagel) containing 0.1 mg/ml of RNase A. Cells were then mechanically lysed by adding 100 μL of acid-washed glass beads (Sigma-Aldrich) and by vortexing continuously for 5'. Plasmid DNA was then recovered from the supernatant using standard miniprep silica columns, following the manufacturer's instructions. DNA was eluted in 30 μL of 10 mM TrisHCl pH 8.5. The eluted DNA was digested with the NcoI and NheI enzymes (New England BioLabs) to eliminate the sgRNA vector in order to avoid contaminations from the latter plasmids, which are also selectable through ampicillin resistance. After digestion, 10 μL were transformed in chemically competent *E. coli*. The plasmids recovered were then digested to verify their identity and then Sanger sequenced to identify the mutations introduced in the Rec1-II domain.

Assembly of Modified TRP1 and ADE2 Genomic Cassettes.

The DNA cassettes used to engineer the ADE2 (ADE2-Off1, ADE2-Off2, ADE2-Off3 and ADE2-Off4) and TRP1 (TRP1-On) genomic loci were built using a similar strategy. Two different colony PCR were performed to amplify the two halves of each wild-type locus separately. The first one employed a forward primer upstream of the gene CDS and a reverse overhang primer containing the on- or off1-4-target sequence followed by the KpnI or BamHI restriction sites, respectively (see Appendix Table 3). All reverse primers contained a stop codon before the on/off-target sequence to ensure truncation of the protein. The second half of the cassette was assembled using a reverse primer which anneals downstream the ADE2 and TRP1 coding sequences and a forward primer which anneals 100 bp before the reverse primer used to build the first half of the cassette. In this way, when the two parts were joined together, the final construct contained a 100 bp long homology region upstream and downstream of the on-/off-target sequences. In addition, these forward primers contained the same restriction site present in the reverse primer of the corresponding first half of the cassette. The TRP1 and ADE2 fragments were assembled by ligating the two halves digested with KpnI or BamHI (New England BioLabs), accordingly. The products were separated on an agarose gel to remove homo-ligation-derived fragments. The final cassette was enriched by PCR using the most external primers and directly transformed in yeast.

Generation of Yeast Reporter Strains.

The delitto perfetto approach enables the genetic targeting of specific loci with the practicality of a general selection system through the exploitation of the homology directed repair mechanism that is particularly efficient in yeast (Stuckey S and Storici F, Methods Enzymol. 2013, 533:103-31). The first step consists in the insertion of a COunter selectable REporter I-SceI cassette (CORE-I-SceI) in the specific locus of interest. The cassette contains a recognition site for I-SceI, as well as the coding sequence for the endonuclease itself under the control of the galactose-inducible GAL1 promoter, the resistance gene kanMX4 (G418) and the counterselectable marker URA3 gene from *Kluyveromyces lactis* (KlURA3). The CORE-I-SceI cassette was amplified with primers containing specific overhangs for the ADE2 and TRP1 loci (see Appendix Table 3). Each locus was edited sequentially, following the same procedure, starting from the ADE2 locus. 500 ng of locus-specific CORE-I-SceI cassette were transformed in yeast and cells were plated on YPDA plates and incubated at 30° C. overnight. The next day the colonies were replica-plated on YPDA media containing 200 μg/mL of G418 (Invivogen). Resistant colonies were screened for successful cassette insertion into the desired locus by colony PCR using primers annealing to the genomic sequences flanking the integration site and to the cassette. The CORE-I-SceI cassette integrated within the targeted locus was then swapped with the final edited sequence (TRP1-On, ADE2-Off1, ADE2-Off2, ADE2-Off3 and ADE2-Off4), generating a total of four different yeast strains characterized by the same on-target sequence and four different off-targets. The appropriate intermediate yeast strain containing the target CORE-I-SceI cassette was inoculated overnight in 5 mL of YPDA. The next day, before transformation, the inoculum was resuspended in 30 mL of synthetic medium containing galactose and raffinose instead of dextrose (SRG). This step is essential to induce the transcription of the I-SceI endonuclease which cuts its target site located within the CORE cassette. This DSB increases the normal frequency of HR-driven repair events, favouring cassette-swap with the desired new sequence. After 4 hours in SRG, yeast was transformed with 500 ng of the HR template containing the desired sequence following the standard transformation protocol. Transformants were then plated on SD containing 60 mg/L of uracil and 1 g/l of 5-fluoroorotic acid (5-FOA) (Toronto Research Chemicals). 5-FOA in the presence of orotidine 5'-phosphate decarboxylase (encoded by KlURA3) is converted in fluo-rouracil which is a potent thymidylate synthase inhibitor. 5-FOA-resistan colonies were then replica-plated on YPDA and YPDA supplemented with G418, to further select for the loss of the CORE cassette. By comparing the two replica plates it is possible to select G418-sensitive FOA-resistant colonies that correspond to positive clones. Colony PCRs, performed using genomic primers that anneal upstream and downstream of the entire genomic locus, were analysed by Sanger sequencing to confirm the sequence of the edited locus. The newly generated yeast strains containing the modified TRP1 and ADE2 loci were called yACMO-off1, yACMO-off2, yACMO-off3 and yACMO-off4, characterized by a selected on-target sequence in the TRP1 locus and four different off-target sequences in the ADE2 locus, each containing a single mismatch with respect to the on-target sequence in a position that is more PAM-proximal for off1 and more PAM-distal for off4 (see Appendix Table 4).

Yeast Assay Readout.

The ADE2 and TRP1 genes are key enzymes in the metabolic pathways leading to the production of adenine and tryptophan and for this reason their knockout destroys yeast ability to grow on medium depleted of the two related nutrients. The yACMO yeast strains generated in this study are deficient for the TRP1 and ADE2 gene activity unless Cas9 cuts the target sequence interrupting each coding sequence: single strand annealing-mediated recombination between the two 100 bp homology regions on both sides of the target sites ensure reconstitution of the wild-type locus. A screening based on auxotrophies selection can then be used to evaluate Cas9 cleavage activity at the two genomic loci, measuring both on-targeting and off-targeting events. After transformation with p415-GalL-Cas9-CYC1t and pRS316-SNR52p-gRNA.ON-SUP4t, cells were grown in synthetic medium without leucine and uracil (SDlu) for 4 hours before an overnight induction in galactose-containing medium (SRGlu). Cells were then plated in equal numbers on SDlu plates, to measure the total number of transformants, and on SDlu plates depleted of tryptophan and with low adenine concentration (SDluta$_5$), to distinguish colonies in which Cas9 cleaved only the on- or also the off-target sequences. In particular, when observing the SDluta$_5$ readout plate different phenotypes could be present: the absence of growth indicates lack of editing of the TRP1 locus (TRP1$^-$/ADE2$^{+/-}$); the growth of a red colony (TRP1$^+$/ADE2$^-$) indicates editing only at the TRP1 locus, with no off-target activity detected; the growth of a white colony (TRP1$^+$/ADE2$^+$) indicates editing at both the TRP1 and the ADE2 loci, detecting off-target cleavages. The typical red pigmentation of the colony is determined by the accumulation into the cellular vacuole of an intermediate of the adenine biosynthetic pathway generated by the block at the level of the ADE2 gene product. By comparing the total number of colonies obtained on the SDlu and the SDluta$_5$ it is possible to measure the on-target cleavage efficiency, while by quantifying the percentage of red and white colonies on the SDluta$_5$ plate an estimation of the specificity of Cas9 activity relative to the off-target sequence tested can be obtained.

Yeast Screening for SpCas9 Mutants.

The mutants' library was generated by error prone PCR (epPCR) using the GeneMorph II kit (Agilent). Following the manufacturer's instructions, the initial amount of template DNA (p415-GalL-Cas9-CYC1t) and the number of cycles were set to obtain an average of 5 mutations per kilobase. 50 bp-long primers were selected to anneal 150 bp upstream and downstream of the REC1-II coding sequence (see Appendix Table 5). The PCR library was directly assembled in vivo by co-transformation of the mutagenized amplicon pool with the p415-GalL-Cas9-CYC1t plasmid, previously digested with NcoI and NheI (New England BioLabs) to remove the REC1-II domain, with an insert/plasmid ratio of 3:1. The two 150 bp homology regions at both ends of the amplicons were used by yeast to repair the digested plasmid by homologous recombination, thus incorporating the mutagenized portion. Clones containing mutations in these 150 bp flanking regions were probably negatively selected during this in vivo assembly step due to loss of complete homology. Nonetheless, these mutations lied outside our region of interest (the REC1-II domain). The mutagenic library was screened concomitantly to its assembly by co-transformation of the fragments in the yACMO-off4 yeast strain stably expressing a sgRNA matching the on-target sequence contained in the TRP1 locus. After transformation, the culture was grown overnight in SD medium lacking uracil and leucine (SDlu, for selecting cells carrying both the sgRNA- and Cas9-expressing plasmids) to allow recovery and correct recombination. The next day, Cas9 expression was induced by growing the culture in galactose-containing medium (SRGlu) for 5 hours prior to plating on several selective plates lacking tryptophan and containing low concentration of adenine (SDluta$_5$), to discriminate colonies according to the editing status of the TRP1 and ADE2 loci. After 48 hours, TRP1$^+$/ADE2$^-$ (red) colonies were streaked on selective plate with low adenine and no tryptophan containing galactose and raffinose (SR-Gluta$_5$) to keep Cas9 expression constitutively induced and force the generation of off-target cleavages. After further 48 hours of incubation, Cas9-expressing plasmids were extracted from the red-most streaks, corresponding to colonies in which Cas9 cleaved only the on-target site, and the mutations were characterized by Sanger sequencing.

Yeast Colony Colour Analysis and Quantification.

All plates images were acquired with a Canon EOS 1100D (1/60, f/9.0 and ISO 800) and analysed with OpenCFU (Geissmann Q, PLoS One. 2013; 8(2):e54072). For all images an inverted threshold (value=2) was used with a radius between 8 and 50 pixels. Discrimination between white and red colonies was calculated by computing the average signal in the RGB channels and setting a manual threshold that accurately discriminates between red and white colonies in each experiment.

Mammalian Cells and Transfections.

293T/17 cells were obtained from the American Type Culture Collection (obtained from the ATCC) and were cultured in Dulbecco's modified Eagle's medium (DMEM; Life Technologies) supplemented with 10% fetal calf serum (FCS; Life Technologies) and antibiotics (PenStrep, Life Technologies). 293multiGFP cells were generated by stable transfection with pEGFP-IRES-Puromycin and selected with 1 µg/ml of puromycin. 293blastEGFP were obtained by low MOI infection of HEK293T cells with the EGFP-expressing lentiviral vector pAIB-GFP followed by clonal selection with 5 µg/ml of blasticidin. For transfection, 1×10$^5$ 293 multiGFP or 293T cells/well were seeded in 24-well plates and transfected the next day using TransIT-LT1 (Mirus Bio) according to manufacturer's protocol using 400-750 ng of Cas9-expressing plasmids and 200-250 ng of sgRNA-expressing plasmids. For transient transfection experiments involving EGFP expression, 100 ng of the pEGFP-N1 plasmid were used. To determine the level of EGFP downregulation by Cas9 after transfection into 293multiGFP, cells were collected 7 days post-transfection and were analysed by flow cytometry using a FACSCanto (BD Biosciences).

Lentiviral Vector Production and Transductions.

Lentiviral particles were produced by seeding 4×10$^6$ 293 T cells into a 10 cm dish. The day after, plates were transfected with 10 µg of each lentiCRISPR-based (Cong L et al., Science. 2013, 339(6121):819-23) transfer vector together with 6.5 μg pCMV-deltaR8.91 packaging vector and 3.5 μg pMD2.G using the polyethylenimine (PEI) method. After an overnight incubation, the medium was replaced with fresh complete DMEM and 48 hours later the supernatant containing the viral particles was collected, spun down at 500×g for 5 minutes and filtered through a 0.45 μm PES filter. Quantification of the vector titers was performed using the SG-PERT method (Pizzato M et al., J Virol Methods. 2009, 156(1-2):1-7). Vectors stocks were conserved at −80° C. for future use.

For transductions, $10^5$ 293 blastGFP cells were seeded in a 24-well plate and the next day were transduced with 0.4 Reverse Transcriptase Units (RTU)/well of each vector by centrifuging at 1600×g 16° C. for 2 hours. After an overnight incubation, the viral supernatant was removed and the cells were kept in culture for a total of 48 hours before adding 0.5 μg/ml puromycin selection that was maintained throughout the experiment. To determine the level of EGFP downregulation by Cas9 after infection, 293blastGFP cells were collected at the indicated time-points after transduction and were analysed by flow cytometry using a FACSCanto (BD Biosciences).

Detection of Cas9-Induced Genomic Mutations.

Genomic DNA was obtained at 7 days post-transfection, using the QuickExtract DNA extraction solution (Epicentre). PCR reactions to amplify genomic loci were performed using the Phusion High-Fidelity DNA polymerase (Thermo Fisher). Samples were amplified using the oligos listed in Appendix Table 8. Purified PCR products were analyzed by sequencing and applying the TIDE tool (Brinkman E K et al., Nucleic Acids Res. 2014, 42(22):e168). To quantify the CCR2-CCR5 chromosomal deletion, a semi-quantitative PCR approach was set-up using primers flanking the CCR5 on-target site and the CCR2 off-target locus (Appendix Table 8). The number of PCR cycles was modulated in order not to reach the amplification plateau. Quantifications were obtained by performing densitometric analyses using the ImageJ software and exploiting the FANCF genomic locus as an internal normalizer.

Western Blots.

Cells were lysed in NEHN buffer (20 mM HEPES pH 7.5, 300 mM NaCl, 0.5% NP40, NaCl, 1 mM EDTA, 20% glycerol supplemented with 1% of protease inhibitor cocktail (Pierce)). Cell extracts were separated by SDS-PAGE using the PageRuler Plus Protein Standards as the standard molecular mass markers (Thermo Fisher Scientific). After electrophoresis, samples were transferred to 0.22 μm PVDF membranes (GE Healthcare). The membranes were incubated with mouse anti-FLAG (Sigma) for detecting SpCas9 and the different high-fidelity variants, with mouse anti-α-tubulin (Sigma) for a loading control and with the appropriate HRP conjugated goat anti-mouse (KPL) secondary antibodies for ECL detection. Images were acquired using the UVItec Alliance detection system.

Targeted Deep-Sequencing.

Selected off-target sites for the VEGFA3 and EMX1 genomic loci, together with their relative on-target, were amplified using the Phusion high-fidelity polymerase (Thermo Scientific) or the EuroTaq polymerase (Euroclone) from 293T genomic DNA extracted 7 days after transfection with wild-type SpCas9 or evoCas9 together with sgRNAs targeting the EMX1 and the VEGFA3 loci, or a pUC empty vector. Off-target amplicons were pooled in near-equimolar concentrations before purification and indexing. Libraries were indexed by PCR using Nextera indexes (Illumina), quantified with the Qubit dsDNA High Sensitivity Assay kit (Invitrogen), pooled according to the number of targets and sequenced on an Illumina Miseq system using an Illumina Miseq Reagent kit V3—150 cycles (150 bp single read). The complete primer list used to generate the amplicons is reported in Appendix Table 7.

A reference genome was built using Picard (http://broadinstitute.github.io/picard) and samtools (Li H at al., Bioinformatics. 2009, 25(16):2078-9) from DNA sequences of the considered on-/off-target regions. Raw sequencing data (FASTQ files) were mapped against the created reference genome using BWA-MEM (Li H and Durbin R, Bioinformatics. 2010, 26(5):589-95) with standard parameters and resulting alignment files were sorted using samtools. Only reads with mapping quality above or equal to 30 were retained. Presence of indels in each read for each considered region was determined by searching indels of size 1 bp directly adjacent to the predicted cleavage site or indels of size >=2 bp overlapping flanking regions of size 5 bp around the predicted cleavage site.

GUIDE-Seq Experiments and Data Analysis.

GUIDE-seq was performed as previously described (Bolukbasi M F et al., Nat Methods. 2015, 12(12):1150-6) with few modifications. Briefly, $2 \times 10^5$ 293 T cells were transfected with 750 ng of a Cas9 expressing plasmid, together with 250 ng of sgRNA-coding plasmid or an empty pUC19 plasmid and 10 μmol of the bait dsODN containing phosphorothioate bonds at both ends (designed according to the original GUIDE-seq protocol) using Lipofectamine 3000 transfection reagent (Invitrogen). Three days post transfection genomic DNA was extracted using the DNeasy Blood and Tissue kit (Qiagen) following the manufacturer's instructions and sheared to an average length of 500 bp with the Bioruptor Pico sonication device (Diagenode). Library preparations were performed with the original adapters and primers according to previous work (Tsai S Q et al., Nat Biotechnol. 2015, 33(2):187-97). Libraries were quantified with the Qubit dsDNA High Sensitivity Assay kit (Invitrogen) and sequenced with the MiSeq sequencing system (Illumina) using an Illumina Miseq Reagent kit V2—300 cycles (2×150 bp paired-end).

Raw sequencing data (FASTQ files) were analyzed using the GUIDE-seq computational pipeline (Tsai S Q et al., Nat Biotechnol. 2015, 33(2):187-97). After demultiplexing, putative PCR duplicates were consolidated into single reads. Consolidated reads were mapped to the human reference genome GrCh37 using BWA-MEM (Li H and Durbin R, Bioinformatics. 2010, 26(5):589-95); reads with mapping quality lower than 50 were filtered out. Upon the identification of the genomic regions integrating double-stranded oligodeoxynucleotide (dsODNs) in aligned data, RGN sites were retained if at most eight mismatches against the target were present and if absent in the background controls. Visualization of aligned off-target sites is available as a color-coded sequence grid.

APPENDIX

TABLE 1

Figure 4:
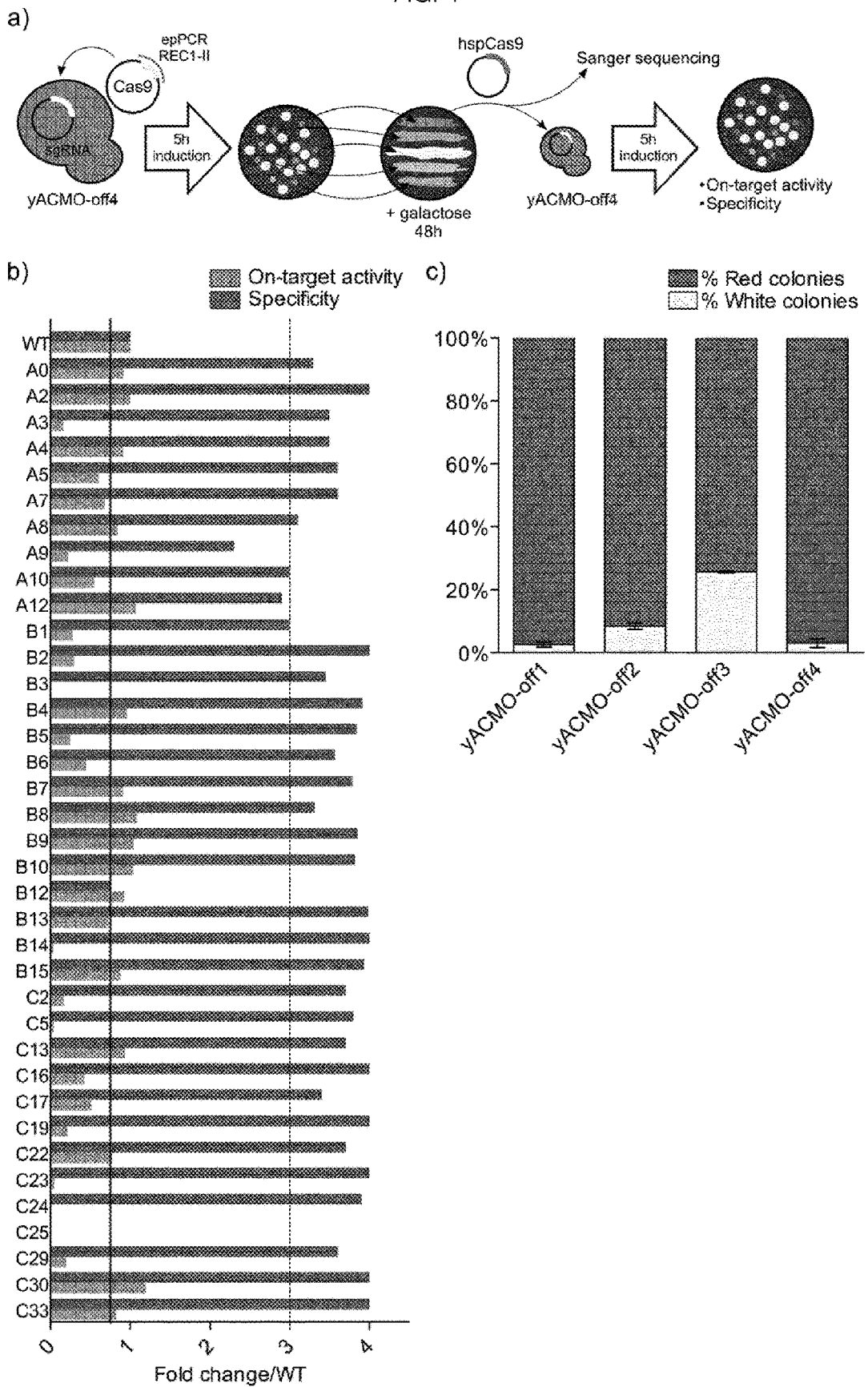
FIG. 4. Yeast screen for high-specificity SpCas9 variants (a) Schematic representation of the yeast screening workflow. (b) Evaluation of the on-target activity and the specificity of SpCas9 variants obtained from the yeast screening through analysis with the yACMO-off4 reporter strain. Cas9 expression was induced for 5 h prior to plating. See Appendix Table 1. (c) Evaluation of the specificity of the C13 variant. C13 was transformed in the yACMO-off1/off4 reporter strains expressing an on-target sgRNA and the percentage of red (on-target) and white (off-target) colonies was evaluated after 24h of Cas9 expression. Error bars represent s.e.m. for n=3.

Mutants obtained from the yeast screen, relative to FIG. 4.

| Mutant | Amino acids substitutions |
|---|---|
| A0 | R403H, N612Y, L651P, K652E, G715S |
| A1 | R403H, N612Y, L651P, K652E, G715S |
| A2 | W659R, R661L |
| A3 | L540Q, L607P |

TABLE 1-continued

Mutants obtained from the yeast screen, relative to FIG. 4.

| Mutant | Amino acids substitutions |
|---|---|
| A4 | R400H, Y450S |
| A5 | T472A, P475H, A488V |
| A6 | N407P, F498I, P509L |
| A7 | D406Y |
| A8 | A488V, D605V, R629G, T657A |
| A9 | S487Y, N504S, E573D |
| A10 | K377E, L598P, L651H |
| A11 | T496A, N609D, A728G |
| A12 | Y450H, F553L, Q716H |
| B1 | K484M, Q695H, Q712R |
| B2 | L683P |
| B3 | P449S, F704S |
| B4 | S675C, Q695L |
| B5 | W464L |
| B6 | I473F, D550N, Q739E |
| B7 | A421V, R661W |
| B8 | M495V, K526N, S541P, K562E |
| B9 | D406V, E523K |
| B10 | N407H, K637N, N690I |
| B11 | M495V, K526N, S541P, K562E |
| B12 | I679V, H723L |
| B13 | N522K, G658E |
| B14 | L423P, M465R, Y515N, K673M |
| B15 | R654H, R691Q, H698Q |
| C1 | L683P |
| C2 | T474A |
| C3 | L683P |
| C4 | L683P |
| C5 | W476R, L738P |
| C6 | W476R, L738P |
| C7 | W476R, L738P |
| C8 | W476R |
| C9 | L683P |
| C10 | L683P |
| C11 | L683P |
| C12 | L683P |
| C13 | K526E |
| C14 | F405L, F518L, L651P, I724V |
| C15 | K526E |
| C16 | E470D, I548V, A589T, Q695H |
| C17 | E470D, I548V, A589T, Q695H |
| C18 | E470D, I548V, A589T, Q695H |
| C19 | Y450N, H698P, Q739K |
| C20 | K526E |
| C21 | F405L, F518L, L651P, I724V |
| C22 | F405L, F518L, L651P, I724V |
| C23 | D397E, Y430C, L666P |
| C24 | L380*, I473V |
| C25 | Frameshift, N522S, K646R, D686V |
| C26 | Frameshift, N522S, K646R, D686V |
| C27 | Frameshift, N522S, K646R, D686V |
| C28 | Frameshift, N522S, K646R, D686V |
| C29 | R691L, H721R, I733V |
| C30 | Q402R, V561M, Q695H |
| C31 | Q402R, V561M, Q695H |
| C32 | Q402R, V561M, Q695H |
| C33 | F478Y, N522I, L727H |
| C34 | Frameshift, A640T, Q709L |

*stop codon

TABLE 2

Primers used for plasmid cloning

| Primer name | Sequence (5'-...-3') |
|---|---|
| Rec1-II-NheI-F | CCAGAAAGCACAAGTTGCTAGCCAGGGGACAGTC (SEQ ID N. 4) |
| Rec1-II-NheI-R | GACTGTCCCCCTGGCTAGCAACTTGTGCTTTCTGG (SEQ ID N. 5) |
| Rec1-II-NcoI-F | CAGCGCACTTTCGACCATGGAAGCATCCCCCA (SEQ ID N. 6) |
| Rec1-II-NcoI-R | TGGGGGATGCTTCCATGGTCGAAAGTGCGCTG (SEQ ID N. 7) |
| T3-Forward | AATTAACCCTCACTAAAGGG (SEQ ID N. 8) |
| T7-Reverse | TAATACGACTCACTATAGGG (SEQ ID N. 9) |
| sgRNA-Ontarget-F | CTCGTGACCACCCTGACCTAGTTTTAGAGCTAGAAATAGCAA (SEQ ID N. 10) |
| sgRNA-Ontarget-R | TAGGTCAGGGTGGTCACGAGGATCATTTATCTTTCACTGCG (SEQ ID N. 11) |
| Apa-ZhangCas-F | ACGTGGGCCCTCTGGCCAG (SEQ ID N. 12) |
| Nhe-ZhangCas-R | TACGCTAGCTCCCTTTTTCTTTTTTGCCTGG (SEQ ID N. 13) |
| Apa-JoungCas-F | ATTAGGGCCCCCTGGCCCGAGGGAAC (SEQ ID N. 14) |
| Spe-JoungCas-R | TAATACTAGTGACTTTCCTCTTCTTCTTGGG (SEQ ID N. 15) |

TABLE 3

Primers used yeast reporter cassette construction

| Primer name | Sequence (5'-...-3') |
|---|---|
| TRP1-genomic-F | CCAAGAGGGAGGGCATTGG (SEQ ID N. 16) |
| TRP1Pt1-ON-Kpn-R | TGCGGTACCGTAGGTCAGGGTGGTCACGAGTTAG AGGAACTCTTGGTATTCTTGC (SEQ ID N. 17) |
| TRP1Pt2-Kpn-F | TTAGGTACCGTAATCAACCTAAGGAGGATGTTT (SEQ ID N. 18) |
| TRP1-genomic-R | TGCTTGCTTTTCAAAAGGCCTG (SEQ ID N. 19) |
| ADE2-genomic-F | TGCCTAGTTTCATGAAATTTTAAAGC (SEQ ID N. 20) |
| ADE2Pt1-OFF1-Bam-R | CCAGGATCCGGAGGTCAGGGTGGTCACGAGTTAG ACGCAAGCATCAATGGTAT (SEQ ID N. 21) |
| ADE2Pt1-OFF2-Bam-R | CCAGGATCCGTAGGTAAGGGTGGTCACGAGTTAG ACGCAAGCATCAATGGTAT (SEQ ID N. 22) |
| ADE2Pt1-OFF3-Bam-R | CCAGGATCCGTAGGTCAGGGCGGTCACGAGTTAG ACGCAAGCATCAATGGTAT (SEQ ID N. 23) |
| ADE2Pt1-OFF4-Bam-R | CCAGGATCCGTAGGTCAGGGTGGTAACGAGTTAG ACGCAAGCATCAATGGTAT (SEQ ID N. 24) |
| ADE2Pt2-Bam-F | ATTAGGATCCTGGTGTGGAAATGTTCTATTTAG (SEQ ID N. 25) |
| ADE2-genomic-R | GTAATCATAACAAAGCCTAAAAAATAG (SEQ ID N. 26) |
| TRP1-CORE-F | TATTGAGCACGTGAGTATACGTGATTAAGCACACA AAGGCAGCTTGGAGTTAGGGATAACAGGGTAATTT GGATGGACGCAAAGAAGT (SEQ ID N. 27) |
| TRP1-CORE-R | TGCAGGCAAGTGCACAAACAATACTTAAATAAATA CTACTCAGTAATAACTTCGTACGCTGCAGGTCGAC (SEQ ID N. 28) |
| ADE2-CORE-F | CCTACTATAACAATCAAGAAAAACAAGAAAATCGG ACAAAACAATCAAGTTAGGGATAACAGGGTAATTT GGATGGACGCAAAGAAGT (SEQ ID N. 29) |
| ADE2-CORE-R | ATATCATTTTATAATTATTTGCTGTACAAGTATATCA ATAAACTTATATATTCGTACGCTGCAGGTCGAC (SEQ ID N. 30) |

TABLE 4

On and off target sites used to generate the yACMO strains

| Target name | Sequence (5'-...-3', with lowercase PAM), mismatch in bold |
|---|---|
| TRP1-on | CTCGTGACCACCCTGACCTAcgg (SEQ ID N. 31) |
| ADE2-off1 | CTCGTGACCACCCTGACCTCcgg (SEQ ID N. 32) |
| ADE2-off2 | CTCGTGACCACCCTTACCTAcgg (SEQ ID N. 33) |
| ADE2-off3 | CTCGTGACCGCCCTGACCTAcgg (SEQ ID N. 34) |
| ADE2-off4 | CTCGTTACCACCCTGACCTAcgg (SEQ ID N. 35) |

TABLE 5

Error-prone PCR primers

| Primer name | Sequence (5'-...-3') |
|---|---|
| epPCR-F | GTCTAAAAATGGCTACGCCGGATACATTGACGGCG GAGCAAGCCAGGAGG (SEQ ID N. 36) |
| epPCR-R | TCTCGGGCCATCTCGATAACGATATTCTCGGGCTTA TGCCTTCCCATTAC (SEQ ID N. 37) |

TABLE 6

Spacer sequences used to prepare sgRNAs for reporter assays

| Target name | Spacer sequence (5'-...-3') |
|---|---|
| GFPon | GGGCACGGGCAGCTTGCCGG (SEQ ID N. 38) |
| GFP1314 | GGGCACCCGCAGCTTGCCGG (SEQ ID N. 39) |
| GFP1819 | GCCCACGGGCAGCTTGCCGG (SEQ ID N. 40) |
| GFP18 | GGCCACGGGCAGCTTGCCGG (SEQ ID N. 41) |
| GFP site 2 | GTCGCCCTCGAACTTCACCT (SEQ ID N. 42) |

TABLE 6-continued

Spacer sequences used to prepare sgRNAs for reporter assays

| Target name | Spacer sequence (5'-...-3') |
|---|---|
| GFP site 14 | GAAGGGCATCGACTTCAAGG (SEQ ID N. 43) |
| GFP site 16 | GCTGAAGCACTGCACGCCGT (SEQ ID N. 44) |
| GFP site 18 | GACCAGGATGGGCACCACCC (SEQ ID N. 45) |
| GFP site 20 | GAAGTTCGAGGGCGACACCC (SEQ ID N. 46) |
| GFPon-19nt | GGCACGGGCAGCTTGCCGG (SEQ ID N. 47) |
| GFPB-18nt | GGCAAGCTGCCCGTGCCC (SEQ ID N. 48) |
| GFPW-17nt | GTGACCACCCTGACCTA (SEQ ID N. 49) |
| TetO-on | GTGATAGAGAACGTATGTCG (SEQ ID N. 50) |
| TetO-on+G | gGTGATAGAGAACGTATGTCG (SEQ ID N. 51) |
| TetO-off6 | GTGATAGAGAACGTCTGTCG (SEQ ID N. 52) |
| TetO-off1314 | GTGATACTGAACGTATGTCG (SEQ ID N. 53) |
| TetO-off1819 | GACATAGAGAACGTATGTCG (SEQ ID N. 54) |

5'-mismatched nucleotides are indicated in lowercase. Mutations are indicated in bold.

TABLE 7

Targeted deep-sequencing oligos
Common forward overhang: 5'-TCGTCGGCAGCGTCAGATGTGTATAAGAGACAG-3' (SEQ ID N. 55)
Common reverse overhang: 5'-GTCTCGTGGGCTCGGAGATGTGTATAAGAGACAG-3' (SEQ ID N. 56)

| Locus | Target | Forward (5'-...-3') | Reverse (5'-...-3') |
|---|---|---|---|
| EMX1-on | GAGTCCGAGCAGAAGAAGAAggg (SEQ ID N. 57) | CCGGAGGACAAAGTACAAACGGC (SEQ ID N. 58) | AAGCAGCACTCTGCCCTCGTG (SEQ ID N. 59) |
| EMX1-ot1 | GAGTTAGAGCAGAAGAAGAAagg (SEQ ID N. 60) | CTTTTATACCATCTTGGGGTTACAG (SEQ ID N. 61) | CTAGGAAAGATTAACAGAGAGTCTGAC (SEQ ID N. 62) |
| EMX1-ot2 | GAGTCTAAGCAGAAGAAGAAgag (SEQ ID N. 63) | CAATGTGCTTCAACCCATCACGGC (SEQ ID N. 64) | CCTCTACTTCATTGTACTCAAGGTAAG (SEQ ID N. 65) |
| EMX1-ot3 | AAGTCTGAGCACAAGAAGAAtgg (SEQ ID N. 66) | TAGTTCTGACATTCCTCCTGAGGG (SEQ ID N. 67) | CTCTGTTGTTATTTTTTGGTCAATATCTG (SEQ ID N. 68) |
| EMX1-ot4 | GAGTCCTAGCAGGAGAAGAAag (SEQ ID N. 69) | AAAGCCTGGAGGCTGCCAGGT (SEQ ID N. 70) | ATCTAGCTGTCCTGTCTCATTGGC (SEQ ID N. 71) |
| EMX1-ot5 | GAGGCCGAGCAGAAGAAAGAcgg (SEQ ID N. 72) | CAGGAGCCGGGTGGGAG (SEQ ID N. 73) | CCTCAGCCTTCCCTCAGCCAC (SEQ ID N. 74) |
| VEGFA3-on | GGTGAGTGAGTGTGTGCGTGtgg (SEQ ID N. 75) | CTGGGTGAATGGAGCGAGCAG (SEQ ID N. 76) | GGAAGGCGGAGAGCCGGACA (SEQ ID N. 77) |
| VEGFA3-ot1 | AGTGAGTGAGTGTGTGTGTGggg (SEQ ID N. 78) | GAAGGGGAGGGGGAAGTCACC (SEQ ID N. 79) | CGTGCGTGCCGCCGTTGATC (SEQ ID N. 80) |
| VEGFA3-ot2 | TGTGGGTGAGTGTGTGCGTGagg (SEQ ID N. 81) | TCTGTCACCACACAGTTACCACC (SEQ ID N. 82) | GTAGTTGCCTGGGGATGGGGTATG (SEQ ID N. 83) |
| VEGFA3-ot3 | GCTGAGTGAGTGTGTGCGTGATGCGTGtgg (SEQ ID N. 84) | CACCTGGCCCATTTCTCCTTTGAGG (SEQ ID N. 85) | TGGGGACAGCATGTGCAAGCCACA (SEQ ID N. 86) |
| VEGFA3-ot4 | GGTGAGTGAGTGTGTGTGTGagg (SEQ ID N. 87) | GGACCCCTCTGACAGACTGCA (SEQ ID N. 88) | CACACACCCTCACATACCCTCAC (SEQ ID N. 89) |
| VEGFA3-ot5 | AGAGAGTGAGTGTGTGCATGagg (SEQ ID N. 90) | GGAAGAATGCAAAGGAGAAGCAAGTAC (SEQ ID N. 91) | GACCTGGTGGGAGTTGATTGGATC (SEQ ID N. 92) |

TABLE 7-continued

Targeted deep-sequencing oligos
Common forward overhang: 5'-TCGTCGGCAGCGTCAGATGTGTATAAGAGACAG-3' (SEQ ID N. 55)
Common reverse overhang: 5'-GTCTCGTGGGCTCGGAGATGTGTATAAGAGACAG-3' (SEQ ID N. 56)

| Locus | Target | Forward (5'-...-3') | Reverse (5'-...-3') |
|---|---|---|---|
| VEGFA3-ot6 | AGTGTGTGAGTGTGTGCGTGtgg (SEQ ID N. 93) | CCTTGGGAATCTATCTTGAATAGGCCT (SEQ ID N. 94) | GACACCCCACACACTCTCATGC (SEQ ID N. 95) |
| VEGFA3-ot7 | TGTGAGTAAGTGTGTGTGTgg (SEQ ID N. 96) | CCTAAGCTGTATGTGAGTCCCTGA (SEQ ID N. 97) | CTGTTTTGCTAAGAGATGATTAGATGGTC (SEQ ID N. 98) |
| VEGFA3-ot8 | GTTGAGTGAATGTGTGCGTGagg (SEQ ID N. 99) | GCCCTCTCCGGAAGTGCCTTG (SEQ ID N. 100) | GAAGGGTTGGTTTGGAAGGCTGTC (SEQ ID N. 101) |
| VEGFA3-ot9 | GGTGAGTGAGTGCGTGCGGGtgg (SEQ ID N. 102) | CCACAGGAATTTGAAGTCCGTGCT (SEQ ID N. 103) | CCCCACGTCCACCCATACACAC (SEQ ID N. 104) |
| VEGFA3-ot10 | AGCGAGTGGGTGTGTGCGTGggg (SEQ ID N. 105) | GACGTCTGGGTCCCGAGCAGT (SEQ ID N. 106) | GGCCGTCAGTCGGTCCCGA (SEQ ID N. 107) |
| VEGFA3-ot11 | TGTGAGTGAGTGTGTGCGTGtga (SEQ ID N. 108) | GGAGGGTTGAACTGTGACAGAACTG (SEQ ID N. 109) | TGAGTATGTGTGAGTGAGAGTGTGCA (SEQ ID N. 110) |
| VEGFA3-ot12 | ACTGTGTGAGTGTGTGCGTGagg (SEQ ID N. 111) | GATCCTTAGGCGTGCGTGTGC (SEQ ID N. 112) | CACCGGCACAGTGACACTCAC (SEQ ID N. 113) |
| VEGFA3-ot13 | TGTGAGTGAGTGTGTATGggg (SEQ ID N. 114) | AGACCTTCAATGTGGATGTGCGTG (SEQ ID N. 115) | CATAGAGTGTAGCAGATTTCCATAACTTC (SEQ ID N. 116) |

Mutations are indicated in bold. PAM are included in lowercase.

TABLE 8

Spacer sequences for genomic targets & oligos for the amplification of genomic loci

| Locus | Target | Forward (5'-...-3') | Reverse (5'-...-3') |
|---|---|---|---|
| VEGFA3 | GGTGAGTGAGTGTGTGCGTGTGG (SEQ ID N. 75) | GCATACGTGGGCTCCAACAGGT (SEQ ID N. 117) | CCGCAATGAAGGGAAGCTCGA (SEQ ID N. 118) |
| ZSCAN2 | GTGCGGCAAGAGCTTCAGCCGGG (SEQ ID N. 119) | GACTGTGGGCAGAGGTTCAGC (SEQ ID N. 120) | TGTATACGGGACTTGACTCAGACC (SEQ ID N. 121) |
| EMX1-K | GAGTCCGAGCAGAAGAAGAAGGG (SEQ ID N. 57) | CTGCCATCCCCTTCTGTGAATGT (SEQ ID N. 122) | GGAATCTACCACCCAGGCTCT (SEQ ID N. 123) |
| VEGFA2 | GACCCCCTCCACCCCGCCTCCGG (SEQ ID N. 124) | TCAGCGGACTCACCGGCCAG (SEQ ID N. 125) | GCGCCGAGTCGCCACTGCGG (SEQ ID N. 126) |
| FANCF2 | GCTGCAGAAGGGATTCCATGAGG (SEQ ID N. 127) | GCCAGGCTCTCTTGGAGTGTC (SEQ ID N. 128) | AGCATAGCGCCTGGCATTAATAGG (SEQ ID N. 129) |
| FANCF2-OT1 | GCTGCAGAAGGGATTCCAAGAGG (SEQ ID N. 130) | CCC GTGAGGTGCTGAGATTTGAAC (SEQ ID N. 131) | CACATGGAGGAGGTGACGCTG (SEQ ID N. 132) |
| CCR5sp11 | GGTACCTATCGATTGTCAGGAGG (SEQ ID N. 133) | ATGCACAGGGTGGAACAAGATGGA (SEQ ID N. 134) | CTAAGCCATGTGCACAACTCTGAC (SEQ ID N. 135) |

TABLE 8-continued

Spacer sequences for genomic targets & oligos for the amplification of genomic loci

| Locus | Target | Forward (5'-...-3') | Reverse (5'-...-3') |
|---|---|---|---|
| CCR2 | GGTATCTATCGAT TGTCAGGAGG (SEQ ID N. 136) | CATTGTGGGCTCA CTCTGCTGCA (SEQ ID N. 137) | CTGAGATGAGCTT TCTGGAGAGTCA (SEQ ID N. 138) |

Mismatched 5'-G are indicated in lowercase. Mutations are indicated in bold. PAM included in the target sequences.

The invention claimed is:

1. A polypeptide having Cas9 endonuclease activity comprising an amino acid sequence having at least 90% sequence identity to SEQ ID NO:1 and having a K526 mutation, wherein the position of the K526 mutation is identified by reference to the amino acid numbering in SEQ ID NO:1, and wherein the polypeptide has a higher Cas9 on-target/off-target activity ratio than the polypeptide of SEQ ID NO: 1.

2. The polypeptide of claim 1, wherein the mutation at position K526 is K526E or K526N.

3. The polypeptide of claim 1, wherein the polypeptide comprises an amino acid sequence having at least 95% sequence identity to SEQ ID NO: 1.

4. The polypeptide of claim 3, wherein the K526 mutation is a K526E mutation.

5. The polypeptide of claim 3, wherein the polypeptide comprises K526E+M495V+Y515N+R661Q mutations.

6. The polypeptide of claim 1, wherein the K526 mutation is a K526E mutation.

7. The polypeptide of claim 6, further comprising one or more mutations located at one or more amino acid residue positions selected from K377, D397, R400, Q402, R403, F405, D406, N407, A421, L423, Y430, P449, Y450, W464, M465, E470, T472, I473, T474, P475, W476, F478, K484, S487, A488, M495, T496, F498, N504, P509, Y515, F518, N522, E523, L540, S541, I548, D550, F553, V561, K562, E573, A589, L598, D605, L607, N609, N612, R629, K637, L651, K652, R654, T657, G658, W659, R661, L666, K673, S675, I679, L683, N690, R691, Q695, H698, F704, Q712, G715, Q716, H721, H723, I724, L727, A728, I733, L738, and Q739, wherein the positions of the one or more further mutations are identified by reference to the amino acid numbering in SEQ ID NO:1.

8. The polypeptide of claim 7, wherein the one or more further mutations are selected from K377E, D397E, R400H, Q402R, R403H, F405L, D406Y, D406V, N407P, N407H, A421V, L423P, Y430C, P449S, Y450A, Y450S, Y450H, Y450N, W464L, M465R, E470D, T472A, I473F, I473V, T474A, P475H, W476R, F478Y, F478V, K484M, S487Y, A488V, M495V, M495T, T496A, F498I, F498Y, N504S, P509L, Y515N, F518L, F518I, N522K, N522I, E523K, E523D, L540Q, S541P, I548V, D550N, F553L, V561M, V561A, K562E, E573D, A589T, L598P, D605V, L607P, N609D, N609S, N612Y, N612K, R629G, K637N, L651P, L651H, K652E, R654H, T657A, G658E, W659R, R661A, R661W, R661L, R661Q, R661S, L666P, K673M, S675C, I679V, L683P, N690I, R691Q, R691L, Q695A, Q695H, Q695L, H698Q, H698P, F704S, Q712R, G715S, Q716H, H721R, H723L, I724V, L727H, A728G, A728T, I733V, L738P, Q739E, Q739P and Q739K.

9. The polypeptide of claim 7, wherein the one or more further mutations are at one or more positions selected from Y450, M495, Y515, R661, N690, R691, Q695, and H698.

10. The polypeptide of claim 9, wherein the one or more further mutations are selected from Y450S, M495V, Y515N, R661X, N690I, R691Q, Q695H and H698Q, where X is L, Q or S.

11. The polypeptide of claim 1, wherein the polypeptide comprises K526E+M495V+Y515N+R661Q mutations.

12. The polypeptide of claim 1, which comprises:
(a) K526E+Y450S mutations;
(b) K526E+M495V mutations;
(c) K526E+Y515N mutations;
(d) K526E+R661L mutations;
(e) K526E+N690I mutations;
(f) K526E+R691Q mutations;
(g) K526E+Q695H mutations;
(h) K526E+H698Q mutations;
(i) K526E+Y515N+R661X mutations;
(j) K526E+R661L+H698Q mutations;
(k) K526E+M495V+Y515N mutations;
(l) K526E+M495V+R661L mutations;
(m) K526E+M495V+R661X+H698Q mutations;
(n) K526E+M495V+Y515N+R661X mutations; or
(o) K526E+R403H+N612Y+L651P+K652E+G715S mutations;
wherein X is L, Q or S.

13. The polypeptide of claim 12, which comprises:
(a) K526E+Y515N+R661L mutations;
(b) K526E+Y515N+R661Q mutations;
(c) K526E+Y515N+R661S mutations;
(d) K526E+M495V+R661L+H698Q mutations;
(e) K526E+M495V+R661Q+H698Q mutations;
(f) K526E+M495V+R661S+H698Q mutations;
(g) K526E+M495V+Y515N+R661L mutations;
(h) K526E+M495V+Y515N+R661Q mutations; or
(i) K526E+M495V+Y515N+R661S mutations.

14. polypeptide of claim 13, which comprises K526E+M495V+Y515N+R661S mutations.

15. The polypeptide of claim 1, which comprises:
M495V+K526N+S541P+K562E mutations; or
R403H+K526E+N612Y+L651P+K652E+G715S mutations.

16. A ribonucleoprotein (RNP) complex comprising the polypeptide of claim 1.

17. A fusion protein comprising polypeptide of claim 1.

18. A nucleic acid encoding polypeptide of claim 1.

19. A pharmaceutical composition comprising polypeptide of claim 1 and at least one pharmaceutically acceptable excipient.

20. An in vitro method for altering the genome of a cell, the method comprising expressing in the cell polypeptide of claim 1 together with a guide RNA targeting a specific genomic sequence.

21. A polypeptide comprising an amino acid sequence having K526E+M495V+Y515N+R661Q mutations and that is, other than the K526E+M495V+Y515N+R661Q mutations, 100% identical to SEQ ID NO:1, wherein the positions of the mutations are identified by reference to the amino acid numbering in SEQ ID NO:1.

* * * * *

SEQUENCE LISTING

<160> NUMBER OF SEQ ID NOS: 138

<210> SEQ ID NO 1
<211> LENGTH: 1368
<212> TYPE: PRT
<213> ORGANISM: Streptococcus pyogenes
<300> PUBLICATION INFORMATION:
<308> DATABASE ACCESSION NUMBER: NP_269215
<309> DATABASE ENTRY DATE: 2016-08-03
<313> RELEVANT RESIDUES IN SEQ ID NO: (1)..(1368)

<400> SEQUENCE: 1

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
```

```
                260                 265                 270
Asp Asp Leu Asp Asn Leu Leu Ala Gln Ile Gly Asp Gln Tyr Ala Asp
        275                 280                 285
Leu Phe Leu Ala Ala Lys Asn Leu Ser Asp Ala Ile Leu Leu Ser Asp
        290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
                340                 345                 350
Asp Gln Ser Lys Asn Gly Tyr Ala Gly Tyr Ile Asp Gly Gly Ala Ser
                355                 360                 365
Gln Glu Glu Phe Tyr Lys Phe Ile Lys Pro Ile Leu Glu Lys Met Asp
                370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
                420                 425                 430
Leu Lys Asp Asn Arg Glu Lys Ile Glu Lys Ile Leu Thr Phe Arg Ile
                435                 440                 445
Pro Tyr Tyr Val Gly Pro Leu Ala Arg Gly Asn Ser Arg Phe Ala Trp
                450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
                500                 505                 510
Leu Leu Tyr Glu Tyr Phe Thr Val Tyr Asn Glu Leu Thr Lys Val Lys
                515                 520                 525
Tyr Val Thr Glu Gly Met Arg Lys Pro Ala Phe Leu Ser Gly Glu Gln
                530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
                580                 585                 590
Thr Tyr His Asp Leu Leu Lys Ile Ile Lys Asp Lys Asp Phe Leu Asp
                595                 600                 605
Asn Glu Glu Asn Glu Asp Ile Leu Glu Asp Ile Val Leu Thr Leu Thr
                610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
                660                 665                 670
Lys Gln Ser Gly Lys Thr Ile Leu Asp Phe Leu Lys Ser Asp Gly Phe
                675                 680                 685
```

-continued

```
Ala Asn Arg Asn Phe Met Gln Leu Ile His Asp Asp Ser Leu Thr Phe
690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
                740                 745                 750
Arg His Lys Pro Glu Asn Ile Val Ile Glu Met Ala Arg Glu Asn Gln
            755                 760                 765
Thr Thr Gln Lys Gly Gln Lys Asn Ser Arg Glu Arg Met Lys Arg Ile
770                 775                 780
Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
                805                 810                 815
Gln Asn Gly Arg Asp Met Tyr Val Asp Gln Glu Leu Asp Ile Asn Arg
                820                 825                 830
Leu Ser Asp Tyr Asp Val Asp His Ile Val Pro Gln Ser Phe Leu Lys
            835                 840                 845
Asp Asp Ser Ile Asp Asn Lys Val Leu Thr Arg Ser Asp Lys Asn Arg
850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
                900                 905                 910
Lys Ala Gly Phe Ile Lys Arg Gln Leu Val Glu Thr Arg Gln Ile Thr
            915                 920                 925
Lys His Val Ala Gln Ile Leu Asp Ser Arg Met Asn Thr Lys Tyr Asp
        930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                980                 985                 990
Val Gly Thr Ala Leu Ile Lys Lys Tyr Pro Lys Leu Glu Ser Glu Phe
            995                 1000                1005
Val Tyr Gly Asp Tyr Lys Val Tyr Asp Val Arg Lys Met Ile Ala
        1010                1015                1020
Lys Ser Glu Gln Glu Ile Gly Lys Ala Thr Ala Lys Tyr Phe Phe
        1025                1030                1035
Tyr Ser Asn Ile Met Asn Phe Phe Lys Thr Glu Ile Thr Leu Ala
        1040                1045                1050
Asn Gly Glu Ile Arg Lys Arg Pro Leu Ile Glu Thr Asn Gly Glu
        1055                1060                1065
Thr Gly Glu Ile Val Trp Asp Lys Gly Arg Asp Phe Ala Thr Val
        1070                1075                1080
Arg Lys Val Leu Ser Met Pro Gln Val Asn Ile Val Lys Lys Thr
        1085                1090                1095
```

| | | | | | | | | | | | |
|---|---|---|---|---|---|---|---|---|---|---|---|
| Glu | Val | Gln | Thr | Gly | Gly | Phe | Ser | Lys | Glu | Ser | Ile | Leu | Pro | Lys |
| 1100 | | | | | 1105 | | | | | 1110 | | | | |

Glu Val Gln Thr Gly Gly Phe Ser Lys Glu Ser Ile Leu Pro Lys
  1100                1105                1110

Arg Asn Ser Asp Lys Leu Ile Ala Arg Lys Lys Asp Trp Asp Pro
  1115                1120                1125

Lys Lys Tyr Gly Gly Phe Asp Ser Pro Thr Val Ala Tyr Ser Val
  1130                1135                1140

Leu Val Val Ala Lys Val Glu Lys Gly Lys Ser Lys Lys Leu Lys
  1145                1150                1155

Ser Val Lys Glu Leu Leu Gly Ile Thr Ile Met Glu Arg Ser Ser
  1160                1165                1170

Phe Glu Lys Asn Pro Ile Asp Phe Leu Glu Ala Lys Gly Tyr Lys
  1175                1180                1185

Glu Val Lys Lys Asp Leu Ile Ile Lys Leu Pro Lys Tyr Ser Leu
  1190                1195                1200

Phe Glu Leu Glu Asn Gly Arg Lys Arg Met Leu Ala Ser Ala Gly
  1205                1210                1215

Glu Leu Gln Lys Gly Asn Glu Leu Ala Leu Pro Ser Lys Tyr Val
  1220                1225                1230

Asn Phe Leu Tyr Leu Ala Ser His Tyr Glu Lys Leu Lys Gly Ser
  1235                1240                1245

Pro Glu Asp Asn Glu Gln Lys Gln Leu Phe Val Glu Gln His Lys
  1250                1255                1260

His Tyr Leu Asp Glu Ile Ile Glu Gln Ile Ser Glu Phe Ser Lys
  1265                1270                1275

Arg Val Ile Leu Ala Asp Ala Asn Leu Asp Lys Val Leu Ser Ala
  1280                1285                1290

Tyr Asn Lys His Arg Asp Lys Pro Ile Arg Glu Gln Ala Glu Asn
  1295                1300                1305

Ile Ile His Leu Phe Thr Leu Thr Asn Leu Gly Ala Pro Ala Ala
  1310                1315                1320

Phe Lys Tyr Phe Asp Thr Thr Ile Asp Arg Lys Arg Tyr Thr Ser
  1325                1330                1335

Thr Lys Glu Val Leu Asp Ala Thr Leu Ile His Gln Ser Ile Thr
  1340                1345                1350

Gly Leu Tyr Glu Thr Arg Ile Asp Leu Ser Gln Leu Gly Gly Asp
  1355                1360                1365

<210> SEQ ID NO 2
<211> LENGTH: 4107
<212> TYPE: DNA
<213> ORGANISM: Streptococcus pyogenes
<300> PUBLICATION INFORMATION:
<308> DATABASE ACCESSION NUMBER: NC_002737.2
<309> DATABASE ENTRY DATE: 2016-08-03
<313> RELEVANT RESIDUES IN SEQ ID NO: (854751)..(858857)

<400> SEQUENCE: 2

```
atggataaga aatactcaat aggcttagat atcggcacaa atagcgtcgg atgggcggtg      60
atcactgatg aatataaggt tccgtctaaa aagttcaagg ttctgggaaa tacagaccgc     120
cacagtatca aaaaaatct tataggggct cttttatttg acagtggaga cagcggaa       180 gcgactcgtc tcaaacggac agctcgtaga aggtatacac gtcggaagaa tcgtatttgt     240
tatctacagg agattttttc aaatgagatg gcgaaagtag atgatagttt ctttcatcga     300
cttgaagagt cttttttggt ggaagaagac aagaagcatg aacgtcatcc tatttttgga     360
aatatagtag atgaagttgc ttatcatgag aaatatccaa ctatctatca tctgcgaaaa     420
```

```
aaattggtag attctactga taaagcggat ttgcgcttaa tctatttggc cttagcgcat      480
atgattaagt ttcgtggtca ttttttgatt gagggagatt taaatcctga taatagtgat      540
gtggacaaac tatttatcca gttggtacaa acctacaatc aattatttga agaaaaccct      600
attaacgcaa gtggagtaga tgctaaagcg attctttctg cacgattgag taaatcaaga      660
cgattagaaa atctcattgc tcagctcccc ggtgagaaga aaaatggctt atttgggaat      720
ctcattgctt tgtcattggg tttgacccct aattttaaat caaattttga tttggcagaa      780
gatgctaaat tacagctttc aaaagatact tacgatgatg atttagataa tttattggcg      840
caaattggag atcaatatgc tgatttgttt ttggcagcta agaatttatc agatgctatt      900
ttactttcag atatcctaag agtaaatact gaaataacta aggctcccct atcagcttca      960
atgattaaac gctacgatga acatcatcaa gacttgactc ttttaaaagc tttagttcga     1020
caacaacttc cagaaaagta taagaaaatc ttttttgatc aatcaaaaaa cggatatgca     1080
ggttatattg atgggggagc tagccaagaa gaattttata aatttatcaa accaattttt     1140
gaaaaaatgg atggtactga ggaattattg gtgaaactaa atcgtgaaga tttgctgcgc     1200
aagcaacgga cctttgacaa cggctctatt ccccatcaaa ttcacttggg tgagctgcat     1260
gctattttga agacaagaa gactttttat ccatttttaa aagacaatcg tgagaagatt     1320
gaaaaaatct tgacttttcg aattccttat tatgttggtc cattggcgcg tggcaatagt     1380
cgttttgcat ggatgactcg gaagtctgaa gaaacaatta ccccatggaa ttttgaagaa     1440
gttgtcgata aggtgcttc agctcaatca tttattgaac gcatgacaaa ctttgataaa     1500
aatcttccaa atgaaaaagt actaccaaaa catagtttgc tttatgagta ttttacggtt     1560
tataacgaat tgacaaaggt caaatatgtt actgaaggaa tgcgaaaacc agcatttctt     1620
tcaggtgaac agaagaaagc cattgttgat ttactcttca aaacaaatcg aaaagtaacc     1680
gttaagcaat aaaagaaga ttatttcaaa aaaatagaat gttttgatag tgttgaaatt     1740
tcaggagttg aagatagatt taatgcttca ttaggtacct accatgattt gctaaaaatt     1800
attaaagata aagatttttt ggataatgaa gaaaatgaag atatcttaga ggatattgtt     1860
ttaacattga ccttatttga agatagggag atgattgagg aaagacttaa aacatatgct     1920
cacctctttg atgataaggt gatgaaacag cttaaacgtc gccgttatac tggttgggga     1980
cgtttgtctc gaaaattgat taatggtatt agggataagc aatctggcaa aacaatatta     2040
gattttttga atcagatgg ttttgccaat cgcaattta tgcagctgat ccatgatgat     2100
agtttgacat ttaaagaaga cattcaaaaa gcacaagtgt ctggacaagg cgatagttta     2160
catgaacata ttgcaaattt agctggtagc cctgctatta aaaaggtat tttacagact     2220 gtaaaagttg ttgatgaatt ggtcaaagta atggggcggc ataagccaga aaatatcgtt     2280
attgaaatgg cacgtgaaaa tcagacaact caaaagggcc agaaaaattc gcgagagcgt     2340
atgaaacgaa tcgaagaagg tatcaaagaa ttaggaagtc agattcttaa agagcatcct     2400
gttgaaaata ctcaattgca aaatgaaaag ctctatctct attatctcca aaatggaaga     2460
gacatgtatg tggaccaaga attagatatt aatcgtttaa gtgattatga tgtcgatcac     2520
attgttccac aaagtttcct taaagacgat tcaatagaca ataaggtctt aacgcgttct     2580
gataaaaatc gtggtaaatc ggataacgtt ccaagtgaag aagtagtcaa aaagatgaaa     2640
aactattgga gacaacttct aaacgccaag ttaatcactc aacgtaagtt tgataattta     2700
acgaaagctg aacgtggagg tttgagtgaa cttgataaag ctggttttat caaacgccaa     2760
```

```
ttggttgaaa ctcgccaaat cactaagcat gtggcacaaa ttttggatag tcgcatgaat    2820
actaaatacg atgaaaatga taaacttatt cgagaggtta aagtgattac cttaaaatct    2880
aaattagttt ctgacttccg aaaagatttc caattctata agtacgtga gattaacaat     2940 taccatcatg cccatgatgc gtatctaaat gccgtcgttg gaactgcttt gattaagaaa    3000
tatccaaaac ttgaatcgga gtttgtctat ggtgattata agtttatga tgttcgtaaa     3060 atgattgcta agtctgagca agaaataggc aaagcaaccg caaaatattt ctttttactct   3120 aatatcatga acttcttcaa aacagaaatt acacttgcaa atggagagat tcgcaaacgc    3180
cctctaatcg aaactaatgg ggaaactgga gaaattgtct gggataaagg gcgagatttt    3240
gccacagtgc gcaaagtatt gtccatgccc caagtcaata ttgtcaagaa aacagaagta    3300
cagacaggcg gattctccaa ggagtcaatt ttaccaaaaa gaaattcgga caagcttatt    3360
gctcgtaaaa aagactggga tccaaaaaaa tatggtggtt ttgatagtcc aacggtagct    3420
tattcagtcc tagtggttgc taaggtggaa aaagggaaat cgaagaagtt aaaatccgtt    3480
aaagagttac tagggatcac aattatgaaa agaagttcct ttgaaaaaaa tccgattgac    3540
tttttagaag ctaaaggata taaggaagtt aaaaaagact taatcattaa actacctaaa    3600
tatagtcttt ttgagttaga aaacggtcgt aaacggatgc tggctagtgc cggagaatta    3660
caaaaaggaa atgagctggc tctgccaagc aaatatgtga attttttata tttagctagt    3720
cattatgaaa agttgaaggg tagtccagaa gataacgaac aaaaacaatt gtttgtggag    3780
cagcataagc attatttaga tgagattatt gagcaaatca gtgaattttc taagcgtgtt    3840
attttagcag atgccaattt agataaagtt cttagtgcat ataacaaaca tagagacaaa    3900
ccaatacgtg aacaagcaga aaatattatt catttattta cgttgacgaa tcttggagct    3960
cccgctgctt ttaaatattt tgatacaaca attgatcgta aacgatatac gtctacaaaa    4020
gaagttttag atgccactct tatccatcaa tccatcactg gtctttatga aacacgcatt    4080
gatttgagtc agctaggagg tgactga                                         4107

<210> SEQ ID NO 3
<211> LENGTH: 4107
<212> TYPE: DNA
<213> ORGANISM: Streptococcus pyogenes

<400> SEQUENCE: 3
atggacaaga agtacagcat cggcctggac atcggcacca actctgtggg ctgggccgtg     60
atcaccgacg agtacaaggt gcccagcaag aaattcaagg tgctgggcaa caccgaccgg    120
cacagcatca agaagaacct gatcggagcc ctgctgttcg acagcggcga aacagccgag    180
gccacccggc tgaagagaac cgccagaaga agatacacca cacggaagaa ccggatctgc    240
tatctgcaag agatcttcag caacgagatg gccaaggtgg acgacagctt cttccacaga    300
ctggaagagt ccttcctggt ggaagaggat aagaagcacg agcggcaccc catcttcggc    360
aacatcgtgg acgaggtggc ctaccacgag aagtacccca catctacca cctgagaaag    420 aaactggtgg acagcaccga caaggccgac ctgcggctga tctatctggc cctggcccac    480
atgatcaagt tccggggcca cttcctgatc gagggcgacc tgaaccccga caacagcgac    540
gtggacaagc tgttcatcca gctggtgcag acctacaacc agctgttcga ggaaaacccc    600
atcaacgcca gcggcgtgga cgccaaggcc atcctgtctg ccagactgag caagagcaga    660
cggctggaaa atctgatcgc ccagctgccc ggcgagaaga agaatggcct gttcggaaac    720
ctgattgccc tgagcctggg cctgaccccc aacttcaaga gcaacttcga cctggccgag    780
```

```
gatgccaaac tgcagctgag caaggacacc tacgacgacg acctggacaa cctgctggcc    840
cagatcggcg accagtacgc cgacctgttt ctggccgcca agaacctgtc cgacgccatc    900
ctgctgagcg acatcctgag agtgaacacc gagatcacca aggcccccct gagcgcctct    960
atgatcaaga gatacgacga gcaccaccag gacctgaccc tgctgaaagc tctcgtgcgg   1020
cagcagctgc ctgagaagta caaagagatt ttcttcgacc agagcaagaa cggctacgcc   1080
ggctacattg acggcggagc cagccaggaa gagttctaca agttcatcaa gcccatcctg   1140
gaaaagatgg acggcaccga ggaactgctc gtgaagctga acagagagga cctgctgcgg   1200
aagcagcgga ccttcgacaa cggcagcatc ccccaccaga tccacctggg agagctgcac   1260
gccattctgc ggcggcagga agatttttac ccattcctga aggacaaccg ggaaaagatc   1320
gagaagatcc tgacctttccg catcccctac tacgtgggcc ctctggccag ggaaacagc    1380 agattcgcct ggatgaccag aaagagcgag gaaaccatca ccccctggaa cttcgaggaa   1440
gtggtggaca agggcgcttc cgcccagagc ttcatcgagc ggatgaccaa cttcgataag   1500
aacctgccca acgagaaggt gctgcccaag cacagcctgc tgtacgagta cttcaccgtg   1560
tataacgagc tgaccaaagt gaaatacgtg accgagggaa tgagaaagcc cgccttcctg   1620
agcggcgagc agaaaaaggc catcgtggac ctgctgttca gaccaaccg gaaagtgacc    1680 gtgaagcagc tgaaagagga ctacttcaag aaaatcgagt gcttcgactc cgtggaaatc   1740
tccggcgtgg aagatcggtt caacgcctcc ctgggcacat accacgatct gctgaaaatt   1800
atcaaggaca aggacttcct ggacaatgag gaaaacgagg acattctgga agatatcgtg   1860
ctgaccctga cactgtttga ggacagagag atgatcgagg aacggctgaa aacctatgcc   1920
cacctgttcg acgacaaagt gatgaagcag ctgaagcggc ggagatacac cggctggggc   1980
aggctgagcc ggaagctgat caacggcatc cgggacaagc agtccggcaa gacaatcctg   2040
gatttcctga gtccgacgg cttcgccaac agaaacttca tgcagctgat ccacgacgac   2100
agcctgacct ttaaagagga catccagaaa gcccaggtgt ccggccaggg cgatagcctg   2160
cacgagcaca ttgccaatct ggccggcagc cccgccatta agaagggcat cctgcagaca   2220
gtgaaggtgg tggacgagct cgtgaaagtg atgggccggc acaagcccga aacatcgtg    2280 atcgaaatgg ccagagagaa ccagaccacc cagaagggac agaagaacag ccgcgagaga   2340
atgaagcgga tcgaagaggg catcaaagag ctgggcagcc agatcctgaa agaacacccc   2400
gtggaaaaca cccagctgca gaacgagaag ctgtacctgt actacctgca gaatgggcgg   2460
gatatgtacg tggaccagga actggacatc aaccggctgt ccgactacga tgtggaccat   2520
atcgtgcctc agagctttct gaaggacgac tccatcgaca caaggtgct gaccagaagc    2580 gacaagaacc ggggcaagag cgacaacgtg ccctccgaag aggtcgtgaa aagatgaag    2640 aactactggc ggcagctgct gaacgccaag ctgattaccc agagaaagtt cgacaatctg   2700
accaaggccg agagaggcgg cctgagcgaa ctggataagg ccggcttcat caagagacag   2760
ctggtggaaa cccggcagat cacaaagcac gtggcacaga tcctggactc cggatgaac    2820 actaagtacg acgagaatga caagctgatc cgggaagtga aagtgatcac cctgaagtcc   2880
aagctggtgt ccgatttccg gaaggatttc cagtttttaca agtgcgcga gatcaacaac    2940 taccaccacg cccacgacgc ctacctgaac gccgtcgtgg aaccgccct gatcaaaaag   3000 taccctaagc tggaaagcga gttcgtgtac ggcgactaca aggtgtacga cgtgcggaag   3060
atgatcgcca agagcgagca ggaaatcggc aaggctaccg ccaagtactt cttctacagc   3120
```

```
aacatcatga acttttttcaa gaccgagatt accctggcca acggcgagat ccggaagcgg    3180
cctctgatcg agacaaacgg cgaaaccggg gagatcgtgt gggataaggg ccgggatttt    3240
gccaccgtgc ggaaagtgct gagcatgccc caagtgaata tcgtgaaaaa gaccgaggtg    3300
cagacaggcg gcttcagcaa agagtctatc ctgcccaaga ggaacagcga taagctgatc    3360
gccagaaaga aggactggga ccctaagaag tacgcggct tcgacagccc caccgtggcc     3420
tattctgtgc tggtggtggc caaagtgaaa aagggcaagt ccaagaaact gaagagtgtg    3480
aaagagctgc tggggatcac catcatggaa agaagcagct tcgagaagaa tcccatcgac    3540
tttctggaag ccaagggcta caagaagtg aaaaaggacc tgatcatcaa gctgcctaag     3600
tactccctgt tcgagctgga aaacggccgg aagagaatgc tggcctctgc cggcgaactg    3660
cagaagggaa acgaactggc cctgccctcc aaatatgtga acttcctgta cctggccagc    3720
cactatgaga agctgaaggg ctcccccgag gataatgagc agaaacagct gtttgtggaa    3780
cagcacaagc actacctgga cgagatcatc gagcagatca gcgagttctc caagagagtg    3840
atcctggccg acgctaatct ggacaaagtg ctgtccgcct acaacaagca ccgggataag    3900
cccatcagag agcaggccga gaatatcatc cacctgttta ccctgaccaa tctgggagcc    3960
cctgccgcct tcaagtactt tgacaccacc atcgaccgga gaggtacac cagcaccaaa     4020 gaggtgctgg acgccaccct gatccaccag agcatcaccg gcctgtacga gacacggatc    4080
gacctgtctc agctgggagg cgactaa                                        4107

<210> SEQ ID NO 4
<211> LENGTH: 35
<212> TYPE: DNA
<213> ORGANISM: Artificial Sequence
<220> FEATURE:
<223> OTHER INFORMATION: Synthetic construct

<400> SEQUENCE: 4
ccagaaagca caagttgcta gccagggga cagtc                                35

<210> SEQ ID NO 5
<211> LENGTH: 35
<212> TYPE: DNA
<213> ORGANISM: Artificial Sequence
<220> FEATURE:
<223> OTHER INFORMATION: Synthetic construct

<400> SEQUENCE: 5
gactgtcccc ctggctagca acttgtgctt tctgg                               35

<210> SEQ ID NO 6
<211> LENGTH: 32
<212> TYPE: DNA
<213> ORGANISM: Artificial Sequence
<220> FEATURE:
<223> OTHER INFORMATION: Synthetic construct

<400> SEQUENCE: 6
cagcgcactt tcgaccatgg aagcatcccc ca                                  32

<210> SEQ ID NO 7
<211> LENGTH: 32
<212> TYPE: DNA
<213> ORGANISM: Artificial Sequence
<220> FEATURE:
<223> OTHER INFORMATION: Synthetic construct

<400> SEQUENCE: 7
```

```
tgggggatgc ttccatggtc gaaagtgcgc tg                                    32
```

<210> SEQ ID NO 8
<211> LENGTH: 20
<212> TYPE: DNA
<213> ORGANISM: Artificial Sequence
<220> FEATURE:
<223> OTHER INFORMATION: Serratia phage SM9-3Y, 9162-9181
<300> PUBLICATION INFORMATION:
<308> DATABASE ACCESSION NUMBER: KX778611.1
<309> DATABASE ENTRY DATE: 2017-01-17
<313> RELEVANT RESIDUES IN SEQ ID NO: (9162)..(9181)

<400> SEQUENCE: 8

```
aattaaccct cactaaaggg                                                  20
```

<210> SEQ ID NO 9
<211> LENGTH: 20
<212> TYPE: DNA
<213> ORGANISM: Artificial Sequence
<220> FEATURE:
<223> OTHER INFORMATION: Escherichia coli strain Y5, 1391073-1391092
<300> PUBLICATION INFORMATION:
<308> DATABASE ACCESSION NUMBER: CP013483.1
<309> DATABASE ENTRY DATE: 2016-11-01
<313> RELEVANT RESIDUES IN SEQ ID NO: (1391073)..(1391092)

<400> SEQUENCE: 9

```
taatacgact cactataggg                                                  20
```

<210> SEQ ID NO 10
<211> LENGTH: 42
<212> TYPE: DNA
<213> ORGANISM: Artificial Sequence
<220> FEATURE:
<223> OTHER INFORMATION: Synthetic construct

<400> SEQUENCE: 10

```
ctcgtgacca ccctgaccta gttttagagc tagaaatagc aa                         42
```

<210> SEQ ID NO 11
<211> LENGTH: 41
<212> TYPE: DNA
<213> ORGANISM: Artificial Sequence
<220> FEATURE:
<223> OTHER INFORMATION: Synthetic construct

<400> SEQUENCE: 11

```
taggtcaggg tggtcacgag gatcatttat ctttcactgc g                          41
```

<210> SEQ ID NO 12
<211> LENGTH: 19
<212> TYPE: DNA
<213> ORGANISM: Artificial Sequence
<220> FEATURE:
<223> OTHER INFORMATION: Synthetic construct

<400> SEQUENCE: 12

```
acgtgggccc tctggccag                                                   19
```

<210> SEQ ID NO 13
<211> LENGTH: 31
<212> TYPE: DNA
<213> ORGANISM: Artificial Sequence
<220> FEATURE:
<223> OTHER INFORMATION: Synthetic construct

<400> SEQUENCE: 13
tacgctagct cccttttcct tttttgcctg g               31

<210> SEQ ID NO 14
<211> LENGTH: 26
<212> TYPE: DNA
<213> ORGANISM: Artificial Sequence
<220> FEATURE:
<223> OTHER INFORMATION: Synthetic construct

<400> SEQUENCE: 14
attagggccc cctggcccga gggaac                    26

<210> SEQ ID NO 15
<211> LENGTH: 31
<212> TYPE: DNA
<213> ORGANISM: Artificial Sequence
<220> FEATURE:
<223> OTHER INFORMATION: Synthetic construct

<400> SEQUENCE: 15
taatactagt gactttcctc ttcttcttgg g              31

<210> SEQ ID NO 16
<211> LENGTH: 19
<212> TYPE: DNA
<213> ORGANISM: Artificial Sequence
<220> FEATURE:
<223> OTHER INFORMATION: Saccharomyces cerevisiae YJM1549 chromosome IV
<300> PUBLICATION INFORMATION:
<308> DATABASE ACCESSION NUMBER: CP004747.2
<309> DATABASE ENTRY DATE: 2016-09-16
<313> RELEVANT RESIDUES IN SEQ ID NO: (453079)..(453097)

<400> SEQUENCE: 16
ccaagaggga gggcattgg                            19

<210> SEQ ID NO 17
<211> LENGTH: 55
<212> TYPE: DNA
<213> ORGANISM: Artificial Sequence
<220> FEATURE:
<223> OTHER INFORMATION: Synthetic construct

<400> SEQUENCE: 17
tgcggtaccg taggtcaggg tggtcacgag ttagaggaac tcttggtatt cttgc     55

<210> SEQ ID NO 18
<211> LENGTH: 33
<212> TYPE: DNA
<213> ORGANISM: Artificial Sequence
<220> FEATURE:
<223> OTHER INFORMATION: Synthetic construct

<400> SEQUENCE: 18
ttaggtaccg taatcaacct aaggaggatg ttt             33

<210> SEQ ID NO 19
<211> LENGTH: 22
<212> TYPE: DNA
<213> ORGANISM: Artificial Sequence
<220> FEATURE:
<223> OTHER INFORMATION: Saccharomyces cerevisiae YJM1549 chromosome IV
<300> PUBLICATION INFORMATION:
<308> DATABASE ACCESSION NUMBER: CP004747.2
<309> DATABASE ENTRY DATE: 2016-09-16
<313> RELEVANT RESIDUES IN SEQ ID NO: (453875)..(453896)

-continued

```
<400> SEQUENCE: 19
tgcttgcttt tcaaaaggcc tg                                              22

<210> SEQ ID NO 20
<211> LENGTH: 26
<212> TYPE: DNA
<213> ORGANISM: Artificial Sequence
<220> FEATURE:
<223> OTHER INFORMATION: Saccharomyces cerevisiae YJM1574 chromosome XV
<300> PUBLICATION INFORMATION:
<308> DATABASE ACCESSION NUMBER: CP005677.2
<309> DATABASE ENTRY DATE: 2016-11-22
<313> RELEVANT RESIDUES IN SEQ ID NO: (548437)..(548462)

<400> SEQUENCE: 20
tgcctagttt catgaaattt taaagc                                          26

<210> SEQ ID NO 21
<211> LENGTH: 53
<212> TYPE: DNA
<213> ORGANISM: Artificial Sequence
<220> FEATURE:
<223> OTHER INFORMATION: Synthetic construct

<400> SEQUENCE: 21
ccaggatccg gaggtcaggg tggtcacgag ttagacgcaa gcatcaatgg tat            53

<210> SEQ ID NO 22
<211> LENGTH: 53
<212> TYPE: DNA
<213> ORGANISM: Artificial Sequence
<220> FEATURE:
<223> OTHER INFORMATION: Synthetic construct

<400> SEQUENCE: 22
ccaggatccg taggtaaggg tggtcacgag ttagacgcaa gcatcaatgg tat            53

<210> SEQ ID NO 23
<211> LENGTH: 53
<212> TYPE: DNA
<213> ORGANISM: Artificial Sequence
<220> FEATURE:
<223> OTHER INFORMATION: Synthetic construct

<400> SEQUENCE: 23
ccaggatccg taggtcaggg cggtcacgag ttagacgcaa gcatcaatgg tat            53

<210> SEQ ID NO 24
<211> LENGTH: 53
<212> TYPE: DNA
<213> ORGANISM: Artificial Sequence
<220> FEATURE:
<223> OTHER INFORMATION: Synthetic construct

<400> SEQUENCE: 24
ccaggatccg taggtcaggg tggtaacgag ttagacgcaa gcatcaatgg tat            53

<210> SEQ ID NO 25
<211> LENGTH: 33
<212> TYPE: DNA
<213> ORGANISM: Artificial Sequence
<220> FEATURE:
<223> OTHER INFORMATION: Synthetic construct

<400> SEQUENCE: 25
```
attaggatcc tggtgtggaa atgttctatt tag                                    33

<210> SEQ ID NO 26
<211> LENGTH: 27
<212> TYPE: DNA
<213> ORGANISM: Artificial Sequence
<220> FEATURE:
<223> OTHER INFORMATION: Saccharomyces cerevisiae YJM1574 chromosome XV
<300> PUBLICATION INFORMATION:
<308> DATABASE ACCESSION NUMBER: CP005677.2
<309> DATABASE ENTRY DATE: 2016-11-22
<313> RELEVANT RESIDUES IN SEQ ID NO: (546227)..(546253)

<400> SEQUENCE: 26
gtaatcataa caaagcctaa aaaatag                                          27

<210> SEQ ID NO 27
<211> LENGTH: 88
<212> TYPE: DNA
<213> ORGANISM: Artificial Sequence
<220> FEATURE:
<223> OTHER INFORMATION: Synthetic construct

<400> SEQUENCE: 27
tattgagcac gtgagtatac gtgattaagc acacaaaggc agcttggagt tagggataac      60
agggtaattt ggatggacgc aaagaagt                                         88

<210> SEQ ID NO 28
<211> LENGTH: 70
<212> TYPE: DNA
<213> ORGANISM: Artificial Sequence
<220> FEATURE:
<223> OTHER INFORMATION: Synthetic construct

<400> SEQUENCE: 28
tgcaggcaag tgcacaaaca atacttaaat aaatactact cagtaataac ttcgtacgct      60
gcaggtcgac                                                             70

<210> SEQ ID NO 29
<211> LENGTH: 88
<212> TYPE: DNA
<213> ORGANISM: Artificial Sequence
<220> FEATURE:
<223> OTHER INFORMATION: Synthetic construct

<400> SEQUENCE: 29
cctactataa caatcaagaa aaacaagaaa atcggacaaa acaatcaagt tagggataac      60
agggtaattt ggatggacgc aaagaagt                                         88

<210> SEQ ID NO 30
<211> LENGTH: 70
<212> TYPE: DNA
<213> ORGANISM: Artificial Sequence
<220> FEATURE:
<223> OTHER INFORMATION: Synthetic construct

<400> SEQUENCE: 30
atatcatttt ataattattt gctgtacaag tatatcaata aacttatata ttcgtacgct      60
gcaggtcgac                                                             70

<210> SEQ ID NO 31
<211> LENGTH: 23
<212> TYPE: DNA
<213> ORGANISM: Artificial Sequence

```
<220> FEATURE:
<223> OTHER INFORMATION: Synthetic construct

<400> SEQUENCE: 31
ctcgtgacca ccctgaccta cgg                                            23

<210> SEQ ID NO 32
<211> LENGTH: 23
<212> TYPE: DNA
<213> ORGANISM: Artificial Sequence
<220> FEATURE:
<223> OTHER INFORMATION: Synthetic construct

<400> SEQUENCE: 32
ctcgtgacca ccctgacctc cgg                                            23

<210> SEQ ID NO 33
<211> LENGTH: 23
<212> TYPE: DNA
<213> ORGANISM: Artificial Sequence
<220> FEATURE:
<223> OTHER INFORMATION: Synthetic construct

<400> SEQUENCE: 33
ctcgtgacca cccttaccta cgg                                            23

<210> SEQ ID NO 34
<211> LENGTH: 23
<212> TYPE: DNA
<213> ORGANISM: Artificial Sequence
<220> FEATURE:
<223> OTHER INFORMATION: Synthetic construct

<400> SEQUENCE: 34
ctcgtgaccg ccctgaccta cgg                                            23

<210> SEQ ID NO 35
<211> LENGTH: 23
<212> TYPE: DNA
<213> ORGANISM: Artificial Sequence
<220> FEATURE:
<223> OTHER INFORMATION: Synthetic construct

<400> SEQUENCE: 35
ctcgttacca ccctgaccta cgg                                            23

<210> SEQ ID NO 36
<211> LENGTH: 50
<212> TYPE: DNA
<213> ORGANISM: Artificial Sequence
<220> FEATURE:
<223> OTHER INFORMATION: Synthetic construct

<400> SEQUENCE: 36
gtctaaaaat ggctacgccg gatacattga cggcggagca agccaggagg               50

<210> SEQ ID NO 37
<211> LENGTH: 50
<212> TYPE: DNA
<213> ORGANISM: Artificial Sequence
<220> FEATURE:
<223> OTHER INFORMATION: Synthetic construct

<400> SEQUENCE: 37
tctcgggcca tctcgataac gatattctcg ggcttatgcc ttcccattac               50
```

```
<210> SEQ ID NO 38
<211> LENGTH: 20
<212> TYPE: DNA
<213> ORGANISM: Artificial Sequence
<220> FEATURE:
<223> OTHER INFORMATION: Synthetic construct

<400> SEQUENCE: 38
gggcacgggc agcttgccgg                                                 20

<210> SEQ ID NO 39
<211> LENGTH: 20
<212> TYPE: DNA
<213> ORGANISM: Artificial Sequence
<220> FEATURE:
<223> OTHER INFORMATION: Synthetic construct

<400> SEQUENCE: 39
gggcacccgc agcttgccgg                                                 20

<210> SEQ ID NO 40
<211> LENGTH: 20
<212> TYPE: DNA
<213> ORGANISM: Artificial Sequence
<220> FEATURE:
<223> OTHER INFORMATION: Synthetic construct

<400> SEQUENCE: 40
gcccacgggc agcttgccgg                                                 20

<210> SEQ ID NO 41
<211> LENGTH: 20
<212> TYPE: DNA
<213> ORGANISM: Artificial Sequence
<220> FEATURE:
<223> OTHER INFORMATION: Synthetic construct

<400> SEQUENCE: 41
ggccacgggc agcttgccgg                                                 20

<210> SEQ ID NO 42
<211> LENGTH: 20
<212> TYPE: DNA
<213> ORGANISM: Artificial Sequence
<220> FEATURE:
<223> OTHER INFORMATION: Synthetic construct

<400> SEQUENCE: 42
gtcgccctcg aacttcacct                                                 20

<210> SEQ ID NO 43
<211> LENGTH: 20
<212> TYPE: DNA
<213> ORGANISM: Artificial Sequence
<220> FEATURE:
<223> OTHER INFORMATION: Synthetic construct

<400> SEQUENCE: 43
gaagggcatc gacttcaagg                                                 20

<210> SEQ ID NO 44
<211> LENGTH: 20
<212> TYPE: DNA
<213> ORGANISM: Artificial Sequence
<220> FEATURE:
<223> OTHER INFORMATION: Synthetic construct
```

```
<400> SEQUENCE: 44
gctgaagcac tgcacgccgt                                              20

<210> SEQ ID NO 45
<211> LENGTH: 20
<212> TYPE: DNA
<213> ORGANISM: Artificial Sequence
<220> FEATURE:
<223> OTHER INFORMATION: Synthetic construct

<400> SEQUENCE: 45
gaccaggatg ggcaccaccc                                              20

<210> SEQ ID NO 46
<211> LENGTH: 20
<212> TYPE: DNA
<213> ORGANISM: Artificial Sequence
<220> FEATURE:
<223> OTHER INFORMATION: Synthetic construct

<400> SEQUENCE: 46
gaagttcgag ggcgacaccc                                              20

<210> SEQ ID NO 47
<211> LENGTH: 19
<212> TYPE: DNA
<213> ORGANISM: Artificial Sequence
<220> FEATURE:
<223> OTHER INFORMATION: Synthetic construct

<400> SEQUENCE: 47
ggcacgggca gcttgccgg                                               19

<210> SEQ ID NO 48
<211> LENGTH: 18
<212> TYPE: DNA
<213> ORGANISM: Artificial Sequence
<220> FEATURE:
<223> OTHER INFORMATION: Synthetic construct

<400> SEQUENCE: 48
ggcaagctgc ccgtgccc                                                18

<210> SEQ ID NO 49
<211> LENGTH: 17
<212> TYPE: DNA
<213> ORGANISM: Artificial Sequence
<220> FEATURE:
<223> OTHER INFORMATION: Synthetic construct

<400> SEQUENCE: 49
gtgaccaccc tgaccta                                                 17

<210> SEQ ID NO 50
<211> LENGTH: 20
<212> TYPE: DNA
<213> ORGANISM: Artificial Sequence
<220> FEATURE:
<223> OTHER INFORMATION: Synthetic construct

<400> SEQUENCE: 50
gtgatagaga acgtatgtcg                                              20

<210> SEQ ID NO 51
```

<211> LENGTH: 21
<212> TYPE: DNA
<213> ORGANISM: Artificial Sequence
<220> FEATURE:
<223> OTHER INFORMATION: Synthetic construct

<400> SEQUENCE: 51
ggtgatagag aacgtatgtc g                                              21

<210> SEQ ID NO 52
<211> LENGTH: 20
<212> TYPE: DNA
<213> ORGANISM: Artificial Sequence
<220> FEATURE:
<223> OTHER INFORMATION: Synthetic construct

<400> SEQUENCE: 52
gtgatagaga acgtctgtcg                                                20

<210> SEQ ID NO 53
<211> LENGTH: 20
<212> TYPE: DNA
<213> ORGANISM: Artificial Sequence
<220> FEATURE:
<223> OTHER INFORMATION: Synthetic construct

<400> SEQUENCE: 53
gtgatactga acgtatgtcg                                                20

<210> SEQ ID NO 54
<211> LENGTH: 20
<212> TYPE: DNA
<213> ORGANISM: Artificial Sequence
<220> FEATURE:
<223> OTHER INFORMATION: Synthetic construct

<400> SEQUENCE: 54
gacatagaga acgtatgtcg                                                20

<210> SEQ ID NO 55
<211> LENGTH: 33
<212> TYPE: DNA
<213> ORGANISM: Artificial Sequence
<220> FEATURE:
<223> OTHER INFORMATION: Synthetic construct

<400> SEQUENCE: 55
tcgtcggcag cgtcagatgt gtataagaga cag                                 33

<210> SEQ ID NO 56
<211> LENGTH: 34
<212> TYPE: DNA
<213> ORGANISM: Artificial Sequence
<220> FEATURE:
<223> OTHER INFORMATION: Synthetic construct

<400> SEQUENCE: 56
gtctcgtggg ctcggagatg tgtataagag acag                                34

<210> SEQ ID NO 57
<211> LENGTH: 23
<212> TYPE: DNA
<213> ORGANISM: Artificial Sequence
<220> FEATURE:
<223> OTHER INFORMATION: Homo sapiens, chr2:72933853-72933875

<400> SEQUENCE: 57

```
gagtccgagc agaagaagaa ggg                                              23
```

<210> SEQ ID NO 58
<211> LENGTH: 23
<212> TYPE: DNA
<213> ORGANISM: Artificial Sequence
<220> FEATURE:
<223> OTHER INFORMATION: Homo sapiens, chr2:72933807-72933829

<400> SEQUENCE: 58

```
ccggaggaca aagtacaaac ggc                                              23
```

<210> SEQ ID NO 59
<211> LENGTH: 21
<212> TYPE: DNA
<213> ORGANISM: Artificial Sequence
<220> FEATURE:
<223> OTHER INFORMATION: Homo sapiens, chr2:72933973-72933993

<400> SEQUENCE: 59

```
aagcagcact ctgccctcgt g                                                21
```

<210> SEQ ID NO 60
<211> LENGTH: 23
<212> TYPE: DNA
<213> ORGANISM: Artificial Sequence
<220> FEATURE:
<223> OTHER INFORMATION: Homo sapiens, chr5:45358959-45358981

<400> SEQUENCE: 60

```
gagttagagc agaagaagaa agg                                              23
```

<210> SEQ ID NO 61
<211> LENGTH: 25
<212> TYPE: DNA
<213> ORGANISM: Artificial Sequence
<220> FEATURE:
<223> OTHER INFORMATION: Homo sapiens, chr5:45359021-45359045

<400> SEQUENCE: 61

```
cttttatacc atcttggggt tacag                                            25
```

<210> SEQ ID NO 62
<211> LENGTH: 27
<212> TYPE: DNA
<213> ORGANISM: Artificial Sequence
<220> FEATURE:
<223> OTHER INFORMATION: Homo sapiens, chr5:45358831-45358857

<400> SEQUENCE: 62

```
ctaggaaaga ttaacagaga gtctgac                                          27
```

<210> SEQ ID NO 63
<211> LENGTH: 23
<212> TYPE: DNA
<213> ORGANISM: Artificial Sequence
<220> FEATURE:
<223> OTHER INFORMATION: Homo sapiens, chr15:43817549-43817571

<400> SEQUENCE: 63

```
gagtctaagc agaagaagaa gag                                              23
```

<210> SEQ ID NO 64
<211> LENGTH: 24
<212> TYPE: DNA

```
<213> ORGANISM: Artificial Sequence
<220> FEATURE:
<223> OTHER INFORMATION: Homo sapiens, chr15:43817490-43817513

<400> SEQUENCE: 64
caatgtgctt caacccatca cggc                                          24

<210> SEQ ID NO 65
<211> LENGTH: 27
<212> TYPE: DNA
<213> ORGANISM: Artificial Sequence
<220> FEATURE:
<223> OTHER INFORMATION: Homo sapiens, chr15:43817671-43817697

<400> SEQUENCE: 65
cctctacttc attgtactca aggtaag                                       27

<210> SEQ ID NO 66
<211> LENGTH: 23
<212> TYPE: DNA
<213> ORGANISM: Artificial Sequence
<220> FEATURE:
<223> OTHER INFORMATION: Homo sapiens, chr5:9227034-9227056

<400> SEQUENCE: 66
aagtctgagc acaagaagaa tgg                                           23

<210> SEQ ID NO 67
<211> LENGTH: 24
<212> TYPE: DNA
<213> ORGANISM: Artificial Sequence
<220> FEATURE:
<223> OTHER INFORMATION: Homo sapiens, chr5:9226951-9226974

<400> SEQUENCE: 67
tagttctgac attcctcctg aggg                                          24

<210> SEQ ID NO 68
<211> LENGTH: 29
<212> TYPE: DNA
<213> ORGANISM: Artificial Sequence
<220> FEATURE:
<223> OTHER INFORMATION: Homo sapiens, chr5:9227136-9227164

<400> SEQUENCE: 68
ctctgttgtt attttttggt caatatctg                                     29

<210> SEQ ID NO 69
<211> LENGTH: 23
<212> TYPE: DNA
<213> ORGANISM: Artificial Sequence
<220> FEATURE:
<223> OTHER INFORMATION: Homo sapiens, chr8:127788996-127789018

<400> SEQUENCE: 69
gagtcctagc aggagaagaa gag                                           23

<210> SEQ ID NO 70
<211> LENGTH: 21
<212> TYPE: DNA
<213> ORGANISM: Artificial Sequence
<220> FEATURE:
<223> OTHER INFORMATION: Homo sapiens, chr8:127788953-127788973

<400> SEQUENCE: 70
aaagcctgga ggctgccagg t                                             21
```

```
<210> SEQ ID NO 71
<211> LENGTH: 24
<212> TYPE: DNA
<213> ORGANISM: Artificial Sequence
<220> FEATURE:
<223> OTHER INFORMATION: Homo sapiens, chr8:127789131-127789154

<400> SEQUENCE: 71
atctagctgt cctgtctcat tggc                                          24

<210> SEQ ID NO 72
<211> LENGTH: 23
<212> TYPE: DNA
<213> ORGANISM: Artificial Sequence
<220> FEATURE:
<223> OTHER INFORMATION: Homo sapiens, chr2:218980334-218980356

<400> SEQUENCE: 72
gaggccgagc agaagaaaga cgg                                           23

<210> SEQ ID NO 73
<211> LENGTH: 17
<212> TYPE: DNA
<213> ORGANISM: Artificial Sequence
<220> FEATURE:
<223> OTHER INFORMATION: Homo sapiens, chr2:10350-10366
<300> PUBLICATION INFORMATION:
<308> DATABASE ACCESSION NUMBER: NG_023323.1
<309> DATABASE ENTRY DATE: 2016-10-07
<313> RELEVANT RESIDUES IN SEQ ID NO: (10350)..(10366)

<400> SEQUENCE: 73
caggagccgg gtgggag                                                  17

<210> SEQ ID NO 74
<211> LENGTH: 21
<212> TYPE: DNA
<213> ORGANISM: Artificial Sequence
<220> FEATURE:
<223> OTHER INFORMATION: Homo sapiens, chr2:218980463-218980483

<400> SEQUENCE: 74
cctcagcctt ccctcagcca c                                             21

<210> SEQ ID NO 75
<211> LENGTH: 23
<212> TYPE: DNA
<213> ORGANISM: Artificial Sequence
<220> FEATURE:
<223> OTHER INFORMATION: Homo sapiens, chr6:43769717-43769739

<400> SEQUENCE: 75
ggtgagtgag tgtgtgcgtg tgg                                           23

<210> SEQ ID NO 76
<211> LENGTH: 21
<212> TYPE: DNA
<213> ORGANISM: Artificial Sequence
<220> FEATURE:
<223> OTHER INFORMATION: Homo sapiens, chr6:43769662-43769682

<400> SEQUENCE: 76
ctgggtgaat ggagcgagca g                                             21

<210> SEQ ID NO 77
```

```
<211> LENGTH: 20
<212> TYPE: DNA
<213> ORGANISM: Artificial Sequence
<220> FEATURE:
<223> OTHER INFORMATION: Homo sapiens, chr6:43769824-43769843

<400> SEQUENCE: 77
ggaaggcgga gagccggaca                                            20

<210> SEQ ID NO 78
<211> LENGTH: 23
<212> TYPE: DNA
<213> ORGANISM: Artificial Sequence
<220> FEATURE:
<223> OTHER INFORMATION: Homo sapiens, chr14:65102435-65102457

<400> SEQUENCE: 78
agtgagtgag tgtgtgtgtg ggg                                        23

<210> SEQ ID NO 79
<211> LENGTH: 21
<212> TYPE: DNA
<213> ORGANISM: Artificial Sequence
<220> FEATURE:
<223> OTHER INFORMATION: Homo sapiens, chr14:65102393-65102413

<400> SEQUENCE: 79
gaaggggagg gggaagtcac c                                          21

<210> SEQ ID NO 80
<211> LENGTH: 20
<212> TYPE: DNA
<213> ORGANISM: Artificial Sequence
<220> FEATURE:
<223> OTHER INFORMATION: Homo sapiens, chr14:65102527-65102546

<400> SEQUENCE: 80
cgtgcgtgcc gccgttgatc                                            20

<210> SEQ ID NO 81
<211> LENGTH: 23
<212> TYPE: DNA
<213> ORGANISM: Artificial Sequence
<220> FEATURE:
<223> OTHER INFORMATION: Homo sapiens, chr5:116098962-116098984

<400> SEQUENCE: 81
tgtgggtgag tgtgtgcgtg agg                                        23

<210> SEQ ID NO 82
<211> LENGTH: 23
<212> TYPE: DNA
<213> ORGANISM: Artificial Sequence
<220> FEATURE:
<223> OTHER INFORMATION: Homo sapiens, chr5:116098932-116098954

<400> SEQUENCE: 82
tctgtcacca cacagttacc acc                                        23

<210> SEQ ID NO 83
<211> LENGTH: 24
<212> TYPE: DNA
<213> ORGANISM: Artificial Sequence
<220> FEATURE:
<223> OTHER INFORMATION: Homo sapiens, chr5:116099133-116099156

<400> SEQUENCE: 83
```

-continued

```
gtagttgcct ggggatgggg tatg                                    24
```

<210> SEQ ID NO 84
<211> LENGTH: 23
<212> TYPE: DNA
<213> ORGANISM: Artificial Sequence
<220> FEATURE:
<223> OTHER INFORMATION: Homo sapiens, chr22:37266777-37266799

<400> SEQUENCE: 84

```
gctgagtgag tgtatgcgtg tgg                                     23
```

<210> SEQ ID NO 85
<211> LENGTH: 25
<212> TYPE: DNA
<213> ORGANISM: Artificial Sequence
<220> FEATURE:
<223> OTHER INFORMATION: Homo sapiens, chr22:37266726-37266750

<400> SEQUENCE: 85

```
cacctggccc atttctcctt tgagg                                   25
```

<210> SEQ ID NO 86
<211> LENGTH: 24
<212> TYPE: DNA
<213> ORGANISM: Artificial Sequence
<220> FEATURE:
<223> OTHER INFORMATION: Homo sapiens, chr22:37266856-37266879

<400> SEQUENCE: 86

```
tggggacagc atgtgcaagc caca                                    24
```

<210> SEQ ID NO 87
<211> LENGTH: 23
<212> TYPE: DNA
<213> ORGANISM: Artificial Sequence
<220> FEATURE:
<223> OTHER INFORMATION: Homo sapiens, chr14:29676-29698
<300> PUBLICATION INFORMATION:
<308> DATABASE ACCESSION NUMBER: KI270846.1
<309> DATABASE ENTRY DATE: 2017-01-06
<313> RELEVANT RESIDUES IN SEQ ID NO: (29676)..(29698)

<400> SEQUENCE: 87

```
ggtgagtgag tgtgtgtgtg agg                                     23
```

<210> SEQ ID NO 88
<211> LENGTH: 21
<212> TYPE: DNA
<213> ORGANISM: Artificial Sequence
<220> FEATURE:
<223> OTHER INFORMATION: Homo sapiens, chr14:29625-29645
<300> PUBLICATION INFORMATION:
<308> DATABASE ACCESSION NUMBER: KI270846.1
<309> DATABASE ENTRY DATE: 2017-01-06
<313> RELEVANT RESIDUES IN SEQ ID NO: (29625)..(29645)

<400> SEQUENCE: 88

```
ggacccctct gacagactgc a                                       21
```

<210> SEQ ID NO 89
<211> LENGTH: 23
<212> TYPE: DNA
<213> ORGANISM: Artificial Sequence
<220> FEATURE:
<223> OTHER INFORMATION: Homo sapiens, chr14:29760-29782
<300> PUBLICATION INFORMATION:

<308> DATABASE ACCESSION NUMBER: KI270846.1
<309> DATABASE ENTRY DATE: 2017-01-06
<313> RELEVANT RESIDUES IN SEQ ID NO: (29760)..(29782)

<400> SEQUENCE: 89
cacacaccct cacataccct cac					23

<210> SEQ ID NO 90
<211> LENGTH: 23
<212> TYPE: DNA
<213> ORGANISM: Artificial Sequence
<220> FEATURE:
<223> OTHER INFORMATION: Homo sapiens, chr5:90145146-90145168

<400> SEQUENCE: 90
agagagtgag tgtgtgcatg agg					23

<210> SEQ ID NO 91
<211> LENGTH: 27
<212> TYPE: DNA
<213> ORGANISM: Artificial Sequence
<220> FEATURE:
<223> OTHER INFORMATION: Homo sapiens, chr5:90145191-90145217

<400> SEQUENCE: 91
ggaagaatgc aaaggagaag caagtac					27

<210> SEQ ID NO 92
<211> LENGTH: 24
<212> TYPE: DNA
<213> ORGANISM: Artificial Sequence
<220> FEATURE:
<223> OTHER INFORMATION: Homo sapiens, chr5:90145038-90145061

<400> SEQUENCE: 92
gacctggtgg gagttgattg gatc					24

<210> SEQ ID NO 93
<211> LENGTH: 23
<212> TYPE: DNA
<213> ORGANISM: Artificial Sequence
<220> FEATURE:
<223> OTHER INFORMATION: Homo sapiens, chr20:20197634-20197656

<400> SEQUENCE: 93
agtgtgtgag tgtgtgcgtg tgg					23

<210> SEQ ID NO 94
<211> LENGTH: 27
<212> TYPE: DNA
<213> ORGANISM: Artificial Sequence
<220> FEATURE:
<223> OTHER INFORMATION: Homo sapiens, chr20:20197688-20197714

<400> SEQUENCE: 94
ccttgggaat ctatcttgaa taggcct					27

<210> SEQ ID NO 95
<211> LENGTH: 22
<212> TYPE: DNA
<213> ORGANISM: Artificial Sequence
<220> FEATURE:
<223> OTHER INFORMATION: Homo sapiens, chr20:20197546-20197567

<400> SEQUENCE: 95
gacaccccac acactctcat gc					22

<210> SEQ ID NO 96
<211> LENGTH: 23
<212> TYPE: DNA
<213> ORGANISM: Artificial Sequence
<220> FEATURE:
<223> OTHER INFORMATION: Homo sapiens, chr14:61612049-61612071

<400> SEQUENCE: 96
tgtgagtaag tgtgtgtgtg tgg                                           23

<210> SEQ ID NO 97
<211> LENGTH: 24
<212> TYPE: DNA
<213> ORGANISM: Artificial Sequence
<220> FEATURE:
<223> OTHER INFORMATION: Homo sapiens, chr14:61612099-61612122

<400> SEQUENCE: 97
cctaagctgt atgtgagtcc ctga                                          24

<210> SEQ ID NO 98
<211> LENGTH: 29
<212> TYPE: DNA
<213> ORGANISM: Artificial Sequence
<220> FEATURE:
<223> OTHER INFORMATION: Homo sapiens, chr14:61611941-61611969

<400> SEQUENCE: 98
ctgttttgct aagagatgat tagatggtc                                     29

<210> SEQ ID NO 99
<211> LENGTH: 23
<212> TYPE: DNA
<213> ORGANISM: Artificial Sequence
<220> FEATURE:
<223> OTHER INFORMATION: Homo sapiens, chr10:97000825-97000847

<400> SEQUENCE: 99
gttgagtgaa tgtgtgcgtg agg                                           23

<210> SEQ ID NO 100
<211> LENGTH: 21
<212> TYPE: DNA
<213> ORGANISM: Artificial Sequence
<220> FEATURE:
<223> OTHER INFORMATION: Homo sapiens, chr10:97000874-97000894

<400> SEQUENCE: 100
gccctctccg gaagtgcctt g                                             21

<210> SEQ ID NO 101
<211> LENGTH: 24
<212> TYPE: DNA
<213> ORGANISM: Artificial Sequence
<220> FEATURE:
<223> OTHER INFORMATION: Homo sapiens, chr10:97000734-97000757

<400> SEQUENCE: 101
gaagggttgg tttggaaggc tgtc                                          24

<210> SEQ ID NO 102
<211> LENGTH: 23
<212> TYPE: DNA
<213> ORGANISM: Artificial Sequence
<220> FEATURE:

<223> OTHER INFORMATION: Homo sapiens, chr11:69083658-69083680

<400> SEQUENCE: 102
ggtgagtgag tgcgtgcggg tgg                                              23

<210> SEQ ID NO 103
<211> LENGTH: 24
<212> TYPE: DNA
<213> ORGANISM: Artificial Sequence
<220> FEATURE:
<223> OTHER INFORMATION: Homo sapiens, chr11:69083595-69083618

<400> SEQUENCE: 103
ccacaggaat ttgaagtccg tgct                                             24

<210> SEQ ID NO 104
<211> LENGTH: 22
<212> TYPE: DNA
<213> ORGANISM: Artificial Sequence
<220> FEATURE:
<223> OTHER INFORMATION: Homo sapiens, chr11:69083735-69083756

<400> SEQUENCE: 104
ccccacgtcc acccatacac ac                                               22

<210> SEQ ID NO 105
<211> LENGTH: 23
<212> TYPE: DNA
<213> ORGANISM: Artificial Sequence
<220> FEATURE:
<223> OTHER INFORMATION: Homo sapiens, chr14:73886777-73886799

<400> SEQUENCE: 105
agcgagtggg tgtgtgcgtg ggg                                              23

<210> SEQ ID NO 106
<211> LENGTH: 21
<212> TYPE: DNA
<213> ORGANISM: Artificial Sequence
<220> FEATURE:
<223> OTHER INFORMATION: Homo sapiens, chr14:73886731-73886751

<400> SEQUENCE: 106
gacgtctggg tcccgagcag t                                                21

<210> SEQ ID NO 107
<211> LENGTH: 19
<212> TYPE: DNA
<213> ORGANISM: Artificial Sequence
<220> FEATURE:
<223> OTHER INFORMATION: Homo sapiens, chr14:73886873-73886891

<400> SEQUENCE: 107
ggccgtcagt cggtcccga                                                   19

<210> SEQ ID NO 108
<211> LENGTH: 23
<212> TYPE: DNA
<213> ORGANISM: Artificial Sequence
<220> FEATURE:
<223> OTHER INFORMATION: Homo sapiens, chr16:79982417-79982439

<400> SEQUENCE: 108
tgtgagtgag tgtgtgcgtg tga                                              23

```
<210> SEQ ID NO 109
<211> LENGTH: 25
<212> TYPE: DNA
<213> ORGANISM: Artificial Sequence
<220> FEATURE:
<223> OTHER INFORMATION: Homo sapiens, chr16:79982476-79982500

<400> SEQUENCE: 109
ggagggttga actgtgacag aactg                                         25

<210> SEQ ID NO 110
<211> LENGTH: 26
<212> TYPE: DNA
<213> ORGANISM: Artificial Sequence
<220> FEATURE:
<223> OTHER INFORMATION: Homo sapiens, chr16:79982303-79982328

<400> SEQUENCE: 110
tgagtatgtg tgagtgagag tgtgca                                        26

<210> SEQ ID NO 111
<211> LENGTH: 23
<212> TYPE: DNA
<213> ORGANISM: Artificial Sequence
<220> FEATURE:
<223> OTHER INFORMATION: Homo sapiens, chr19:40055954-40055976

<400> SEQUENCE: 111
actgtgtgag tgtgtgcgtg agg                                           23

<210> SEQ ID NO 112
<211> LENGTH: 21
<212> TYPE: DNA
<213> ORGANISM: Artificial Sequence
<220> FEATURE:
<223> OTHER INFORMATION: Homo sapiens, chr19:40056024-40056044

<400> SEQUENCE: 112
gatccttagg cgtgcgtgtg c                                             21

<210> SEQ ID NO 113
<211> LENGTH: 21
<212> TYPE: DNA
<213> ORGANISM: Artificial Sequence
<220> FEATURE:
<223> OTHER INFORMATION: Homo sapiens, chr19:40055878-40055898

<400> SEQUENCE: 113
caccggcaca gtgacactca c                                             21

<210> SEQ ID NO 114
<211> LENGTH: 23
<212> TYPE: DNA
<213> ORGANISM: Artificial Sequence
<220> FEATURE:
<223> OTHER INFORMATION: Homo sapiens, chr5:29367266-29367288

<400> SEQUENCE: 114
tgtgagtgag tgtgtgtatg ggg                                           23

<210> SEQ ID NO 115
<211> LENGTH: 24
<212> TYPE: DNA
<213> ORGANISM: Artificial Sequence
<220> FEATURE:
<223> OTHER INFORMATION: Homo sapiens, chr5:29367302-29367325
```

```
<400> SEQUENCE: 115
agaccttcaa tgtggatgtg cgtg                                              24

<210> SEQ ID NO 116
<211> LENGTH: 29
<212> TYPE: DNA
<213> ORGANISM: Artificial Sequence
<220> FEATURE:
<223> OTHER INFORMATION: Homo sapiens, chr5:29367042-29367070

<400> SEQUENCE: 116
catagagtgt agcagatttc cataacttc                                         29

<210> SEQ ID NO 117
<211> LENGTH: 22
<212> TYPE: DNA
<213> ORGANISM: Artificial Sequence
<220> FEATURE:
<223> OTHER INFORMATION: Homo sapiens, chr6:43769231-43769252

<400> SEQUENCE: 117
gcatacgtgg gctccaacag gt                                                22

<210> SEQ ID NO 118
<211> LENGTH: 22
<212> TYPE: DNA
<213> ORGANISM: Artificial Sequence
<220> FEATURE:
<223> OTHER INFORMATION: Homo sapiens, chr6:43770011-43770032

<400> SEQUENCE: 118
ccgcaatgaa ggggaagctc ga                                                22

<210> SEQ ID NO 119
<211> LENGTH: 23
<212> TYPE: DNA
<213> ORGANISM: Artificial Sequence
<220> FEATURE:
<223> OTHER INFORMATION: Homo sapiens, chr15:84621797-84621819

<400> SEQUENCE: 119
gtgcggcaag agcttcagcc ggg                                               23

<210> SEQ ID NO 120
<211> LENGTH: 21
<212> TYPE: DNA
<213> ORGANISM: Artificial Sequence
<220> FEATURE:
<223> OTHER INFORMATION: Homo sapiens, chr15:84621375-84621395

<400> SEQUENCE: 120
gactgtgggc agaggttcag c                                                 21

<210> SEQ ID NO 121
<211> LENGTH: 24
<212> TYPE: DNA
<213> ORGANISM: Artificial Sequence
<220> FEATURE:
<223> OTHER INFORMATION: Homo sapiens, chr15:84622203-84622226

<400> SEQUENCE: 121
tgtatacggg acttgactca gacc                                              24

<210> SEQ ID NO 122
<211> LENGTH: 23
```

-continued

<210> SEQ ID NO 122
<211> LENGTH: 23
<212> TYPE: DNA
<213> ORGANISM: Artificial Sequence
<220> FEATURE:
<223> OTHER INFORMATION: Homo sapiens, chr2:72933595-72933617

<400> SEQUENCE: 122
ctgccatccc cttctgtgaa tgt                                           23

<210> SEQ ID NO 123
<211> LENGTH: 22
<212> TYPE: DNA
<213> ORGANISM: Artificial Sequence
<220> FEATURE:
<223> OTHER INFORMATION: Homo sapiens, chr2:72934372-72934393

<400> SEQUENCE: 123
ggaatctacc accccaggct ct                                            22

<210> SEQ ID NO 124
<211> LENGTH: 23
<212> TYPE: DNA
<213> ORGANISM: Artificial Sequence
<220> FEATURE:
<223> OTHER INFORMATION: Homo sapiens, chr6:43770819-43770841

<400> SEQUENCE: 124
gaccccctcc accccgcctc cgg                                           23

<210> SEQ ID NO 125
<211> LENGTH: 20
<212> TYPE: DNA
<213> ORGANISM: Artificial Sequence
<220> FEATURE:
<223> OTHER INFORMATION: Homo sapiens, chr6:43770305-43770324

<400> SEQUENCE: 125
tcagcggact caccggccag                                               20

<210> SEQ ID NO 126
<211> LENGTH: 20
<212> TYPE: DNA
<213> ORGANISM: Artificial Sequence
<220> FEATURE:
<223> OTHER INFORMATION: Homo sapiens, chr6:43771025-43771044

<400> SEQUENCE: 126
gcgccgagtc gccactgcgg                                               20

<210> SEQ ID NO 127
<211> LENGTH: 23
<212> TYPE: DNA
<213> ORGANISM: Artificial Sequence
<220> FEATURE:
<223> OTHER INFORMATION: Homo sapiens, chr11:22625792-22625814

<400> SEQUENCE: 127
gctgcagaag ggattccatg agg                                           23

<210> SEQ ID NO 128
<211> LENGTH: 21
<212> TYPE: DNA
<213> ORGANISM: Artificial Sequence
<220> FEATURE:
<223> OTHER INFORMATION: Homo sapiens, chr11:22625410-22625430

<400> SEQUENCE: 128

```
gccaggctct cttggagtgt c                                              21

<210> SEQ ID NO 129
<211> LENGTH: 24
<212> TYPE: DNA
<213> ORGANISM: Artificial Sequence
<220> FEATURE:
<223> OTHER INFORMATION: Homo sapiens, chr11:22626287-22626310

<400> SEQUENCE: 129
agcatagcgc ctggcattaa tagg                                           24

<210> SEQ ID NO 130
<211> LENGTH: 23
<212> TYPE: DNA
<213> ORGANISM: Artificial Sequence
<220> FEATURE:
<223> OTHER INFORMATION: Homo sapiens, chr22:36556948-36556970

<400> SEQUENCE: 130
gctgcagaag ggattccaag agg                                            23

<210> SEQ ID NO 131
<211> LENGTH: 24
<212> TYPE: DNA
<213> ORGANISM: Artificial Sequence
<220> FEATURE:
<223> OTHER INFORMATION: Homo sapiens, chr22:36556738-36556761

<400> SEQUENCE: 131
cccgtgaggt gctgagattt gaac                                           24

<210> SEQ ID NO 132
<211> LENGTH: 21
<212> TYPE: DNA
<213> ORGANISM: Artificial Sequence
<220> FEATURE:
<223> OTHER INFORMATION: Homo sapiens, chr22:36557440-36557460

<400> SEQUENCE: 132
cacatggagg aggtgacgct g                                              21

<210> SEQ ID NO 133
<211> LENGTH: 23
<212> TYPE: DNA
<213> ORGANISM: Artificial Sequence
<220> FEATURE:
<223> OTHER INFORMATION: Homo sapiens, chr3:46373262-46373284

<400> SEQUENCE: 133
ggtacctatc gattgtcagg agg                                            23

<210> SEQ ID NO 134
<211> LENGTH: 24
<212> TYPE: DNA
<213> ORGANISM: Artificial Sequence
<220> FEATURE:
<223> OTHER INFORMATION: Homo sapiens, chr3:46372884-46372907

<400> SEQUENCE: 134
atgcacaggg tggaacaaga tgga                                           24

<210> SEQ ID NO 135
<211> LENGTH: 24
<212> TYPE: DNA
<213> ORGANISM: Artificial Sequence
```

```
<220> FEATURE:
<223> OTHER INFORMATION: Homo sapiens, chr3:46373989-46374012

<400> SEQUENCE: 135
ctaagccatg tgcacaactc tgac                                              24

<210> SEQ ID NO 136
<211> LENGTH: 23
<212> TYPE: DNA
<213> ORGANISM: Artificial Sequence
<220> FEATURE:
<223> OTHER INFORMATION: Homo sapiens, chr3:46357923-46357945

<400> SEQUENCE: 136
ggtatctatc gattgtcagg agg                                               23

<210> SEQ ID NO 137
<211> LENGTH: 23
<212> TYPE: DNA
<213> ORGANISM: Artificial Sequence
<220> FEATURE:
<223> OTHER INFORMATION: Homo sapiens, chr3:46357814-46357836

<400> SEQUENCE: 137
cattgtgggc tcactctgct gca                                               23

<210> SEQ ID NO 138
<211> LENGTH: 25
<212> TYPE: DNA
<213> ORGANISM: Artificial Sequence
<220> FEATURE:
<223> OTHER INFORMATION: Homo sapiens, chr3:46358817-46358841

<400> SEQUENCE: 138
ctgagatgag ctttctggag agtca                                             25
```